(12) United States Patent
Griffith et al.

(10) Patent No.: US 9,987,225 B2
(45) Date of Patent: Jun. 5, 2018

(54) CROSSLINKED HYDROGELS AND RELATED METHOD OF PREPARATION

(75) Inventors: May Griffith, Carp (CA); Fengfu Li, Gloucester (CA); Jae-Il Ahn, Ottawa (CA)

(73) Assignee: Ottawa Hospital Research Institute, Ottawa (CA)

( * ) Notice: Subject to any disclaimer, the term of this patent is extended or adjusted under 35 U.S.C. 154(b) by 605 days.

(21) Appl. No.: 13/499,088

(22) PCT Filed: Sep. 29, 2010

(86) PCT No.: PCT/CA2010/001516
§ 371 (c)(1),
(2), (4) Date: Jun. 18, 2012

(87) PCT Pub. No.: WO2011/038485
PCT Pub. Date: Apr. 7, 2011

(65) Prior Publication Data
US 2012/0321585 A1 Dec. 20, 2012

Related U.S. Application Data

(60) Provisional application No. 61/247,391, filed on Sep. 30, 2009.

(51) Int. Cl.
| | |
|---|---|
| *A61K 31/785* | (2006.01) |
| *A61K 9/06* | (2006.01) |
| *A61K 9/00* | (2006.01) |
| *A61K 31/522* | (2006.01) |
| *A61K 41/00* | (2006.01) |
| *A61K 47/42* | (2017.01) |
| *A61L 27/24* | (2006.01) |
| *A61L 27/52* | (2006.01) |
| *C08H 1/06* | (2006.01) |
| *C08J 3/075* | (2006.01) |
| *C08J 3/24* | (2006.01) |
| *C08K 5/00* | (2006.01) |
| *C08K 5/29* | (2006.01) |
| *C08L 89/06* | (2006.01) |
| *A61K 49/00* | (2006.01) |
| *A61K 38/39* | (2006.01) |

(52) U.S. Cl.
CPC .............. *A61K 9/06* (2013.01); *A61K 9/0051* (2013.01); *A61K 31/522* (2013.01); *A61K 41/0042* (2013.01); *A61K 47/42* (2013.01); *A61L 27/24* (2013.01); *A61L 27/52* (2013.01); *C08H 1/06* (2013.01); *C08J 3/075* (2013.01); *C08J 3/24* (2013.01); *C08K 5/0025* (2013.01); *C08K 5/29* (2013.01); *C08L 89/06* (2013.01); *A61K 38/39* (2013.01); *A61K 49/0073* (2013.01); *A61L 2430/16* (2013.01); *C08J 2300/16* (2013.01); *C08J 2389/06* (2013.01)

(58) Field of Classification Search
None
See application file for complete search history.

(56) References Cited

U.S. PATENT DOCUMENTS

| | | | | |
|---|---|---|---|---|
| 5,487,895 | A | * | 1/1996 | Dapper et al. ............. 424/278.1 |
| 5,731,005 | A | * | 3/1998 | Ottoboni et al. ............. 424/499 |
| 6,005,160 | A | | 12/1999 | Hsiue et al. |
| 7,476,398 | B1 | | 1/2009 | Doillon et al. |
| 2006/0134170 | A1 | * | 6/2006 | Griffith ................. A61F 9/0017 424/427 |

FOREIGN PATENT DOCUMENTS

| | | |
|---|---|---|
| CA | 2 577 025 | 2/2006 |
| CA | 2 686 132 | 11/2007 |
| CA | 2 671 572 | 6/2008 |
| WO | WO-2005/113608 | 12/2005 |
| WO | WO-2006/015490 | 2/2006 |
| WO | WO-2006/042272 | 4/2006 |
| WO | WO-2007/028258 | 3/2007 |
| WO | WO-2007/124198 | 11/2007 |

OTHER PUBLICATIONS

Milne et al. "Crosslinking of collagen gels: photochemical measurements", SPIE vol. 1644 Ophthalmic Technologies 11(1992) / 1.*
Bareiss et al., "Controlled Release of Acyclovir Through Bioengineered Corneal Implants with Silica Nanoparticle Carriers," The Open Tissue Engineering and Regenerative Medicine Journal 3:10-17 (2010).
Beems et al., "Light Transmission of the Cornea in Whole Human Eyes," Exp. Eye Res. 50(4):393-395 (1990).
Caporossi et al., "Long-term Results of Riboflavin Ultraviolet A Corneal Collagen Cross-linking for Keratoconus in Italy: The Siena Eye Cross Study," Am J Ophthalmol. 149(4):585-93 (2010).
Carlsson et al., "Bioengineered corneas: how close are we?," Current Opin. Ophthalmol., 14:192-197 (2003).
Chvapil et al., "Effect of Tanning Agent on Tissue Reaction to Tissue Implanted Collagen Sponge," J Surg Res 35:402-409 (1983).
Doillon et al., "Porosity and biological properties of polyethylene glycol-conjugated collagen materials," J. Biomater. Sci. Polymer Edn, 6(8):715-728 (1994).
Eybl et al., "Toxic effects of aldehydes released from fixed pericardium on bovine aortic endothelial cells," J. Biomed. Mater. Res., 23:1355-1365 (1989).

(Continued)

*Primary Examiner* — James W Rogers
(74) *Attorney, Agent, or Firm* — Foley Hoag LLP

(57) ABSTRACT

The present invention provides a method of manufacturing a hydrogel comprising the step of crosslinking a biopolymer using a carbodiimide crosslinker of Formula I wherein at least one of $R^1$ and $R^2$ is a functional group that is a bulky organic functional group. $R^1$ and $R^2$ can each independently be an optionally substituted saturated or unsaturated functional group selected from the group consisting of an alkyl, a cycloalkyl, a heterocyclic, and an aryl. The bulky organic functional group will slow down the crosslinking reaction of carbodiimide due to the steric effects and/or electronic effects, in comparison to a crosslinking reaction using EDC. Also provided are the hydrogels and ophthalmic devices prepared using the method of the invention and uses thereof.

8 Claims, 52 Drawing Sheets

(56) References Cited

OTHER PUBLICATIONS

Griffith et al., "Functional human corneal equivalents constructed from cell lines," Science 286: 2169-2172 (1999).
Hardy et al., "The Nature of the Cross-linking of Proteins by Glutaraldehyde. Part 2. The Formation of Quaternary Pyridinium Compounds by the Action of Glutaraldehyde on Proteins and the Identification of a 3-(2-Piperidyl)-pyridinium Derivative, Anabilysine, as a Cross-linking Entity," J. Chem. Soc. Perkin Trans I 2282-2288 (1979).
Hardy et al., "The Nature of the Crosslinking of Proteins by Glutaraldehyde. Part 1. Interaction of Glutaraldehyde with the Amino-groups of 6-Aminohexanoic Acid and of α-N-Acetyl-lysine," J. Chem. Soc. Perkin Trans I, (9):958-62 (1976).
Hey et al., "Crosslinked fibrous collagen for the use as a dermal implant:control of the cytotoxic effects of glutaraldehyde and dimethylsuberimidate," Biotechnol Appl Biochem 12:85-93 (1990).
Huang-Lee et al., "Biochemical changes and cytotoxicity associated with the degradation of polymeric glutaraldehyde derived crosslinks," J. Biomed. Mater. Res., 24:1185-1201 (1990).
Li et al., "Cellular and nerve regeneration within a biosynthetic extracellular matrix for corneal transplantation," PNAS USA, 100(26):15346-15351 (2003).
Li et al., "Recruitment of multiple cell lines by collagen-synthetic copolymer matrices in corneal regeneration," Biomaterials 26(16):3093-3104 (2005).
Liu et al., "A Simple, Cross-linked Collagen Tissue Substitute for Corneal Implantation," Invest. Ophthalmol. Vis. Sci 47(5):1869-1875 (2006).
Liu et al., "Collagen-phosphorylcholine interpenetrating network hydrogels as corneal substitutes," Biomaterials, 30(8):1551-1559 (2009).
Maurice, DM. The eye. In: Dayson H, editor. New York: Academic Press Inc; pp. 289-368; (1962).
Merrett et al., "Tissue Engineered Recombinant Human Collagen-Based Corneal Substitutes for Implantation: Performance of Type I versus Type III Collagen," Invest. Opthalmol. Vis. Sci., 49(9):3887-3894 (2008).
Nimni et al., "Chemically modified collagen: a natural biomaterial for tissue replacement," J. Biomed. Mater. Res. 21:741-771 (1987).
Olde Damink et al., "Cross-linking of dermal sheep collagen using a water-soluble carbodiimide," Biomaterials 17:765-773 (1996).
Patel et al. "Refractive index of human corneal epithelium and stoma," J Refract Surg 11:100e5 (1995).
Petite et al., "Use of the acyl azide method for cross-linking collagen-rich tissue such as pericardium," J. Biomed. Mater. Res. 24(2):179-187 (1990).
Rafat et. al., "PEG-stabilized carbodiimide crosslinked collagen-chitosan hydrogels for corneal tissue engineering," Biomaterials, 29(29):3960-3972 (2008).
Snibson, GR, "Collagen cross-linking : a new treatment paradigm in corneal disease—a review," Clinical and Experimental Opthamology, 38:141-153 (2010).
Traubel H. Gerbung mit Isocyanaten, 1. Teil. Das leder 11:150-4 (1977).
Tsai et al., "Reconstruction of damaged corneas by transplantation of autologous limbal epithelial cells," New England J. Medicine 343:86-93 (2000).
Van Wachem et al., "In vivo biocompatibility of carbodiimide-crosslinked collagen matrices: Effects of crosslink density, heparin immobilization and bFGF loading," J. Biomed. Mater. Res. 55:368-378 (2001).
Weadock et al., "Evaluation of collagen crosslinking techniques," Biomater Med Dev Artif Organs 11:293-318 (1983-84).
Whitcher et al., "Prevention of Corneal Ulceration in the Developing World," Int. Ophthalmol. Clin., 42:71-77 (2002).
Zeeman et al., "Successive epoxy and carbodiimide cross-linking of dermal sheep collagen," Biomaterials 20:921-931 (1999).
Zeng et al., "A comparison of biomechanical properties between human and porcine cornea," J. Biomech., 34:533-537 (2001).
Supplementary European Search Report dated Jan. 30, 2013 from EP 10 81 9764.
Doillon et al., "A collagen-based scaffold for a tissue engineered human cornea: Physical and physiological properties," International Journal of Artificial Organs, 26(8):764-773 (2003).
International Search Report dated Jan. 6, 2011 from PCT/CA2010/001516.
European Office Action Communication Pursuant to Article 94(3) EPC dated Mar. 9, 2016 in European Patent Application No. 10819764.1.
Canadian Office Action dated Apr. 13, 2017 in Canadian Patent App. No. 2,775,670.
Canadian Office Action dated Jun. 17, 2016 in Canadian Patent App. No. 2,775,670.
European Office Action Communication Pursuant to Article 94(3) EPC dated Feb. 3, 2017 in European Patent App. No. 10819764.1.
European Search Report for European Patent Application No. 10819764.1, dated Mar. 2, 2017.
Priest et al., "A new instrument for monitoring the optical properties of corneas," Invest Ophthalmol Vis Sci 39(Suppl):s352 (1998).

* cited by examiner

A

B

C

D

A

B

C

D

A

B

Hydrogel in vitro biodegradation in collagenase

Hydrogel in vitro biodegradation in collagenase

A

B

C

D

A

B

A　　　　　　　　　　B

A

B

A

B

A

B

CROSSLINKED HYDROGELS AND RELATED METHOD OF PREPARATION

CROSS-REFERENCE TO RELATED APPLICATION

The present application is the U.S. National Stage of International Patent Application No. PCT/CA2010/001516, filed Sep. 29, 2010, which claims priority from United States Provisional Patent Application No. 61/247,391, filed Sep. 30, 2009, the entire contents of which are hereby incorporated by reference.

FIELD OF THE INVENTION

The present invention pertains to the field of hydrogels. More particularly, the present invention pertains to the field of crosslinked biopolymer containing hydrogels and methods of manufacture and use thereof.

BACKGROUND

Tissue engineering is a rapidly growing field encompassing a number of technologies aimed at replacing or restoring tissue and organ function. The key objective in tissue engineering is the regeneration of a defective tissue through the use of materials that can integrate into the existing tissue so as to restore normal tissue function. Tissue engineering, therefore, demands materials that can support cell overgrowth, in-growth, or encapsulation and, in many cases, nerve regeneration.

Various crosslinkers have been used to crosslink biopolymer scaffolds, such as collagen scaffolds, in diverse tissue engineering fields [12-15]. Collagen in the body makes stabilization of collagen-based biomaterials and chemical cross-linking methods necessary to give materials that maintain the desired mechanical properties and stability during the desired implantation period [16]. Crosslinking methods can be divided into two general methodologies based on the crosslinker chemistry [16]. One crosslinking methodology makes use of bifunctional reagents, which can be used to bond amine groups of lysine or hydroxylysine by monomeric or oligomeric crosslinks. Based on the use of bifunctional reagents for crosslinking, glutaraldehyde (GA) has generally been applied for the crosslinking of collagen-based materials [17]. The use of hexamethylene diisocyanate (HMDIC) as a cross-linking agent was introduced by Chvapil et al [18]. GA cross-linking involves the formation of short (branched) aliphatic chains and pyridinium compounds [19, 20], while in HMDIC cross-linking aliphatic chains containing urea bonds are introduced between two adjacent amine groups [21]. Both GA and HMDIC crosslinking may lead to the presence of unreacted functional groups (probably aldehyde or amine groups after hydrolysis of isocyanate groups) in the collagen matrix, which can result in a cytotoxic reaction upon degradation of the collagen. Furthermore, it has been reported that GA crosslinked collagen-based biomaterials releases toxic GA (related) molecules from the biomaterial, which may result from unreacted GA present in the samples or from hydrolytic or enzymatic degradation products. This may also contribute to the cytotoxic reactions elicited by these materials both in vitro and in vivo [22. 23].

The GA crosslinkers has been used to bridge amine groups of lysine or hydroxylysine residues of collagen polypeptide chains. However, one major disadvantage of these cross-linking agents is the potential toxic effect of residual molecules when the biomaterial is exposed to biological environments. e.g., during in vivo degradation.

A second crosslinking methodology makes use of amide type crosslinkers. They could be formed by activation of the carboxylic acid groups of glutamic and aspartic acid residues followed by reaction of these activated carboxylic acid groups with amine groups of another polypeptide chain [24]. Cross-linking methods based on the concept of cross-linking by activation of carboxylic acid groups have been developed. The use of cyanamide for cross-linking of reconstituted collagen was first reported by Weadock et al [25]. However carbodiimide type crosslinkers, especially 1-ethyl-3-(3-dimethylaminopropyl)carbodiimide hydrochloride (EDC) and N-hydroxysuccinimide NHS, offer the main advantage of lower toxicity and better compatibility over other crosslinkers [26]. The acyl azide activation method was used for cross-linking of pericardium. Using these methods, direct cross-linking of the polypeptide chains occurs, resulting in the formation of amide-type crosslinks [27].

In principal, no unreacted groups will be left in the material during crosslinking provided that reagents used for the activation of the carboxylic acid groups are easily removed. Cross-linking of collagen-based biomaterials using these methods resulted in materials with a similar resistance against degradation by bacterial collagenase compared with GA cross-linked materials. The influence of N-hydroxysuccinimide (NHS) on the activation of the carboxylic acid groups and subsequent cross-linking of the collagen material was studied [16].

The cornea is a transparent, avascular tissue, the structure of which allows it to serve as both a barrier to the outside environment and as an optical pathway. Vision loss due to corneal disease or trauma affects over 10 million individuals worldwide. For many, although treatable by corneal transplantation, donor tissue demand exceeds supply, especially in the developing countries [1-3]. While corneal substitutes have been proposed, to date, the only substitutes clinically tested in humans have been fully synthetic keratoprostheses (KPros). Although improving, complications with keratoprostheses, including retroprosthetic membrane formation, calcification, infection, and glaucoma, have limited their use to cases not treatable by human donor grafting [4]. Prostheses therefore do not alleviate the primary need for human donor corneas, especially in the developing world where the shortage of human donor corneas is acute.

An alternative approach is to enhance the inherent regenerative capacity of the human cornea to restore healthy, viable tissue. Tissue-engineered mimics of the extracellular matrix (ECM) have been proposed as scaffolds for endogenous tissue regeneration. In this regard, a range of biomimetic corneal substitutes have been developed, comprising either crosslinked medical grade porcine or recombinant human collagen [5] or hybrid collagen-synthetic [6-8] materials. These materials have provided robust, implantable, cornea-shaped scaffolds.

A simple biomimetic corneal substitute based on human collagen crosslinked with EDC (1-Ethyl-3-(3-dimethyl aminopropyl) carbodiimide hydrochloride) has been previously reported. This simple but biointeractive corneal substitute has been successfully tested in pig models, showing regeneration of corneal cells and nerves [5]. Although EDC was used successfully in previous experiments, the gelation time of collagen hydrogel crosslinked EDC was very short, making it very difficult to fabricate hydrogels. As a result, the fabrication process must be performed at cold temperature, preferably at 0-4° C., at which temperature the gelation may still be too quick for facilitating fabrication of hydrogels and biopolymers for various uses. Additionally, a short gelation time makes it difficult to produce hydrogels and biopolymers that incorporate corneal stem or progenitor cells using EDC as the crosslinker, since the collagen solution must be mixed with corneal fibroblasts before gelation of the collagen.

There remains a need for an alternative to EDC as a crosslinker in fabricating hydrogels. In particular, a method that would permit collagen, or another suitable biopolymer, to gel slowly at room temperature slowly would be particularly useful for producing hydrogels useful in various medical applications, including ophthalmic devices, such as, for example, corneal substitutes and corneal implants.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide cross-linked hydrogels and a method of manufacture thereof. In accordance with one aspect, there is provided a method of manufacturing a hydrogel comprising the step of crosslinking a biopolymer using a carbodiimide crosslinker compound of Formula I

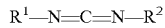

wherein at least one of $R^1$ and $R^2$ is a functional group that is a bulky organic functional group. Optionally, the bulky organic functional group is bulkier than the ethyl and dimethyl aminopropyl moieties of EDC. $R^1$ and $R^2$ can each independently be an optionally substituted saturated or unsaturated functional group selected from the group consisting of an alkyl, a cycloalkyl, a heterocyclic, and an aryl. In accordance with another embodiment, the carbodiimide crosslinker is water soluble. In one embodiment, $R^1$ and $R^2$ each comprise a cycloalkyl or heterocyclic group. In one particular embodiment, the compound of Formula I is CMC ((N-Cyclohexyl-N'-(2-morpholinoethyl)carbodiimide metho-p-toluenesulfonate):

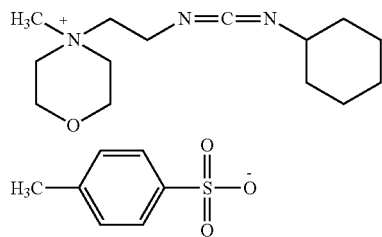

In accordance with another aspect, there is provided a hydrocarbon prepared by a method that includes the step of crosslinking a biopolymer using a carbodiimide crosslinker of Formula I:

wherein at least one of $R^1$ and $R^2$ can each independently be an optionally substituted saturated or unsaturated functional group selected from the group consisting of an alkyl, a cycloalkyl, a heterocyclic, and an aryl, as defined above.

Optionally, the bulky organic functional group is selected to slow down the crosslinking reaction of carbodiimide. In particular, the bulky organic functional group can be selected to permit collagen, or another suitable biopolymer, to gel slowly at room temperature. It has been found that a carbodiimide crosslinker comprising one or more bulky organic functional groups is particularly suitable for preparing hydrogels. In certain embodiments, a carbodiimide crosslinker of Formula I, wherein $R^1$ and $R^2$ are independently and optionally saturated or unsaturated functional groups selected from the group consisting of an alkyl, a cycloalkyl, a heterocyclic, and an aryl group, is a carbodiimide crosslinker containing a bulky organic functional group effective at slowing down the crosslinking reaction of the carbodiimide.

In some aspects, the present invention provides a method of manufacturing a hydrogel comprising the step of crosslinking a biopolymer using a carbodiimide crosslinker of Formula I or a salt thereof, wherein at least one of the $R^1$ and $R^2$ groups is a functional group that is a bulky organic functional group. In certain embodiments, $R^1$ and $R^2$ are each independently an optionally substituted saturated or unsaturated functional group selected from the group consisting of an alkyl, a cycloalkyl, a heterocyclic, and an aryl group. In other embodiments, the biopolymer is collagen, preferably human collagen, and more preferably recombinant human collagen. In yet other embodiments, the present invention provides a method of manufacturing a hydrogel comprising the step of crosslinking a biopolymer using a carbodiimide crosslinker of Formula I or a salt thereof, wherein at least one of the $R^1$ and $R^2$ groups is a functional group that is a bulky organic functional group, and further wherein the biopolymer is collagen, wherein the collagen consists of type III collagen, human type III collagen, or recombinant human type III collagen.

In some aspects, the present invention provides a hydrogel prepared by crosslinking a biopolymer using a carbodiimide crosslinker of Formula I or a salt thereof, wherein at least one of the $R^1$ and $R^2$ groups is a functional group that is a bulky organic functional group. In certain embodiments, $R^1$ and $R^2$ are each independently an optionally substituted saturated or unsaturated functional group selected from the group consisting of an alkyl, a cycloalkyl, a heterocyclic, and an aryl group. In other embodiments, the biopolymer is collagen, preferably human collagen, and more preferably recombinant human collagen. In yet other embodiments, the present invention provides a hydrogel prepared by crosslinking a biopolymer using a carbodiimide crosslinker of Formula I or a salt thereof, wherein at least one of the $R^1$ and $R^2$ groups is a functional group that is a bulky organic functional group, and further wherein the biopolymer is collagen, wherein the collagen consists of type III collagen, human type III collagen, or recombinant human type III collagen. In certain embodiments, the hydrogel is an ophthalmic device, including, for example, a corneal substitute or a corneal implant.

In some aspects, the present invention provides a method for treating an ophthalmic condition in a subject in need thereof, the method comprising implanting in the subject a hydrogel prepared by crosslinking a biopolymer using a carbodiimide crosslinker of Formula I or a salt thereof, wherein at least one of the $R^1$ and $R^2$ groups is a functional group that is a bulky organic functional group. In certain embodiments, $R^1$ and $R^2$ are each independently an optionally substituted saturated or unsaturated functional group selected from the group consisting of an alkyl, a cycloalkyl, a heterocyclic, and an aryl group. In other embodiments, the biopolymer is collagen, preferably human collagen, and more preferably recombinant human collagen. In yet other embodiments, the present invention provides a method for treating an ophthalmic condition in a subject in need thereof, the method comprising implanting in the subject a hydrogel prepared by crosslinking a biopolymer using a carbodiimide crosslinker of Formula I or a salt thereof, wherein at least one of the $R^1$ and $R^2$ groups is a functional group that is a bulky organic functional group, and further wherein the biopolymer is collagen, wherein the collagen consists of type III collagen, human type III collagen, or recombinant human type III collagen. In certain embodiments, the hydrogel is an ophthalmic device, including, for example, a corneal substitute or a corneal implant. In certain embodiments, the ophthalmic condition is an ophthalmic disease, disorder, or injury, including a disease, disorder, or injury to the cornea.

The present invention also provides an ophthalmic device prepared according to the methods described herein. The ophthalmic device can be a corneal substitute or a corneal implant. In certain embodiments, the ophthalmic device according to the present invention may be a corneal onlay, a corneal inlay, or a full-thickness corneal implant.

DETAILED DESCRIPTION OF THE INVENTION

Figure 1:
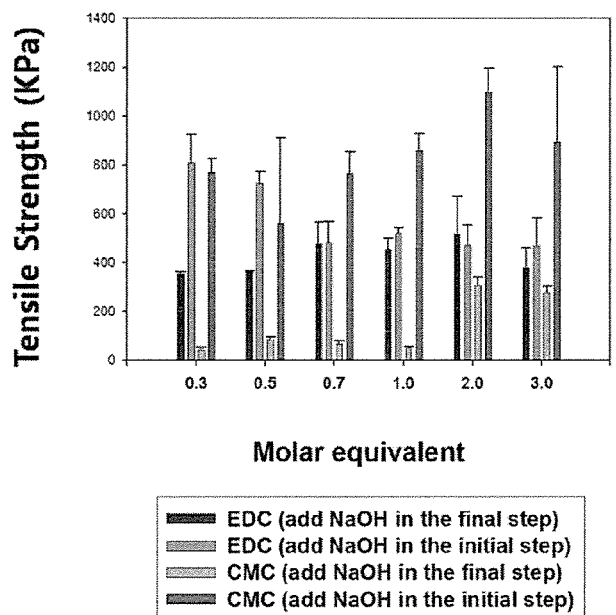
FIG. 1 graphically depicts the comparison of mechanical properties of collagen hydrogels crosslinked by either EDC or CMC. (A) Tensile strength, (B) Elongation break, (C) Modulus, (D) Toughness. Error bars; standard deviation (n=3 samples for each data point).
Figure 1:
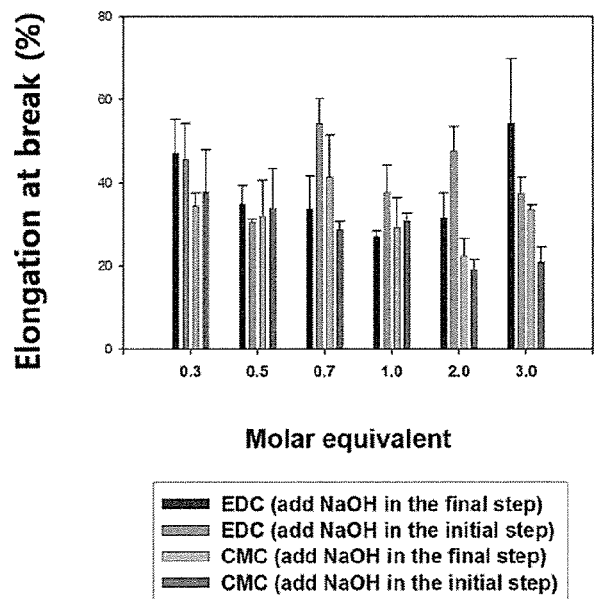
Figure 1:
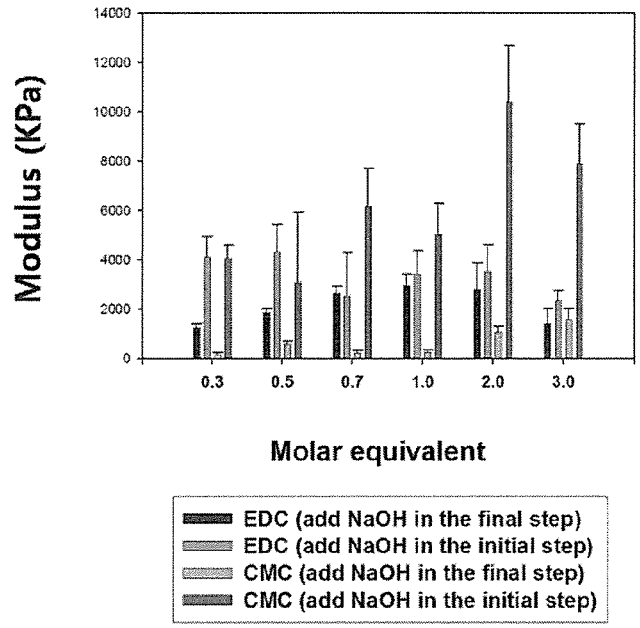
Figure 1:
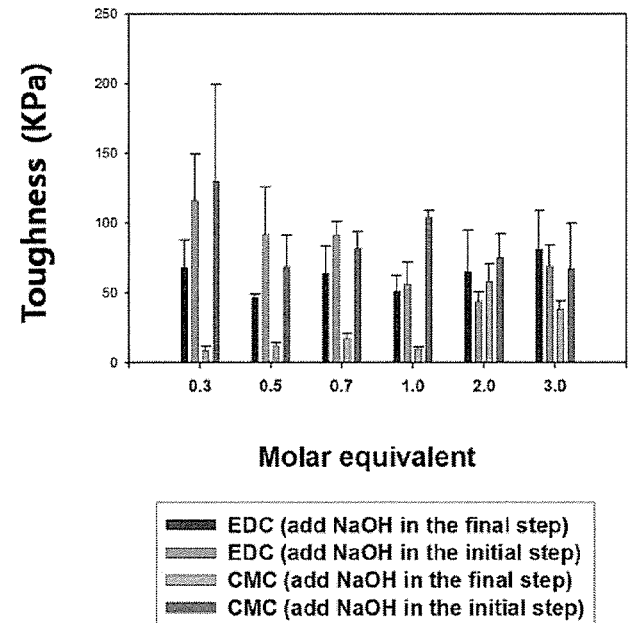

Definitions: Unless defined otherwise, all technical and scientific terms used herein have the same meaning as commonly understood by one of ordinary skill in the art to which this invention belongs.

The term "hydrogel," as used herein, refers to a crosslinked polymeric material which exhibits the ability to swell in water or aqueous solution without dissolution and to retain a significant portion of water or aqueous solution within its structure.

The term "polymer," as used herein, refers to a molecule consisting of individual monomers joined together. In the context of the present invention, a polymer may comprise monomers that are joined "end-to-end" to form a linear molecule, or may comprise monomers that are joined together to form a branched structure.

The term "bio-polymer," as used herein, refers to a naturally occurring polymer. Naturally occurring polymers include, but are not limited to, proteins and carbohydrates. The term "bio-polymer" also includes derivatised forms of the naturally occurring polymers that have been modified to facilitate cross-linking to a synthetic polymer of the invention. Additionally, the term "bio-polymer," as used herein, includes proteins produced using recombinant methodologies, such as, for example, recombinant collagen.

The term "synthetic polymer," as used herein, refers to a polymer that is not naturally occurring and that is produced by chemical synthesis.

The term "interpenetrating network" or "IPN", as used herein, refers to an interpenetrating polymeric network, which is a combination of two or more polymers in which each polymer forms a network. There is entanglement and interactions between the networks. When swollen in a solvent, none of the polymers will dissolve in the solvent.

As used herein, "transparent" refers to transmission of light.

As used herein, "optically clear" refers to at least 70%, or 80%, or 85% or 90% transmission of white light. In certain embodiments, "optically clear" refers to optical clarity that is equivalent to that of a healthy cornea, for example, having greater than 90% transmission of white light and less than about 4.5% scatter, or less than about 4% scatter or less than about 3% scatter.

As used herein, the term "bulky", when used in the context of a functional group, refers to an organic functional group which adds bulk to the compound to which it is bound. In this context, a bulky organic functional group typically has greater volume in proportion to weight. Suitable bulky functional groups can be selected that slow down the speed (i.e., gelation time) of the crosslinking reaction of carbodiimide with a biopolymer. Optionally, the bulky organic functional group is bulkier than the ethyl and dimethyl aminopropyl moieties of EDC. Without wishing to be bound by theory, the bulkier the $R^1$ and $R^2$, the slower the rate of the carbodiimide reaction, due to the steric effects and/or electronic effects, in comparison to a crosslinking reaction using such as EDC as the crosslinker. Also, without wishing to be bound by theory, the stronger the electron donor effect of $R^1$ and $R^2$, the slower the reaction of carbodiimide.

In accordance with one embodiment, at least one of $R^1$ and $R^2$ is a functional group that is a bulky organic functional group. $R^1$ and $R^2$ can each independently be an optionally substituted saturated or unsaturated functional group selected from the group consisting of alkyl, cycloalkyl, heterocyclic and aryl. In accordance with another embodiment, the carbodiimide crosslinker is water soluble. In one embodiment, $R^1$ and $R^2$ each independently comprise a cycloalkyl or heterocyclic group. In one particular embodiment, the compound of Formula I is CMC ((N-Cyclohexyl-N'-(2-morpholinoethyl)carbodiimide metho-p-toluenesulfonate):

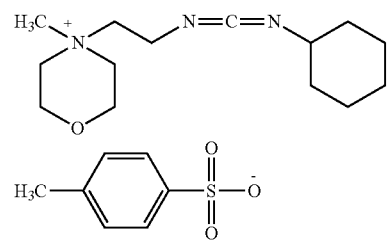

The present invention is based on the finding that biopolymer based hydrogels can be prepared with good mechanical and physical properties, that are particularly suited for use in tissue engineering applications, by using a carbodiimide crosslinker with stronger steric and/or electron-donating effect groups than are present in previously employed crosslinkers, such as EDC. The bulkier and/or electron donating groups on the carbodiimide crosslinker can slow down the biopolymer crosslinking reactions, can produce transparent collagen hydrogel fabrication at room temperature, and can make the gelation slower than that observed when using EDC as a crosslinker. It also can generate stronger collagen hydrogels than those crosslinked with EDC/NHS.

Ideally, a bulky carbodiimide can make the processing of the current collagen-based hydrogel or its composite hydrogel easier and more workable and provides the opportunity to better control the formation of the hydrogel because of the slower crosslinking reaction. Proteins crosslinked with water-soluble carbodiimides that have stronger steric or electronic effect groups offer superior reaction kinetics. The slower reaction time and room temperature usage offers better control over mixing and hence overall homogeneity of the resulting constructs. The superior kinetics also allows for more homogenous incorporation of microspheres, nanoparticles, or other inclusions in the fabrication of composite materials for use as substrates or scaffolds in tissue engineering or regenerative medicine applications. The control over the reaction time is particularly important in achieving homogeneity. The homogeneity is, in turn, important in achieving the optical clarity that is critical when the material is produced for ophthalmic applications.

Micro or nanoparticles loaded with drugs or therapeutic proteins can be fabricated into in the hydrogels, or the drugs or protein motifs can be directly incorporated into the hydrogels. For example, a drug incorporated into the hydrogel can be, e.g., acyclovir; and the protein incorporated into the hydrogel can be, e.g., NGF, LL37.

Crosslinking using a bulky carbodiimide can be employed in protein-based hydrogel preparation, for example, in ophthalmic application such as corneal substitutes and corneal implants, and in other areas of tissue engineering and regenerative medicine, as well as in the fabrication of drug, therapeutic, or vaccine delivery vehicles.

Hydrogel Material

A hydrogel material in accordance with the present invention comprises a crosslinked biopolymer and is suitable for use in a variety of applications, including, but not limited to, clinical, therapeutic, prophylactic, or cosmetic applications. The hydrogel material can be used to replace, restore, and/or augment tissue and/or organ function in a subject in need thereof.

Hydrogels in accordance with the present invention can have various biomedical, biotechnological, and/or pharmaceutical applications such as, for example, corneal substitutes, therapeutic lenses, cell and/or drug delivery carriers, tissue engineering scaffolds, or in regenerative medicine such as for spinal cord regeneration healing.

A hydrogel in accordance with the present invention is characterized by low cytotoxicity or no cytotoxicity, ability to facilitate cell and/or nerve growth, and/or moldability. Selection of these characteristics is based on the ultimate application of the hydrogel. The material also has sufficient mechanical and structural properties to permit handling, implantation, and the like, which may include suturing, and post-installation wear and tear. In accordance with one embodiment of the present invention, devices made from the hydrogel material are produced using molds. Such devices include, but are not limited to, molded ophthalmic onlays and implants, which are formed to the desired size and shape.

The hydrogel, in accordance with one embodiment, is suitable for use in therapeutic applications, in part, because it is (i) shapeable, such as moldable, to form a matrix with an acceptable biological properties, (ii) effective in facilitating nerve growth through and/or over the hydrogel, and, in the case of ophthalmic devices, (iii) can be made optically clear or visually transparent.

In accordance with a specific, non-limiting example, the hydrogel material is used in ophthalmic devices, wherein the material can provide one or more of the following benefits to an individual to whom the device is fitted: (i) a desired refractive index, (ii) a desired optical clarity (for visible light, optical transmission and light scattering equal to or better than those of healthy human cornea material of comparable thickness), (iii) a desired optical power, such as a vision enhancing optical power, (iv) enhanced comfort, (v) enhanced corneal and epithelial health, and (vi) therapeutic benefit, for example, in the treatment of a disease, disorder or traumatic injury of an eye. In accordance with this embodiment, the hydrogel material can be made transparent, or optically clear. The material can also be molded to include a vision corrective curvature.

In certain embodiments, a hydrogel produced according to the methods of the present invention comprises a bio-polymer, wherein the bio-polymer is a protein, such as collagen, and further wherein the collagen consists of type III collagen, such as human type III collagen or recombinant human type III collagen.

Bio-polymers

Bio-polymers are naturally-occurring polymers and their derivatives, such as proteins and carbohydrates. In accordance with the present invention, the hydrogel comprises a bio-polymer or a derivatised version thereof. Examples of suitable bio-polymers for use in the present invention include, but are not limited to, proteins, collagen (including collagen types I, II, III, IV, V, VI, and XI), denatured collagen (or gelatin), recombinant collagen (including recombinant type I collagen, recombinant type II collagen, recombinant type III collagen, recombinant type IV collagen, recombinant type V collagen, recombinant type VI collagen, and recombinant human type XI collagen), recombinant gelatin, chitosan, or any other biopolymers that possess both multiple amine groups and multiple carboxylic acid groups, or two polymers with one possessing multiple amine groups and the other possessing multiple carboxylic acid groups. In certain embodiments, the bio-polymer is a protein of human source or sequence, including, for example, human collagen, human type III collagen, or recombinant human type III collagen.

In certain embodiments, the bio-polymer is a collagen, wherein the collagen is of one collagen type free of any other collagen types. Therefore, in one embodiment, a hydrogel produced according to the methods of the present invention comprises a bio-polymer, wherein the bio-polymer is collagen, and further wherein the collagen consists of type III collagen, such as human type III collagen, or recombinant human type III collagen.

Suitable biopolymers for use in the invention can be purchased from various commercial sources, can be prepared from natural sources using standard techniques, or can be produced using recombinant production methodologies.

A bio-polymer or derivative thereof is selected based on one or more of the following properties: (1) the bio-polymer is bio-compatible and optionally promotes cell adhesion and growth and/or promotes nerve growth; and (2) the bio-polymer includes reactive groups which can be cross-linked by a carbodiimide.

In a specific example, transparent collagen hydrogels can be prepared by mixing collagen with CMC or CMC/NHS at pH 4-7, particularly at pH 5-5.5, at room temperature. Fabrication at room temperature allows for ease of scale up for manufacturing, especially under Good Manufacturing Practice (GMP) conditions. Temperature spikes are also potentially better tolerated with crosslinkers that work at room temperature over those with a narrow range around 4° C.

In preparing the collagen hydrogels of the present invention, the ratio of carbodiimide, for example, CMC, to collagen-amine equivalent is ranged from about 0.1 to about 3.0, from about 0.7 to about 3.0, from about 1.0 to about 2.0, or about 2.0; NHS/CMC is ranged from about 0.1 to about 10, or from about 0.5 to about 2. In collagen solutions comprising 10% collagen, such as 10% pig type I collagen solution, the ratio of CMC to collagen-amine equivalent is about 0.3 to about 3.0, or about 2.0. In collagen solutions comprising about 13.7% collagen, such as recombinant human collagen, the ratio of CMC to collagen-amine equivalent is about 0.4 to about 1.5, or about 1.0. In collagen solutions comprising about 18.0% collagen, such as recombinant human collagen, the ratio of CMC to collagen-amine equivalent is about 0.4 to about 1.5, or about 0.7.

The collagen hydrogel such as, for example, used as corneal implant ophthalmic device ideally has a white light transmission of at least 70%, or at least 80%, or at least 85%, or at least 90%.

Optionally, MPC (2-methacryloyloxyethyl phosphorylcholine) and PEG-DA (polyethylene glycol-diacrylate) can be added to form a composite material such as collagen-MPC hydrogel. In this alternative, any water-soluble acrylic or methacrylic derivatives or acrylamide and derivatives can be used to replace MPC. MES buffer can be used to help maintain pH of mixture in preparing an MPC containing hydrogel. Further, alizarin red S may be used as pH indicator of the mixture.

Crosslinker

In accordance with one aspect of the present invention, the crosslinker used in the preparation of a hydrogel is a carbodiimide crosslinker of Formula I:

$$R^1-N=C=N-R^2 \qquad I$$

wherein at least one of $R^1$ and $R^2$ is a functional group that is a bulky organic functional group. $R^1$ and $R^2$ can each independently be an optionally substituted saturated or unsaturated functional group selected from the group consisting of an alkyl, a cycloalkyl, a heterocyclic, and an aryl. In accordance with another embodiment, the carbodiimide crosslinker is water soluble. In one embodiment, $R^1$ and $R^2$ each comprise a cycloalkyl or a heterocyclic group. In one particular embodiment, the compound of Formula I is CMC ((N-Cyclohexyl-N'-(2-morpholinoethyl)carbodiimide metho-p-toluenesulfonate). Ideally, a suitably bulky organic functional group is selected to slow down the crosslinking reaction of carbodiimide. Without wishing to be bound by theory, it is thought that this may be due to the steric effects and/or electronic effects, in comparison to a crosslinking reaction using EDC; thus, suitable bulky $R^1$ and $R^2$ groups will slow the rate of the carbodiimide reaction.

To enhance the inherent regenerative capacity of the human cornea, one approach is through implantation of corneal template scaffold to restore vision. Animal-derived collagen hydrogels cross-linked by cross-linker poly(N-isopropylacrylamide-co-acrylic acid-co-acryloxysucciimide) (denoted as TERP) [5a] and poly (acrylamide-co-acryloxysucciimide) (denoted as COP) [6a] or 1-Ethyl-3-(3-dimethyl aminopropyl) carbodiimide hydrochloride (EDC) [7a] have shown promise in promoting corneal tissue regeneration including cells and nerves in animal models. The fabrication of a simple biomimetic corneal substitute comprised of recombinant human collagen cross-linked with EDC has been reported previously and is herein incorporated by reference [5].

Various cross-linking agents used in synthesizing collagen scaffolds in the tissue engineering field currently exist [12-15]. The chemical cross-linking methods can be divided into two categories. The first chemical cross-linking group is based on the use of bifunctional reagents, such as glutaraldehyde which has generally been applied for the cross-linking of collagen-based materials [17]. In addition to glutaraldehyde (GA), hexamethylene diisocyanate (HMDIC) has also been used to cross-link collagen [14]. Both GA and HMDIC have been found to leave un-reacted functional groups in the collagen matrix following cross-linking which can result in a cytotoxic reaction upon degradation of the collagen [22,23]. The second chemical cross-linking group is that of the amide type cross-linkers. They can be formed by activation of the carboxylic acid groups followed by reaction with amine groups of another polypeptide chain [15]. The carbodiimide type cross-linkers especially EDC and NHS offer the main advantage of lower toxicity and better compatibility over other cross-linkers [26]. Using these methods, direct cross-linking of the polypeptide chains occurs, resulting in the formation of amide-type cross-links [19a]. In principal, no un-reacted groups will be left in the material during cross-linking provided that reagents used for the activation of the carboxylic acid groups are easily removed. Cross-linking of collagen-based biomaterials using these methods resulted in materials with a similar resistance against degradation by bacterial collagenase relative to GA cross-linked materials [13a].

Figure 14:
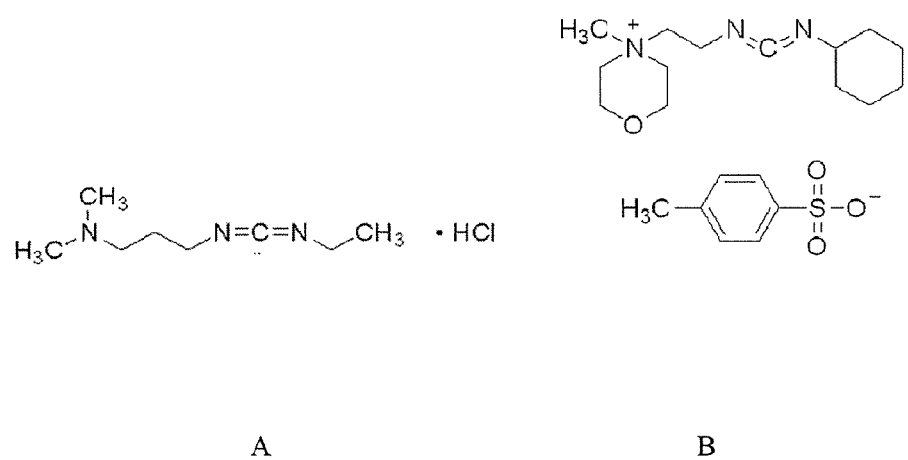
FIG. 14 provides the structures of EDC (A) and CMC (B).

Although progress has been made, occasionally there were challenges in the fabrication of these collagen-based hydrogels due to the fast gelation of collagen in the presence of EDC cross-linkers. For example, collagen gelation with EDC at around pH 5 occurs within a few minutes even when cooled. It has now been recognized by the present inventors that slower gelation times may also be desired in order to potentially seed cells in the collagen hydrogel. In search of slower cross-linking methods for collagen, N-cyclohexyl-N'-(2-morpholinoethyl) carbodiimide metho-p-toluenesulfonate (CMC) was selected, which contains two bulky groups, cyclohexyl and 2-morpholinoethyl on either side of the diimide moiety (FIG. 14). In comparison, the two groups on each side of the diimide of EDC, ethyl and dimethyl aminopropyl, are far less bulkier than those on the CMC. Thus, the bulkier CMC has been shown to slow down the cross-linking reaction in comparison to EDC, likely due to steric hinderance effects.

In accordance with another embodiment, the carbodiimide crosslinker is water soluble. Advantageously, the water soluble crosslinker is CMC (N-Cyclohexyl-N'-(2-morpholinoethyl)carbodiimide metho-p-toluenesulfonate.

CMC is a commercially available carbodiimide, which has pendant groups that provide sufficient steric hinderance to slow down the reaction kinetics, allowing for more control over the hydrogel manufacturing process than the widely known and used EDC benchmark. The present inventors have found that CMC has a longer gelation time than EDC and crosslinking can be achieved at room temperature, facilitating better control of the mixing process and potentially allowing for more homogenous constructs. In addition, CMC-crosslinked hydrogels had similar or superior properties in comparison to EDC crosslinked controls.

As noted above, the slower reaction time/superior kinetics also allows for potentially more homogenous incorporation of microspheres, nanoparticles, or other inclusions in the fabrication of composite materials for use as substrates or scaffolds in tissue engineering or regenerative medicine applications. The control over the reaction time is particularly important in achieving homogeneity and in turn, optical clarity, that is critical in the production of materials for ophthalmic applications.

CMC, and similarly bulky and/or electron donating carbodiimide crosslinkers, are therefore potentially superior crosslinkers in the fabrication of crosslinked biopolymer (e.g., collagen) hydrogels and more likely to lend themselves to the requisite scaling-up in manufacturing of hydrogels, such as in the fabrication of ophthalmic devices, such as corneal substitutes and corneal implants.

To gain a better understanding of the invention described herein, the following examples are set forth. It should be understood that these examples are for illustrative purposes only. Therefore, they should not limit the scope of this invention in any way.

EXAMPLES

Abbreviations used herein:
1. MPC, 2-Methacryloyloxyethyl phosphorylcholine;
2. PEGDA, poly(ethylene glycol) diacrylate;
3. MES, 2-(N-morpholino)ethanesulfonic acid;
4. EDC, 1-ethyl-3-(3-dimethyl aminopropyl) carbodiimide hydrochloride;
5. NHS, N-hydroxysuccinimide;
6. CMC, 1-cyclohexyl-3-(2-morpholinoethyl)-carbodiimide metho-p-toluenesulfonate;
7. IRGA, i.e. IRGACURE 2959, 4-(2-hydroxyethoxy) phenyl-(2-hydroxy-2-propyl)ketone.
8. APS, ammonium persulphate;
9. TEMED, N,N,N',N'-tetramethylethylene diamine.

Example 1

Comparison of EDC to CMC Crosslinker

CMC (N-Cyclohexyl-N'-(2-morpholinoethyl) carbodiimide metho-p-toluenesulfonate) includes a cyclohexyl and a morpholinoethyl group. CMC was selected as a non-toxic crosslinker for comparing the gelation speed of collagen solution, in comparison to gelation using EDC as a cross-linker, because of its bulky groups. The collagen hydrogels were fabricated using a 10% collagen solution and crosslinker (EDC, CMC). The properties and in vitro biocompatibility of the resulting hydrogels were compared.

Materials and Methods

Freeze-dried Type I porcine collagen was purchased by Nippon Meat Packers Inc. (Tokyo, Japan). Morpholinoethanesulfonic acid (MES; EMD Chemicals Inc., USA) was dissolved in deionized water to form a 0.625 M MES buffer solution. 1-Ethyl-3-(3-dimethyl aminopropyl) carbodiimide hydrochloride (EDC) and N-Cyclohexyl-N'-(2-morpholinoethyl) carbodiimide metho-p-toluenesulfonate (CMC) were supplied by Sigma. N-hydroxysuccinimide (NHS) was supplied by Fluka (Buchs, Switzerland). Collagenase (type I *Clostridium histolyticum*, EC 3.4.24.3) was purchased from Sigma-Aldrich. Phosphate buffered saline (PBS, pH=7.4) was prepared from the tablet form (Calbiochem Corp, Darmstadt, Germany). Sodium hydroxide was dissolved in deionized water to form 2 N NaOH solution. Milli-Q deionized water (Millipore, Billerica, Md.) was used throughout. All other reagents were of analytical grade.

Preparation of Collagen Solution

The porcine collagen solution (10% w/w) was prepared by dissolving freeze-dried porcine collagen in water at 4° C. stirring with an electric-powered stirring shaft for 2 days. The collagen solutions was transferred into a plastic syringe, and centrifuged at 4° C. to completely remove suspended air bubbles to give a clear, viscous solution ready for use.

Preparation of Collagen Hydrogel

Two methods were employed for fabricating the collagen hydrogels. In Method A, NaOH was added in the last mixing step before plating. In Method B, NaOH was added in the early mixing step.

To begin the fabrication, 600 mg of 10% w/w bubble-free pig skin collagen solution was thoroughly mixed with 150 μl of MES (0.625 M) buffer in a syringe mixing system under an ice-water bath [9].

A. Collagen Hydrogel Crosslinked with EDC 1.0 (E-1.0) by Method A

The collagen mixture was injected with 10 μl of NHS solution taken from 100 μl of deionized water containing 26.2 mg of NHS. Thereafter, this mixture was injected with 10 μl of EDC solution taken from 100 μl of deionized water containing 43.7 mg of EDC and 2 N sodium hydroxide was added to adjust the pH to 5.5.

B. Collagen Hydrogel Crosslinked with EDC 3.0 (E-3.0) by Method B

The pH of the collagen mixture was raised using 2 N sodium hydroxide and was then injected with 10 μl of NHS solution taken from 100 μl of deionized water containing 78.6 mg of NHS. Thereafter, this mixture was injected with 10 μl of EDC solution taken from 100 μl of deionized water containing 131.1 mg of EDC.

C. Collagen Hydrogel Crosslinked with CMC 0.3 (C-0.3) by Method A

The collagen mixture was injected with 10 μl of NHS solution taken from 100 μl of deionized water containing 7.9 mg of NHS. Before adding CMC, the syringe mixing system was warmed in a 25° C. water bath for 10 minutes. Thereafter, the collagen mixture was injected with 10 μl of CMC solution taken from 100 μl of deionized water containing 29.0 mg of CMC and 2 N sodium hydroxide was added to adjust the pH to 5.5.

D. Collagen Hydrogel Crosslinked with CMC 0.7 (C-0.7) by Method B

The pH of the collagen mixture was raised using 2 N sodium hydroxide and was then injected with 10 μl of NHS solution taken from 100 μl of deionized water containing 18.4 mg of NHS. Thereafter, this mixture was injected with 10 μl of CMC solution taken from 100 μl of deionized water containing 67.7 mg of EDC.

After mixing of the collagen and crosslinker, the mixture was cast into curved plastic molds (thickness 500 μm, diameter 12 mm) or between two glass plates (10 cm×10 cm×0.25 cm) separated by a spacer frame with a thickness of 430 μm. The molds were left at room temperature with 100% humidity for 16 h, and then transferred into an incubator for post-curing at 37° C. for 5 h. After incubation, the molds were immersed in 10 mM PBS for 30 min, followed by cautious removal of the hydrogels from the molds. The resulting hydrogels, curved or flat, were eluted in PBS, which was replaced at 8 h intervals. The hydrogels were then immersed in 10 mM PBS containing 1% chloroform to maintain sterility and stored at 4° C. The detailed mixing times and temperature of hydrogel curing are listed in Table 2. Note that, for example, "EDC 1.0 (E-1.0)" indicates that the molar equivalent of EDC was 1.0.

TABLE 2

Conditions used in fabricating collagen hydrogels

| Method | | EDC | | CMC |
|---|---|---|---|---|
| A | 1 | Collagen + MES - 60 times (4° C.) | 1 | Collagen + MES - 60 times (4° C.) |
| | 2 | +NHS - 100 times (4° C.) | 2 | +NHS - 100 times (4° C.) |
| | 3 | +EDC - 100 times (4° C.) | 3 | +CMC - 100 times (4° C.) |
| | 4 | +NaOH - 140-200 times (4° C.) | 4 | +NaOH - 140-200 times (4° C.) |
| | 5 | Cast | 5 | Cast |
| B | 1 | Collagen + MES - 60 times (4° C.) | 1 | Collagen + MES - 60 times (4° C.) |
| | 2 | +NaOH - 140-200 times (4° C.) | 2 | +NaOH - 140-200 times (4° C.) |
| | 3 | +NHS - 100 times (4° C.) | 3 | +NHS - 100 times (4° C.) |
| | 4 | +EDC - 100 times (4° C.) | 4 | Wait - 10 min. (25° C.) |
| | 5 | Cast | 5 | +CMC - 100 times (25° C.) |
| | | | 6 | +CMC - 100 times (4° C.) |
| | | | 7 | Cast |

The molar equivalent ratio of EDC:NHS:number of ε-amine groups of collagen (Coll-$NH_2$) was 3:3:1.

As demonstrated in Table 2, the four methods of fabricating collagen hydrogels differed in terms of crosslinker and the order of addition of sodium hydroxide. Collagen hydrogels having molar equivalent 0.3, 0.5, 0.7, 1.0, 2.0 and 3.0 were made using each of the 4 methods.

Gelation Time

After casting, the remaining collagen mixture inside of syringe mixing system was used to measure gelation time. The remaining collagen mixture was placed in a small test tube which was then capped. The gelation time was measured using Pasteur pipette at 5 minute intervals.

Mechanical Properties

The tensile strength and elastic moduli of the hydrogels were measured using an Instron electromechanical universal tester (Model 3342, Instron, Canton, Mass.) equipped with Series IX/S software. Flat hydrogels, 0.43 mm thick, were equilibrated in PBS and cut into 12 mm×5 mm rectangular strips. The actual gauge length of each specimen was 5 mm for testing. Three specimens were measured for each hydrogel formulation. The crosshead speed was 10 mm/min.

Optical Properties

Refractive indices of flat and fully hydrated hydrogels equilibrated in PBS were recorded using an Abbe refractometer (Model C 10, VEE GEE Scientific Inc., Kirkland, Wash.) at 21° C. with bromonaphthalene as the calibration agent. Hydrogel light transmission and back-scattering measurements were carried out at 21° C. on a custom-built instrument described previously [10]. Differences in the optical properties between CMC and EDC crosslinking hydrogels were analyzed statistically using a one-way analysis of variance (ANOVA). All comparisons were a priori, pre-specified analyses using Tukey-Kramer to correct for multiple testing. Statistical significance was set at $P<0.05$.

Water Contents

After removal from the molds, hydrogels were immersed in PBS for 7 days at 4° C. The hydrogels were removed from PBS and the surface was gently blotted dry with filter paper, and then immediately weighed on a microbalance to record the wet weight of the sample. The hydrogels of known weight were then dried at room temperature under vacuum to constant weight. The total equilibrated water content of hydrogels (Wt) was calculated according to the following equation: $Wt=(W-W_0)/W \times 100\%$ where W and $W_0$ denote the wet weight and the dry weight of the samples, respectively.

Thermal Analysis (DSC)

The thermal properties of collagen solutions and collagen hydrogels were examined on a Perkin-Elmer DSC-2C differential scanning calorimeter (DSC). Heating scans were recorded in the range 8-80° C. at a scan rate of 5° C./min. Pre-weighed samples of collagen solution or PBS-equilibrated collagen hydrogels (weights ranging from 5 to 10 mg) were surface-dried with filter paper and hermetically sealed in an aluminum pan to prevent water evaporation. PBS was used as a blank reference. The denaturing temperature (Td) at the maximum of the endothermic peak and enthalpy (ΔHd) were measured.

In vitro Collagenase Biodegradation

In vitro biodegradation gives a measure of the relative stability of the hydrogel in vivo. Samples are exposed to high (non-physiological) concentrations of enzyme that accelerates degradation. Fifty to eighty milligrams of hydrogels were equilibrated for 1 h in 5 ml 0.1 M Tris-HCl buffer (ph 7.4), containing 5 mM $CaCl_2$ at 37° C. Subsequently, 1 mg/ml (288 U/ml) collagenase solution was added to give a final collagenase concentration of 5 U/ml. The solution was replaced every eight hours to retain enough activity of collagenase. At different time intervals, the hydrogels were weighed after the surface water was gently blotted off. Three samples were tested for each hydrogel formulation. The percent residual mass of hydrogels was calculated according to the following equation: Residual mass %=Wt/$W_0$, where $W_0$ is the initial weight of the hydrogel and Wt is the weight of the hydrogel at each time point.

In vitro Cell Compatibility

A. Corneal Epithelial Cells

Two Teflon™ rings (Bioland Ltd., Korea, diameter: 5 mm) were used to culture immortalized human corneal epithelial cells on the collagen hydrogel. Approximately 150 corneal epithelial cells (8 cells/$mm^2$) were seeded on the collagen hydrogel. Three pictures were taken to count cells at every 2 days. The medium used was supplemented with a serum-free medium containing epidermal growth factor (Keratinocyte Serum-Free Medium (KSFM), Life Technologies, Burlington, Canada) and changed every two days after taking pictures and grown until confluent.

B. Corneal Endothelial Cells

The Teflon ring was used to culture immortalized human corneal endothelial cells on collagen hydrogel. Approximately 2000 corneal endothelial cells (102 cells/$mm^2$) were seeded on the collagen hydrogel. Three (3) pictures were taken to count cells at every 2 days. The medium used was supplemented with a serum-free medium (Opti-MEM) containing FBS (8%), Ascorbic acid (20 mg/L), Human lipid mixture (50 μl/L), Chondroitin sulphate C (0.8 g/L), Calcium chloride (0.2 g/L), Gentamycin (0.5%), RPMI-multiple vitamin solution (1%), Antibiotic Antimycotic solution (1%), EDTA (0.2 g/L), FGF (25 mg/L), EGF (2.5 mg/L) and NGF (0.1 g/L) and changed every two days after taking pictures.

C. Nerve Cells

To determine the ability of the hydrogels to support nerve surface growth, dorsal root ganglia (DRG) from chick embryos (E 8.0) were dipped into collagen matrix as an adhesive, and adhered to the surface of washed hydrogel pieces. The medium used was supplemented with a serum-free medium (KSFM) containing B27 (2%), N2 (1%) and Retinoic acid (5 μM). Neurite growth was observed for up to a total of 6 days, after which the gels were fixed in 4% paraformaldehyde in 0.1 M PBS, pH 7.2-7.4 and stained for the presence of neurofilament using mouse anti-NF200 antibody overnight at 4° C. Neurofilament was visualized the following day using donkey antimouse-Cy2 secondary antibody. Whole mounts were imaged using a Zeiss Axiovert microscope. The number of neurites was counted reaching 150, 300, 450, 600, and 750 μm per 0.8775 mm2 area after 6 days of attachment on collagen hydrogel.

Results

Comparison of Gelation Time

The gelation time results are provided in Table 3 below. The results demonstrate that the collagen hydrogels crosslinked with CMC had a longer gelation time than those crosslinked using EDC in Method A when molar equivalent was equal or less than 1. However, there was little difference in gelation time when the molar equivalent was higher than 1 using Method A.

The gelation time of collagen hydrogels crosslinked using CMC was generally similar to that of hydrogels crosslinked using EDC at each molar equivalent using Method B. However, as set out above (Table 2), collagen hydrogel crosslinked with CMC and prepared using Method B, were made using a method that including two steps of 100 mixing times (at 25° C. and at 4° C.), which is twice the amount of mixing used to prepare hydrogels using EDC and Method B. Taking this into consideration, the results demonstrate that the collagen hydrogels crosslinked using CMC had a longer gelation time than those crosslinked EDC. This is consistent with the suggestion that the bulkier cyclohexyl groups of CMC slow down the gelation speed of collagen solution due to steric hinderance.

TABLE 3

The gelation time of collagen hydrogel crosslinked by EDC and CMC

| Method | Molar equivalent | 0.3 | 0.5 | 0.7 | 1.0 | 2.0 | 3.0 |
|---|---|---|---|---|---|---|---|
| A | EDC | 15-20 | 10-15 | 5-10 | <10 | 5-10 | <3 |
|   | CMC | 40 | 20-30 | 10-20 | 10 | 5-10 | <5 |
| B | EDC | 15-20 | 10-15 | 5-10 | 5-10 | <5 | <3 |
|   | CMC | 15-20 | 10-15 | 10-15 | 5-10 | <5 | <3 |

Method A: Adding NaOH in the last step
Method B: Adding NaOH in the early step

Mechanical Properties

FIG. 1 illustrates the tensile strength, elongation at break, elastic moduli and toughness of type I porcine collagen hydrogels prepared using Method A and different EDC/Coll-$NH_2$ and CMC/Coll-$NH_2$ ratios, and prepared using Method B and different EDC/Coll-$NH_2$ and CMC/Coll-$NH_2$ ratios.

Generally, the tensile strength of collagen hydrogels made using Method B was higher than that of the hydrogels prepared using Method A. When the molar equivalent of EDC was 0.3 and 0.5, the tensile strength of collagen hydrogels made using Method B was higher than that of hydrogels prepared using Method A. When the molar equivalent of collagen hydrogel with crosslinked by EDC was from 0.7 to 3, there was little difference in the tensile strength of collagen hydrogels prepared using Method B and Method A.

In contrast, the CMC crosslinked collagen hydrogels prepared using Method B all exhibited a higher tensile strength that those prepared by Method A at all molar equivalents tested. The tensile strength of collagen hydrogels crosslinked using CMC in Method A was the lowest of all experimental conditions (EDC (method A, B), CMC (method A, B)). The tensile strength of collagen hydrogel crosslinked EDC was higher than those crosslinked CMC when the molar equivalent of crosslinker was 0.3 or 0.5. However, the tensile strength of collagen hydrogel crosslinked CMC was higher than that crosslinked EDC when the molar equivalent of crosslinker was 0.7 to 3.0. Tensile strength of collagen hydrogel crosslinked with CMC or EDC was highest at the 2.0 and 0.3 molar equivalents, respectively. The highest tensile strength of all the collagen hydrogels, was found using the collagen hydrogel crosslinked with CMC at a molar equivalent 2.0 using Method B. The results demonstrate a clear difference in tensile strengths obtained using Method A and Method B for both crosslinkers.

The elongation at break for all the collagen hydrogels tested was between 20% and 60%. The modulus and toughness of all the collagen hydrogels tested exhibited a similar pattern to that observed for the tensile strength at each molar equivalent. When molar equivalent was higher than 0.5, the value of the hydrogel crosslinked using CMC was about 1.5-2 times higher than the tensile strength and modulus from the EDC crosslinked hydrogels. However, there was only a small difference observed in toughness.

Water Content of Collagen Hydrogel

Figure 2:
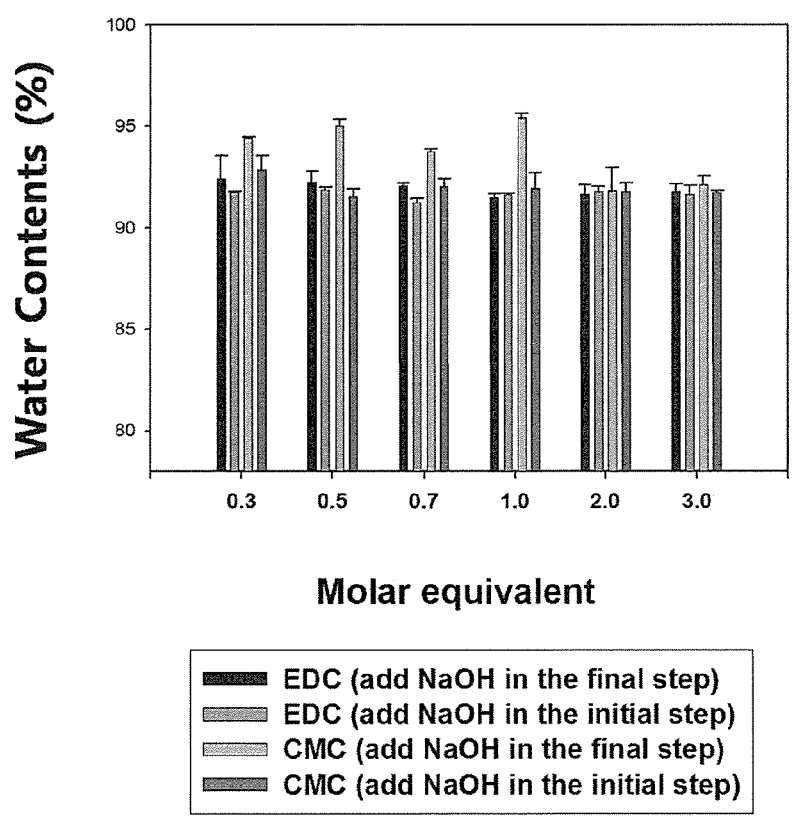
FIG. 2 graphically depicts the water content of collagen hydrogels prepared using EDC or CMC as a crosslinker.

FIG. 2 illustrates depicts the water content of collagen hydrogels prepared using EDC or CMC as a crosslinker. The water content of all the collagen hydrogels tested was between about 91% and 93%, except for the collagen hydrogel crosslinked with CMC at molar equivalents from 0.3 to 1.0 using Method A. The water content of these collagen hydrogels crosslinked using CMC were between 94% and 96% when molar equivalent of CMC was from 0.3 to 1.0. Thus, as the tensile strength of these hydrogels was low, the water content was high. Considering that the water content of normal cornea is approximately 78%, corneal applications will require about an extraction of about 13% water from the hydrogels with pumping.

Physical Properties of Collagen Hydrogel

A. Refractive Index

Figure 3:
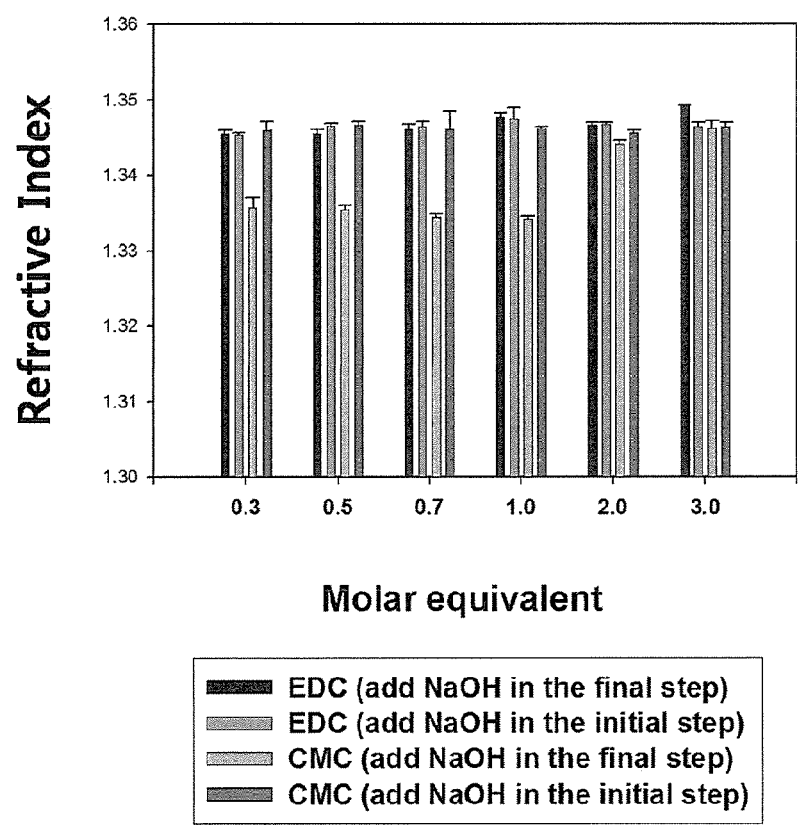
FIG. 3 graphically depicts the refractive indices of collagen hydrogels prepared using EDC or CMC as a crosslinker.

FIG. 3 depicts the refractive indices of collagen hydrogels prepared using EDC or CMC as a crosslinker. The refractive index of collagen hydrogels made by Method A was similar to the refractive index of the collagen hydrogels made by Method B. Similarly, there was little difference in the refractive indices of EDC and CMC crosslinked hydrogels.

However, the refractive index for CMC crosslinked hydrogels at a molar equivalent (ME) from 0.3 to 1.0 made using Method A was smaller than for the other hydrogels tested. Without wishing to be bound by theory, this may be because of a high water content of these the collagen hydrogel. The collagen hydrogel crosslinked using CMC and Method A at ME from 0.3 to 1 demonstrated a high water content and weak strength. The refractive index for all the collagen hydrogel tested (EDC, CMC, Method A, Method B) was lower than human corneal stroma. This is due to the fact that these hydrogels have a higher water content than normal cornea.

B. Optical Properties

Figure 4:
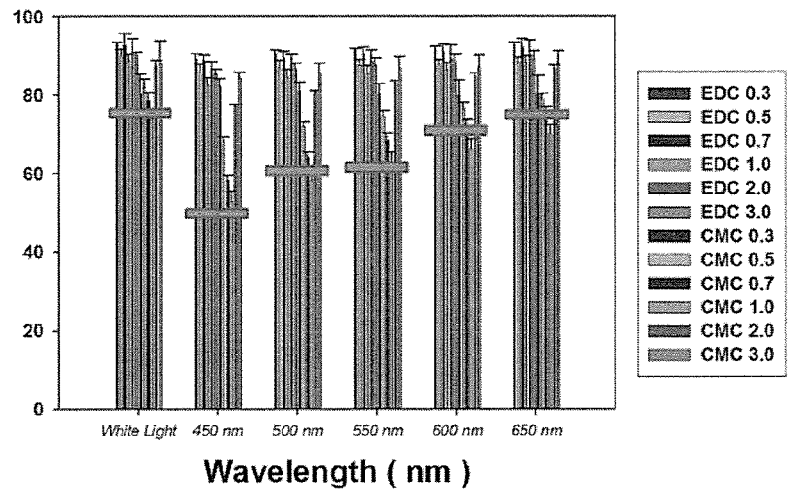
FIG. 4 graphically depicts white light transmission (A and B) and backscatter (C and D) of collagen hydrogels prepared using Method A (A and C) and Method B (B and D).
Figure 4:
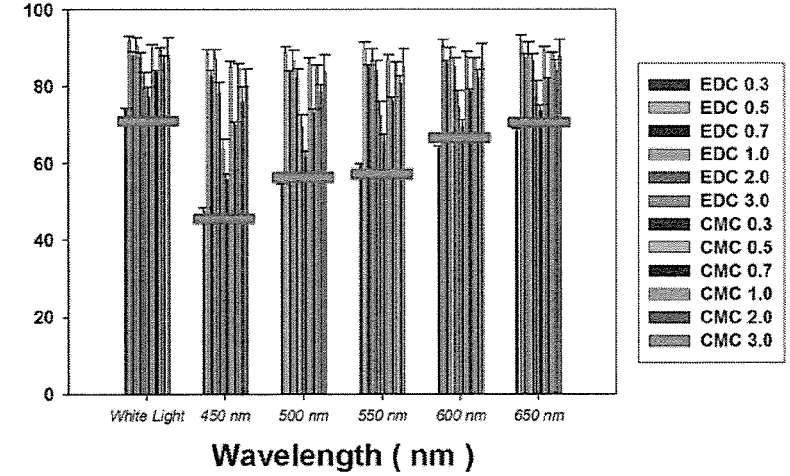
Figure 4:
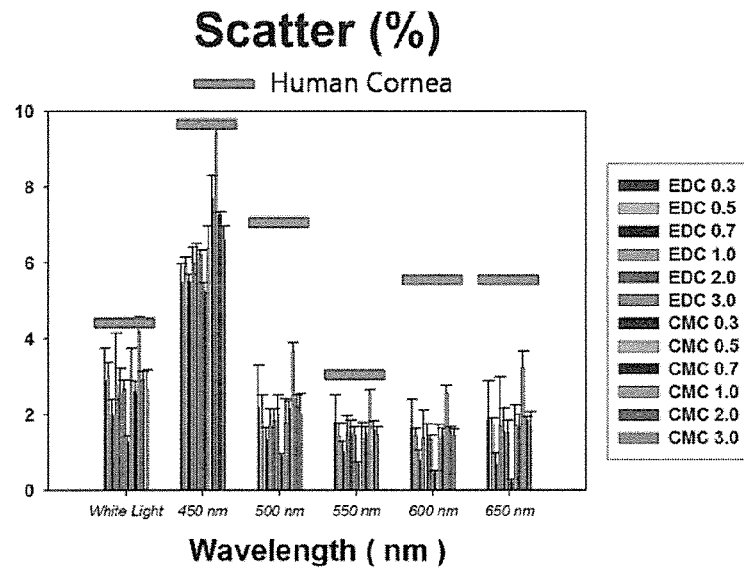
Figure 4:
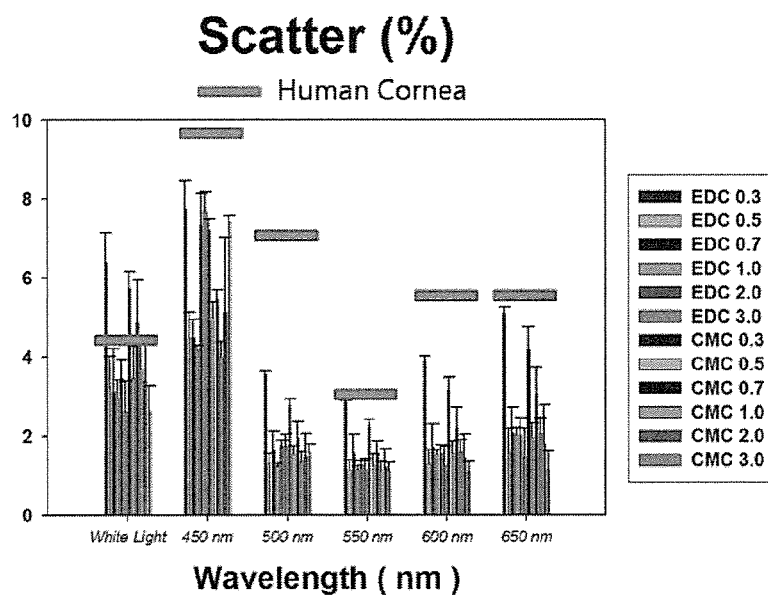

FIG. 4 depicts white light transmission (A and B) and backscatter (C and D) of collagen hydrogels prepared using Method A (A and C) and Method B (B and D). White light transmission of EDC crosslinked collagen hydrogels made by Method A was found to be higher than that of the CMC crosslinked collagen hydrogels made by Method A at all wavelengths. The CMC crosslinked collagen hydrogel was very soft, thick and transparent when the molar equivalent was 1.0 and less; however, the CMC crosslinked collagen hydrogels had high water contents which strongly effect the transmission of collagen hydrogel.

White light transmission of EDC crosslinked collagen hydrogels made by Method B was similar to that of the CMC crosslinked collagen hyrdogels made by Method B at all wavelengths. CMC crosslinked collagen hydrogels with molar equivalent 1.0 and less are typically thin and strong, which may contribute to the transmission properties.

White light transmission of EDC crosslinked collagen hydrogels made by Method A was similar to those of the EDC crosslinked collagen hydrogels made by method B in all wavelengths. The white light transmission of CMC crosslinked collagen hydrogels made by Method A was similar to that of the CMC crosslinked collagen hyrdogels made by Method B when molar equivalent was 2 or 3. However, when the molar equivalent was from 0.3 to 1, the white light transmission of CMC crosslinked collagen hydrogel made by Method B was higher than those made by Method A. It was noticed that CMC crosslinked collagen hydrogels made by Method A were thick and soft, while those by Method B were thin and strong. The high water contents and cloudy hydrogels may contribute to interference with the light transmission of the hydrogel. The white light transmission of all collagen hydrogels was superior to that of human cornea at all wavelengths.

The backscatter values of EDC crosslinked collagen hydrogels made by Method A was lower than that of the CMC crosslinked collagen hydrogels prepared by Method A. The backscatter values of EDC crosslinked collagen hydrogels made by Method B was similar to that of the CMC crosslinked collagen hydrogels prepared by Method B. The backscatter values of EDC crosslinked collagen hydrogels made by Method A was lower than that of the EDC crosslinked hydrogels prepared by Method B. The backscatter values of CMC crosslinked collagen hydrogels made by Method A was similar to that of the CMC crosslinked hydrogels prepared by Method B. The backscatter values of all EDC crosslinked hydrogels made by Method A were superior to those of the CMC crosslinked hydrogels made by Method A and Method B and the EDC crosslinked hydrogels made by Method B. The values of backscatter had a similar tendency to those of transmission of collagen hydrogels.

C. Thermal Analysis (DSC)

Figure 5:
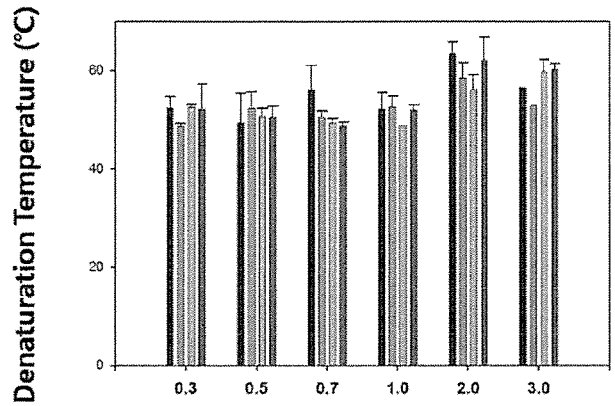
FIG. 5 graphically depicts the denaturation temperature (A) and the enthalpy change (B) observed using collagen hydrogels prepared using EDC or CMC as a crosslinker.
Figure 5:
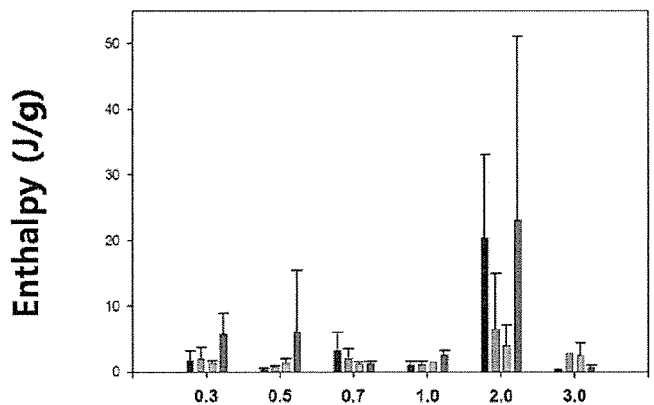

FIG. 5 depicts the denaturation temperature (A) and the enthalpy change (B) observed using collagen hydrogels prepared using EDC or CMC as a crosslinker. The denaturation temperature (Td) of EDC and CMC crosslinked collagen hydrogels had a tendency to increase as the molar equivalent of the collagen hydrogel was increased. The denaturation temperature and the enthalpy of collagen hydrogel at molar equivalent 2.0 were the highest in all of the collagen hydrogels. The Td of EDC and CMC crosslinked collagen hydrogels at molar equivalent 2.0 was the most increased to about 26.5° C. and 25° C. from 37° C. respectively. The highest values of ΔHd for collagen hydrogels was at molar equivalent 2.0 in all the collagen hydrogels. The tensile strength of collagen hydrogel at molar equivalent 2.0 was the highest for all collagen hydrogels tested.

D. In vitro Collagenase Degradation

Figure 6:
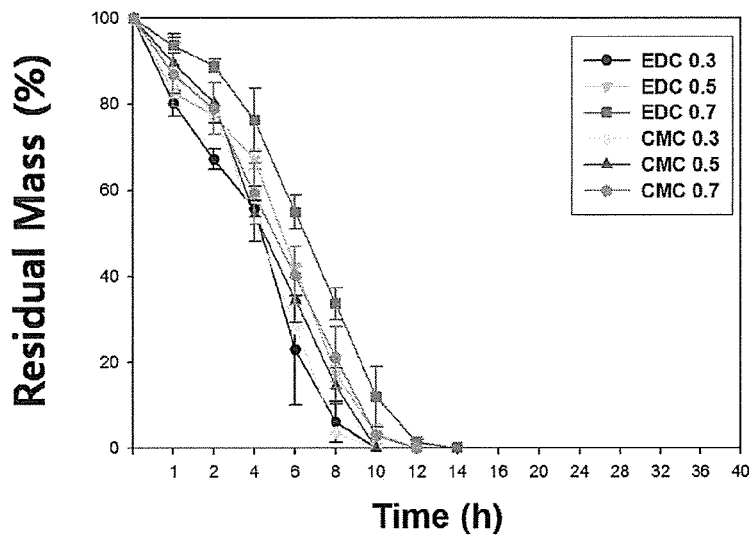
FIG. 6 graphically depicts in vitro biodegradation, as a measure of the relative stability of the hydrogel in vivo, collagen hydrogels prepared using EDC or CMC as a crosslinker. Error bars: standard deviation (n=3 samples for each point).
Figure 6:
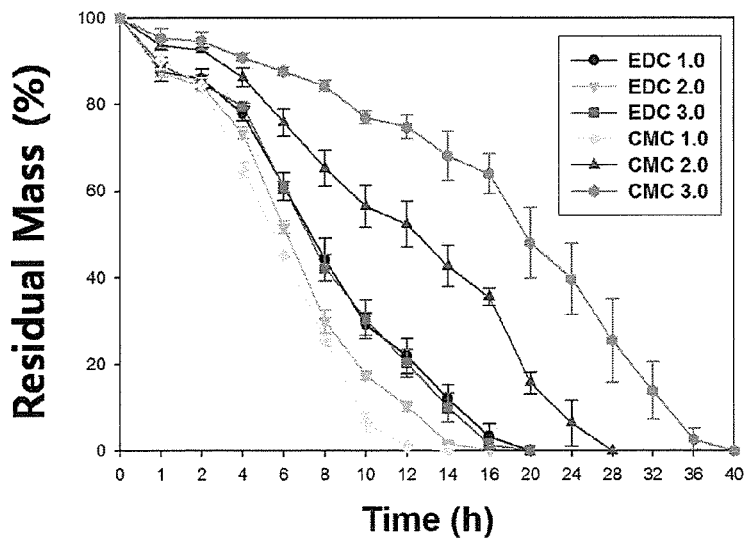

FIG. 6 depicts in vitro biodegradation, as a measure of the relative stability of the hydrogel in vivo, collagen hydrogels prepared using EDC or CMC as a crosslinker. Error bars: standard deviation (n=3 samples for each point). The residence mass of the EDC crosslinked collagen hydrogels was superior to those of the CMC crosslinked hydrogels when the molar equivalent was equal or less than 1. However, when the molar equivalent was higher than 1, the CMC crosslinked collagen hydrogel was much superior to those crosslinked by EDC. As a benchmark control, human corneas tested (see Ref. #1) take about 20 hours to completely degrade.

Figure 9:
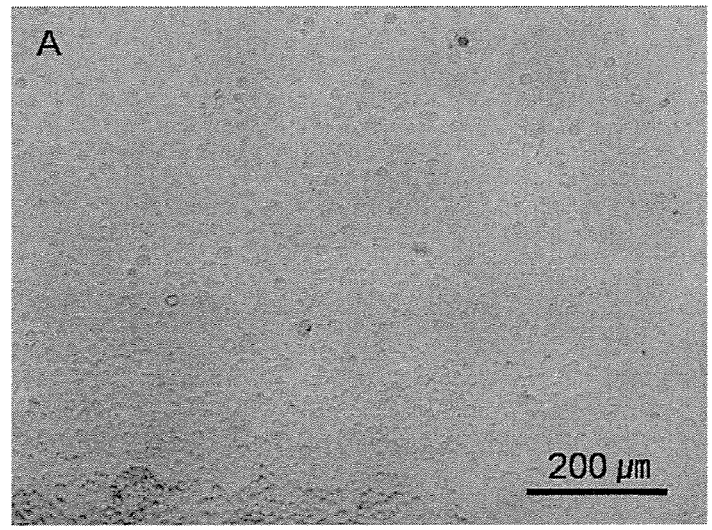
FIG. 9 depicts electron micrographs showing in vitro biocompatibility of a collagen hydrogel (CMC). The electron micrographs depict a collagen hydrogel confluent with corneal epithelial cells (A) and corneal endothelial cells (B) at day 12 postseeding. A: CMC-3.0, B: CMC-0.5.
Figure 9:
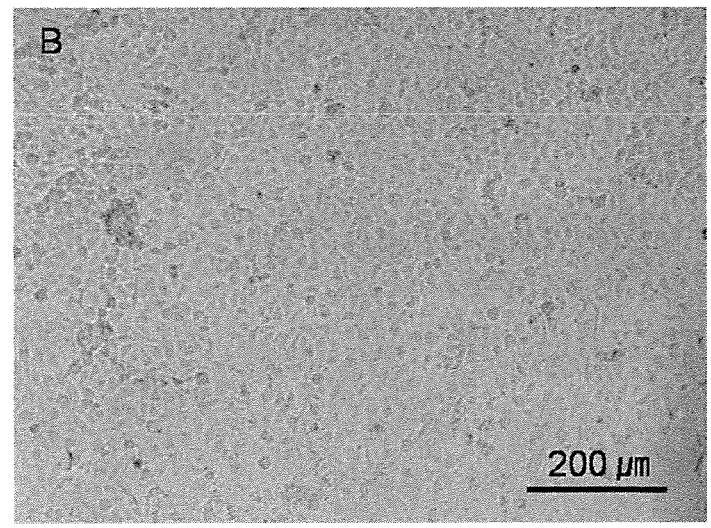

E. Culture of Corneal Epithelial and Endothelial cells cultured on collagen hydrogel FIG. 9 depicts electron micrographs showing in vitro biocompatibility of a collagen hydrogel (CMC). The electron micrographs depict a collagen hydrogel confluent with corneal epithelial cells (A) and corneal endothelial cells (B) at day 12 postseeding. A: CMC-3.0, B: CMC-0.5.

i) Culture of Corneal Epithelial Cells Cultured on Collagen Hydrogel

Figure 7:
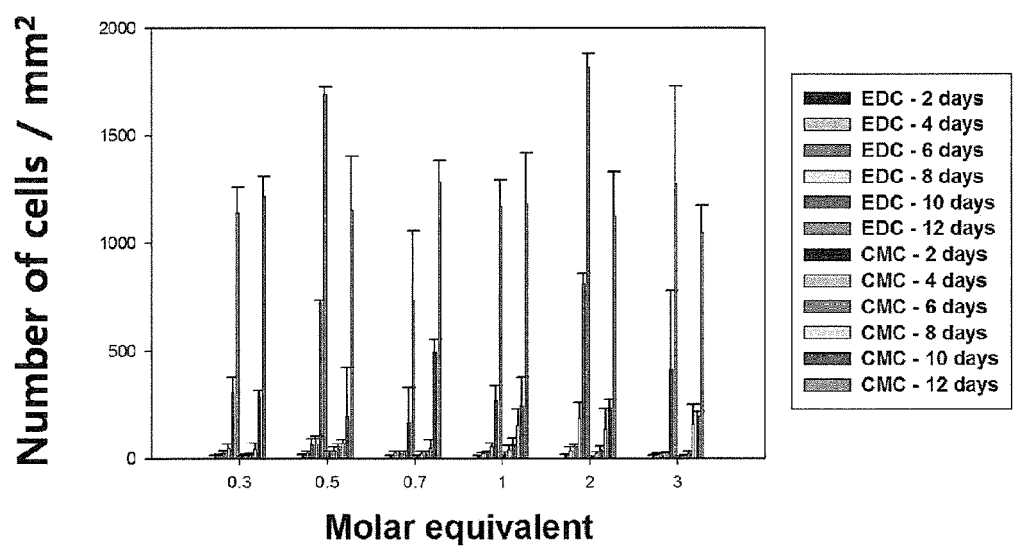
FIG. 7 graphically shows the total cell number of corneal epithelial cells cultured on collagen hydrogels (diameter 5 mm) prepared using EDC or CMC as a crosslinker.

FIG. 7 shows the total cell number of corneal epithelial cells cultured on collagen hydrogels (diameter 5 mm) prepared using EDC or CMC as a crosslinker. Total cell number of corneal epithelial cells cultured on EDC crosslinked collagen hydrogels was similar to that by CMC in all days. The corneal epithelial cells were confluent on every EDC and CMC crosslinked collagen hydrogel tested within 15 days after seeding. However, the collagen hydrogels that were the slowest to reach confluency, were those having a molar equivalent of crosslinker of 0.7. All collagen hydrogels tested successfully supported epithelial stratification in culture. It was confirmed that all collagen hydrogels could be used as a substrate for corneal epithelial cells. As shown in FIG. 9A, the corneal epithelial cells were confluent on all collagen hydrogel postseeding 15 days.

ii) Culture of Corneal Endothelial Cells Cultured on Collagen Hydrogel

Figure 8:
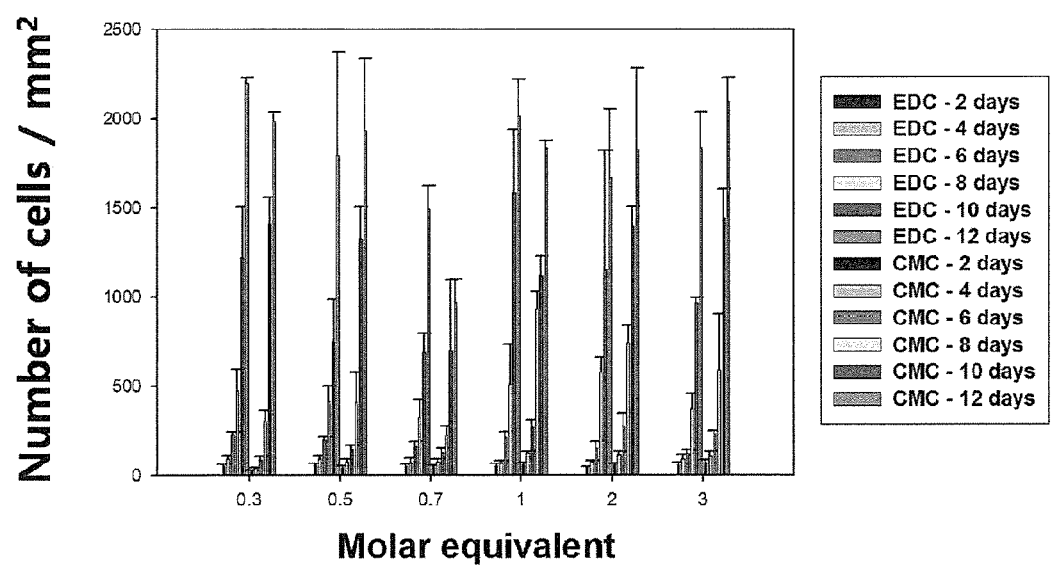
FIG. 8 graphically shows the total cell number of corneal endothelial cells cultured on collagen hydrogels (diameter 5 mm) prepared using EDC or CMC as a crosslinker.

FIG. 8 shows the total cell number of corneal endothelial cells cultured on collagen hydrogels (diameter 5 mm) prepared using EDC or CMC as a crosslinker. The corneal endothelial cells were generally well cultured on collagen hydrogel crosslinked with both EDC and CMC. When molar equivalent was 0.3, 0.7 and 1.0, the EDC crosslinked collagen hydrogel had a little more corneal endothelial cells cultured than the CMC crosslinked hydrogels. However, when the molar equivalent was 0.5, 2.0 and 3.0, the CMC crosslinked collagen hydrogels had a little more corneal endothelial cells cultured than the EDC crosslinked hydrogels. However, all collagen hydrogels could be used to successfully culture corneal endothelial cells. The collagen hydrogels that were slowest to reach confluency surface were those having a molar equivalent of crosslinker of 0.7, which is similar to the results above in relation to corneal epithelial cell culture. As shown in FIG. 9B, the corneal endothelial cells were confluent on all collagen hydrogel postseeding 12 days.

G. Culture of Neurites Cultured on (FIGS. 10 & 11)

Figure 10A:
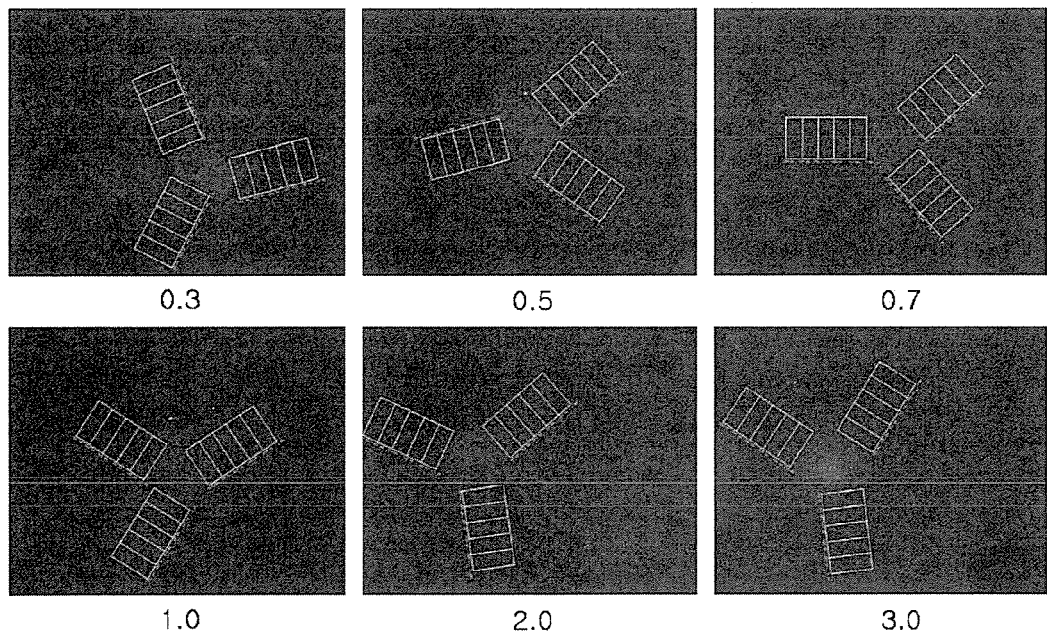
FIG. 10 are images depicting EDC (A) and CMC (B) crosslinked collagen hydrogel supported neurite extension.
Figure 10B:
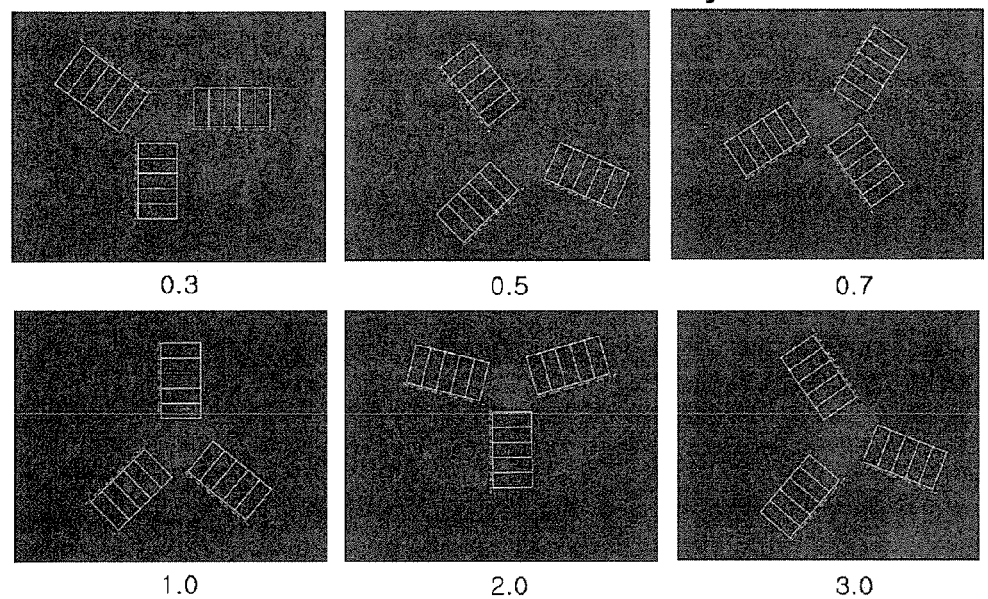
Figure 11:
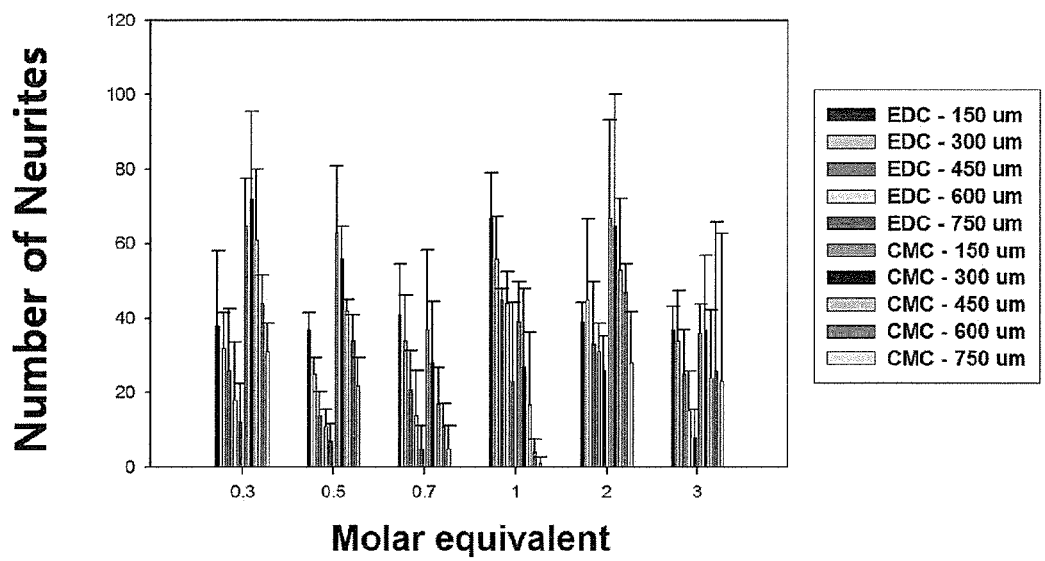
FIG. 11 graphically depicts the total cell number of neuritis from DRGs on collagen hydrogels (diameter 5 mm) prepared using EDC or CMC as a crosslinker.

FIG. 10 are images depicting (A) EDC and (B) CMC crosslinked collagen hydrogel supported neurite extension. Many neurites were successfully outgrown on the collagen hydrogels. The neurites were cultured on all collagen hydrogel crosslinked by CMC and EDC. The longest and highest density of neurites were observed on CMC 0.3 and EDC 1.0. The shortest and smallest density of neurites were observed on CMC 0.7 and EDC 0.5. Overall, the collagen hydrogel crosslinked by CMC was observed to be equivalent or slightly superior to the hydrogels crosslinked by EDC in terms of culturing of neurites.

It was observed that the tensile strength of collagen hydrogel can be changed by changing the order of component addition. When the crosslinker was CMC, the tensile strength of collagen hydrogel was significantly affected by the order of component addition. Particularly, it was found that the pH of the collagen solution at the time of crosslinker injection into the syringe was important in affecting the tensile strength of CMC crosslinked collagen hydrogels. The tensile strength of CMC crosslinked collagen hydrogels showed improvement by adding NaOH in the initial stage (Method B) in comparison to the addition of NaOH in the final stage (Method A). When EDC was used as the crosslinker, the tensile strength of the collagen hydrogel when the sodium hydroxide was in the initial step (Method B) was higher than when the NaOH was added in the last step (Method A) in almost molar equivalents, except 2.0 molar equivalent EDC. Therefore, it was found that the order of component addition order could significantly influence not only the mechanical properties of collagen hydrogels but also the physical properties (e.g., water content, refractive index). It was also found that the pH of the collagen solution could be more readily adjusted to 5.5 using Method A than Method B. While Method A has typically been used to make collagen hydrogels, Method B was found to be superior to Method A in making better and stronger collagen hydrogels.

When the molar equivalent of EDC crosslinked collagen hydrogel was 2 or 3, the tensile strength of the collagen hydrogel was slightly different when prepared by Method B and Method A. As the molar equivalent of EDC increases, the volume of NaOH used to make the collagen hydrogel decreases. When a molar equivalent of 2.0 or 3.0 of EDC was used to make collagen hydrogels, the mixing order appeared to be of little importance. However, when the molar equivalent was 0.3 or 0.5, mixing order had an effect on the hydrogel properties.

All mechanical properties of the tested hydrogels were lower than that of native human corneas (3.81±0.40) [11]. It is possible to overcome for this gap value if an effort is made to strengthen and culture corneal cells. Manipulation of corneal fibroblasts and collagen hydrogels to reconstruct corneal stroma before gelation may be required.

The component addition order may affect the pH of collagen solution. When crosslinker was injected in the syringe mixing system, the pH of collagen solution likely affects the properties of collagen hydrogel by controlling gelation speed of the crosslinking reaction. In other words, if the crosslinker (e.g., EDC, CMC) is added in the collagen solution when the pH of collagen solution was 5.5 (Method B), it is possible to crosslink in the whole collagen solution. Thus, when the molar equivalent of EDC was 0.3 and 0.5 and when the CMC was used to make collagen hydrogel, the tensile strength of collagen hydrogel made by Method B was stronger than that made by Method A. However, when the molar equivalent of EDC was from 0.7 to 3.0, the tensile strength of each collagen hydrogel was similar. This may be caused because the collagen had enough EDC to crosslink. Although the molar equivalent of CMC was high, there was a big difference in tensile strength of hydrogels prepared according to Method A and Method B. While not wishing to be bound by theory, this was likely because the CMC has a cyclohexyl group and the cyclohexyl group interrupted formation of crosslinking bond though enough CMC was used in Method A. In the case of hydrogels prepared by Method B, it was thought that the effect of pH was superior to that of steric hindrance.

If the sodium hydroxide is added in the collagen solution to adjust the pH 5.5 of collagen solution, it is possible to locally crosslink part of the collagen solution. EDC was found to raise the pH of the collagen solution. When the molar equivalent of EDC was 0.3 or 0.5, the effect of EDC on pH was noticeable, as it strengthened the hydrogels. However, when the molar equivalent of EDC was from 0.7 to 3.0, the EDC had such a significant effect on the pH of collagen solution that there was no difference in tensile strength in hydrogels prepared according to Method A and B.

The gelation times of EDC and CMC crosslinked collagen hydrogels were similar as shown Table 2. When CMC crosslinked collagen hydrogel was prepared using a method including mixing 100 more times than the method used for the EDC crosslinked hydrogels, a longer gelation time for the CMC crosslinked hydrogel than for the EDC crosslinked hydrogel was observed. More than 100 times mixing was required in the syringe system using CMC to react the collagen and CMC sufficiently. This additional mixing is sufficient time to permit effective mixture of corneal fibroblasts in the collagen solution.

The results of the corneal epithelial cell cultures demonstrated that all the collagen hydrogels crosslinked by EDC and CMC provided an appropriate substrate for growth of corneal epithelial cells. However, CMC provides a longer gelation time over EDC, which allows for flexibility in manipulation time to construct a hydrogel containing cells. The CMC crosslinked hydrogels also have superior mechanical properties over those of EDC. At higher molar concentrations of this crosslinker, the gels are more resistant to collagenase degradation. However, these CMC-crosslinked hydrogels are comparable to EDC crosslinked hydrogels in optical and water retention properties, as well as biocompatibility and ability to support growth of corneal epithelial cells.

Thus, CMC demonstrates advantageous properties over EDC as a crosslinker. CMC can be used to crosslink a biopolymer such as collagen at room temperature and provides a longer gelation time for fabricating the hydrogel. As such, CMC was shown as a crosslinking agent of collagen hydrogel to reconstruct bioartificial stroma. Thus, the use of CMC rather than EDC as a crosslinker can allow for easier manufacturing in scale-up for clinical applications.

Example 2

CMC Crosslinked Type III Collagen Hydrogels

A series of collagen hydrogels was prepared using the methods set out above in Example 1 and as described in the applicant's previous patent applications International PCT Publication Nos. WO 2006/015490 and WO 2007/028258, both of which are incorporated herein in their entirety. In each case, where EDC was previously used as the crosslinker it was replaced with the CMC crosslinker.

The fabricated hydrogels included the following components:
  13.7% type III collagen+1.0 CMC molar equivalent
  13.7% type III collagen+0.4 CMC molar equivalent
  13.7% type III collagen+0.4 CMC molar equivalent+ MPC (2-methacryloyloxyethyl phosphorylcholine)+ PEG (MES) (polyethylene glycol (morpholinoethanesulfonic acid))
  13.7% type III collagen+0.4 CMC molar equivalent+ MPC+PEG (water)
  18% type III collagen+0.4 CMC molar equivalent
  18% type III collagen+0.4 CMC molar equivalent+MPC+ PEG (water)

In the case of MPC and PEG containing hydrogels, PEG-DA was used as monomer to crosslink MPC and Irgacure 2959 was used as a photoinitiator during curing using a UV photoreactor to form a hydrogel network. Other water soluble photoinitiators in UV or visible region could be also used.

Figure 12:
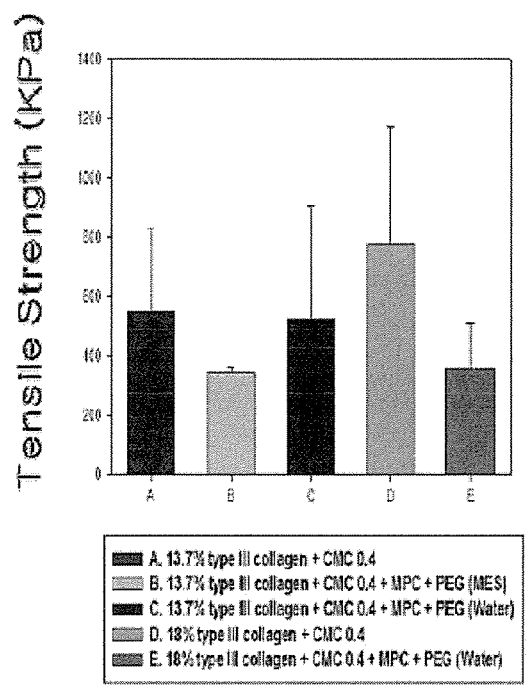
FIG. 12 graphically depicts the comparison of mechanical properties of type III CMC crosslinked type III collagen hydrogels. (A) Tensile strength, (B) Elongation break, (C) Modulus, (D) Toughness. Error bars; standard deviation (n=3 samples for each data point).
Figure 12:
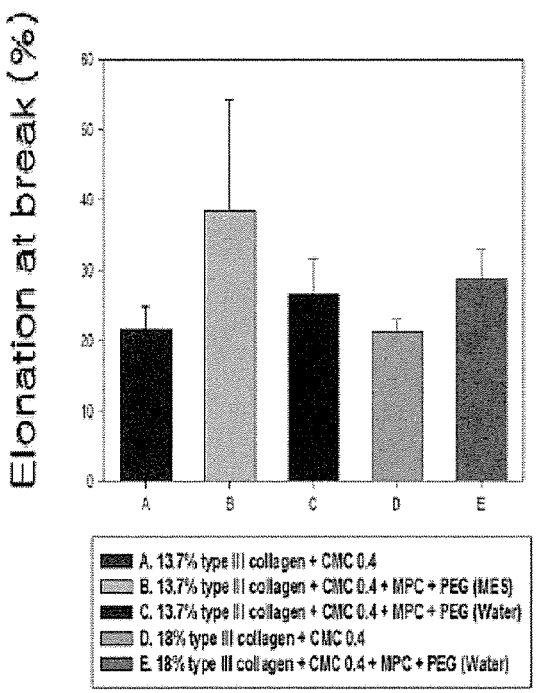
Figure 12:
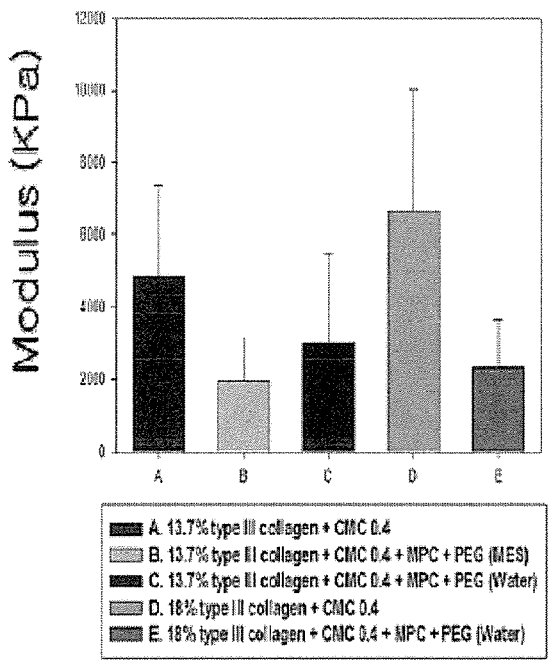
Figure 12:
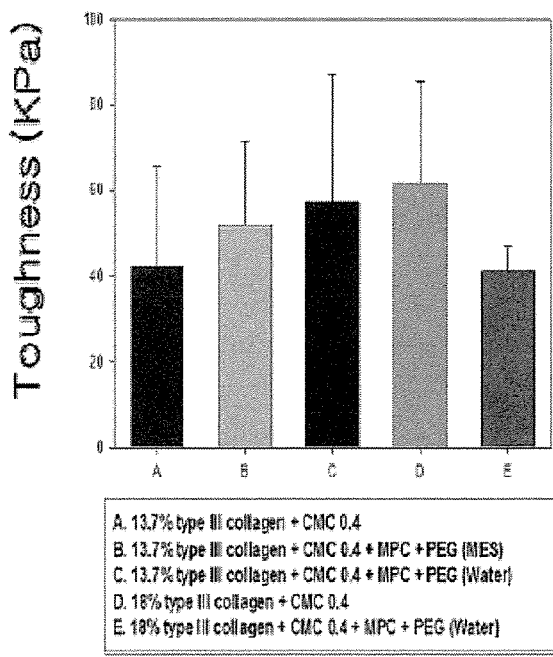
Figure 13:
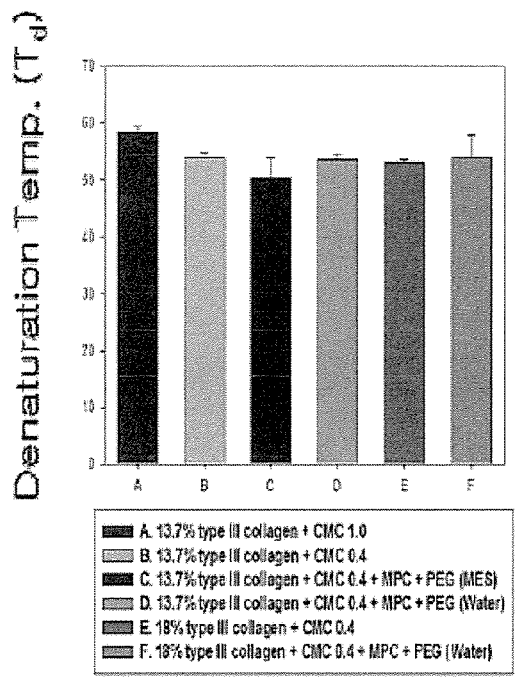
FIG. 13 graphically depicts the denaturation temperature (A) and the enthalpy change (B) observed using CMC crosslinked type III collagen hydrogels.
Figure 13:
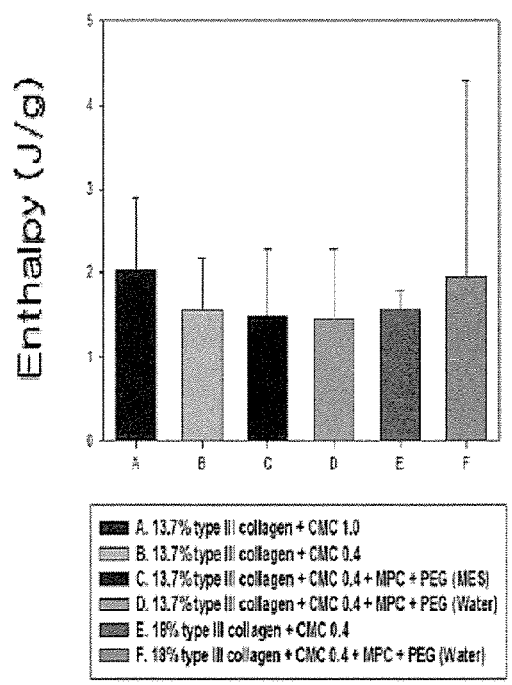

The physical and mechanical properties of the resulting hydrogels were tested according to the methods set out in Example 1. The results of the testing are provided in FIGS. 12 and 13, FIG. 12 depicts the comparison of mechanical properties of type III CMC crosslinked type III collagen hydrogels. (A) Tensile strength, (B) Elongation break, (C) Modulus, (D) Toughness. Error bars; standard deviation (n=3 samples for each data point). FIG. 13 depicts the denaturation temperature (A) and the enthalpy change (B) observed using CMC crosslinked type III collagen hydrogels.

The composite hydrogels made using Type III collagen+ CMC 0.4+MPC, were successfully used for incorporation of silica nanoparticle encapsulated acyclovir within the hydrogel.

Example 3

CMC Crosslinked Collagen Hydrogels for Corneal Substitutes

In this example, an evaluation and comparison of mechanical and optical properties and in vitro biocompatibility of collagen hydrogel cross-linked with 1-ethyl-3-(3-dimethyl aminopropyl) carbodiimide hydrochloride (EDC) and the sterically bulky N-Cyclohexyl-N'-(2-morpholinoethyl) carbodiimide metho-p-toluenesulfonate (CMC) in combination with N-hydroxysuccinimide (NHS) was conducted. Various molar equivalents of carbodiimide cross-linkers were studied to determine the optimal conditions in the fabrication of collagen hydrogels. Collagen hydrogels were composed of 10% porcine type I collagen cross-linked with EDC and NHS or CMC and NHS. Various measurements such as tensile strength, water contents, optical properties and thermal analysis were carried out on the collagen hydrogels. In addition, immortalized corneal epithelial cells, corneal endothelial cells and nerve cells from chicken embryo were cultured on the collagen hydrogels to test biocompatibility.

Materials

Freeze-dried porcine Type I collagen was purchased from Nippon Meat Packers Inc. (Tokyo, Japan). Morpholinoethanesulfonic acid (MES; EMD Chemicals Inc., USA) was dissolved in deionized water to form a 0.625 M MES buffer solution. 1-Ethyl-3-(3-dimethyl aminopropyl) carbodiimide hydrochloride (EDC) and N-Cyclohexyl-N'-(2-morpholinoethyl) carbodiimide metho-p-toluenesulfonate (CMC) and collagenase (type I *Clostridium histolyticum*, EC 3.4.24.3) were supplied by Sigma-Aldrich Canada Ltd (Oakville, Ontario, Canada). N-hydroxysuccinimide (NHS) was supplied by Fluka (Buchs, Switzerland). Phosphate buffered saline (PBS, pH=7.4) was prepared from the tablet form (Calbiochem Corp., Darmstadt, Germany). 2 N NaOH solution was prepared by dissolving sodium hydroxide pellets (EMD Chemicals Inc. Germany) in deionized water. Milli-Q deionized water (Millipore, Billerica, Md.) was used throughout. All other reagents were of analytical grade.

Preparation of Collagen Solution

Porcine collagen solution (10% w/w) was prepared by dissolving freeze-dried porcine collagen in water at 4° C. stirring with an electric-powered stirring shaft for 2 days. The resulting collagen solution was then transferred into a plastic syringe equipped with a syringe stopper, and centrifuged at 4° C. to completely remove the trapped air bubbles to give a clear, viscous solution ready for use.

Preparation of Collagen Hydrogel

Table 4 summarizes the fabrication protocol of collagen hydrogels. The table shows the mixing time and temperature of the mixing system when the collagen hydrogel is made. One difference of the fabrication protocol of collagen hydrogel crosslinked with between EDC and CMC was the mixing temperature when the crosslinker added and mixed. The temperature of syringe mixing system was increased at 25° C. in advance of adding CMC to confirm that the collagen hydrogel could be crosslinked with CMC at room temperature. However, in the case of EDC, the EDC was added into mixing system and then mixed at 0° C. 2N NaOH was added to the collagen solution immediately following the addition of MES buffer prior to addition of the cross-linker to bring up the pH around 5.

TABLE 4

Fabrication protocol of collagen hydrogel

| Order | EDC | Mixing times | Mixing Temp. (° C.) | CMC | Mixing times | Mixing Temp. (° C.) |
|---|---|---|---|---|---|---|
| 1 | Collagen + MES | 60 | 0 | Collagen + MES | 60 | 0 |
| 2 | +NaOH | 150 | 0 | +NaOH | 150 | 0 |
| 3 | +NHS | 100 | 0 | +NHS | 100 | 0 |
| 4 | +EDC | 60 | 0 | Wait - 10 min. | | 25 |
| 5 | Cast | | | +CMC | 60 | 25 |
| 6 | | | | Cast | | |

Collagen Hydrogel Cross-linked with 0.3 Molar Equivalent of EDC at 0° C.

Briefly, 600 mg of 10% w/w bubble-free collagen solution was thoroughly mixed with 150 μl of MES (0.625 M) buffer in a syringe mixing system under an ice-water bath [20]. Then 18 μl of 2 N NaOH was added to adjust the pH of the mixture to around 5, followed by addition of 0.79 mg of NHS and 1.31 mg EDC (EDC:Collagen-$NH_2$=0.3:1 molar equivalent; EDC:NHS=1:1 molar equivalent), respectively. After thorough mixing, the mixture was cast into curved plastic molds (thickness: 500 μm; diameter: 12 mm) or between two pieces of glass plates (10 cm×10 cm×0.25 cm) separated by a spacer with a thickness of 430 p.m. The molds were left at room temperature with 100% humidity for 16 h, and then transferred into an incubator for post-curing at 37° C. for 5 h. After incubation, the molds were immersed in 10 mM PBS for 30 min, followed by careful demolding of the hydrogels. The resulting hydrogels, curved or flat, were washed by immersion in PBS, refreshing the solution at 8 h intervals for 2 days. The hydrogels were then immersed in 10 mM PBS containing 1% chloroform to maintain sterility and stored at 4° C.

Collagen Hydrogel Cross-linked with 2.0 Molar Equivalent CMC at Room Temperature 15 μl, of 2 N NaOH, was injected into the mixture of 600 mg of 10% w/w collagen and 0.15 ml 0.625 M MES buffer, followed by injection of 5.25 mg of NHS. Then the syringe mixing system was immersed in 25° C. water bath for 10 minutes, followed by injection of 19.3 mg CMC (CMC:Collagen-$NH_2$=2.0:1 molar equivalent; CMC:NHS-1:1 molar equivalent). The procedure continued as shown above. Hydrogels with all other molar equivalent ratios of EDC or CMC to collagen-$NH_2$ were prepared in the same fashion.

Collagen Hydrogel Cross-linked with 0.3 Molar Equivalent EDC at Room Temperature 18 μl of 2 N NaOH, was injected into the mixture of 600 mg of 10% w/w collagen and 0.15 ml 0.625 M MES buffer, followed by injection of 0.79 mg of NHS. Then the syringe mixing system was immersed in 25° C. water bath for 10 minutes, followed by injection of 1.31 mg EDC (EDC:Collagen-$NH_2$=0.3:1 molar equivalent; EDC:NHS=1:1 molar equivalent). The procedure continued as shown above. The collagen hydrogels cross-linked with EDC at room temperature were used in measuring gelation time only.

Mechanical Properties

The mechanical properties of the hydrogels were measured using an Instron electromechanical universal tester (Model 3342, Instron, Canton, Mass.) equipped with Series IX/S software. Flat hydrogels, 0.43 mm thick, were equilibrated in PBS and cut into 12 mm×5 mm rectangular strips. The actual gauge length of each specimen was 5 mm for testing. Three specimens were measured for each hydrogel formulation. The crosshead speed was 10 mm/min.

Optical Properties

Refractive indices of flat and fully hydrated hydrogels equilibrated in PBS were recorded using an Abbe refractometer (Model C10, VEE GEE Scientific Inc., Kirkland, Wash.) at 21° C. with bromonaphthalene as the calibration agent. Hydrogel light transmission and back-scattering measurements were carried out at 21° C. on a custom-built instrument described previously [6]. Differences in the optical properties between CMC and EDC cross-linking hydrogels were analyzed statistically using a one-way analysis of variance (ANOVA). All comparisons were a priori, pre-specified analyses using Tukey-Kramer to correct for multiple testing. Statistical significance was set at $P<0.05$.

Water Contents

After equilibrating in PBS for 2 days at 4° C., the hydrogels were gently blotted with a filter paper to remove surface water, and then immediately weighed on a microbalance to record the wet weight of the sample. The hydrogels were then dried under vacuum at room temperature to constant weight. The total equilibrated water content of hydrogels ($W_t$) was calculated according to equation: $W_t=(W-W_0)/W \times 100\%$, where W and $W_0$ denote the wet weight and the dry weight of the samples, respectively.

Thermal Analysis

The thermal properties of collagen solutions and collagen hydrogels were examined on a differential scanning calorimeter (DSC-2C, thermal specialty Corporation). Heating scans were recorded in the range of 8-80° C. at a scan rate of 5° C./min 5 to 10 mg pre-weighed samples of collagen solution or PBS-equilibrated collagen hydrogels were surface-dried with filter paper and hermetically sealed in aluminum pans to prevent water evaporation. PBS was used as a blank reference. The denaturing temperature ($T_d$) at the maximum of the endothermic peak and enthalpy ($\Delta H_d$) were measured.

In vitro Collagenase Biodegradation 50 to 80 mg of hydrogels were equilibrated for 1 h in 5 ml 0.1M tris-HCl buffer (pH 7.4) containing 5 mM $CaCl_2$ at 37° C. Subsequently, 1 mg/ml (288 U/ml) collagenase solution was added to give a final collagenase concentration of 5 U/ml. The solution was replaced every eight hours to retain enough activity of collagenase. At different time intervals, the hydrogels were weighed after the surface water was gently blotted off. Three samples were tested for each hydrogel formulation. The percent residual mass of hydrogels was calculated according to the following equation: residual mass $\% = W_t/W_0$, where $W_o$ is the initial weight of the hydrogel and $W_t$ is the weight of the hydrogel at each time point.

In vitro Cell Compatibility
Corneal Epithelial Cells

Two Teflon rings (Bioland Ltd., Korea, diameter: 5 mm) were used to culture immortalized human corneal epithelial cells on collagen hydrogel. 150 corneal epithelial cells (8 cells/mm$^2$) were seeded on the collagen hydrogel. Three pictures were taken to count cells at every 2 days. A serum-free medium containing epidermal growth factor (Keratinocyte Serum-Free Medium (KSFM), Life Technologies, Burlington, Canada) was used for cell culture and was changed every two days after taking pictures.

Corneal Endothelial Cells

The Teflon ring was used to culture immortalized human corneal endothelial cells on collagen hydrogel. 2000 corneal endothelial cells (100 cells/mm$^2$) were seeded on the collagen hydrogel. 3 pictures were taken to count cells at every 2 days. The medium was supplemented with a serum-free medium (Opti-MEM) containing FBS (8%), Ascorbic acid (20 mg/L), Human lipid mixture (50 μl/L), Chondroitin sulphate C (0.8 g/L), Calcium chloride (0.2 g/L), Gentamycin (0.5%), RPMI-multiple vitamin solution (1%), Antibiotic Antimycotic solution (1%), EDTA (0.2 g/L), FGF (25 mg/L), EGF (2.5 mg/L) and NGF (0.1 g/L), changed every two days after taking pictures.

Nerve Cells

To determine the ability of the hydrogels to support nerve surface growth, dorsal root ganglia (DRG) from chick embryos (E 8.0) were dipped into collagen matrix as an adhesive, and adhered to the surface of washed gel pieces. The medium was supplemented with a serum-free medium (KSFM) containing B27 (2%), N2 (1%) and Retinoic acid (5 μM). Neurite growth was observed for up to a total of 6 days, after which the gels were fixed in 4% paraformaldehyde in 0.1 M PBS, pH 7.2-7.4 and stained for the presence of neurofilament using mouse anti-NF200 antibody overnight at 4° C. Neurofilament was visualized the following day using donkey antimouse-Cy2 secondary antibody. Whole mounts were imaged using a Zeiss Axiovert microscope. The number of neurites was counted reaching 150, 300, 450, 600, and 750 μm per 0.8775 mm$^2$ area after 6 days of attachment on collagen hydrogel.

Results
Gelation Time

The gelation time was measured every 1 minute. The higher the molar equivalent of crosslinker was, the quicker the gelation time of collagen hydrogel was. When the molar equivalent of crosslinker was same, CMC had about 2 minutes longer gelation time than EDC though the collagen hydrogel crosslinked with CMC was made at room temperature. In addition, the gelation time of collagen hydrogel cross-linked with EDC in the room temperature condition was quicker than at 0° C. (Table 5). Therefore, CMC is advantageous as it may cross-link at room temperature and provides longer gelation time.

TABLE 5

Gelation time of collagen hydrogel cross-linked with EDC and CMC (minutes)

| Cross-linker | Cross-linking Temp. (° C.) | Molar equivalent of Cross-linker | | | | | |
|---|---|---|---|---|---|---|---|
| | | 0.3 | 0.5 | 0.7 | 1.0 | 2.0 | 3.0 |
| EDC | 0 | 7-8 | 6 | 5 | 4 | 2-3 | 1-2 |
| CMC | 25 | 10 | 8 | 7 | 7 | 4 | 2-3 |
| EDC | 25 | 4 | 2 | N/A | N/A | N/A | N/A |

Mechanical Properties

Figure 15:
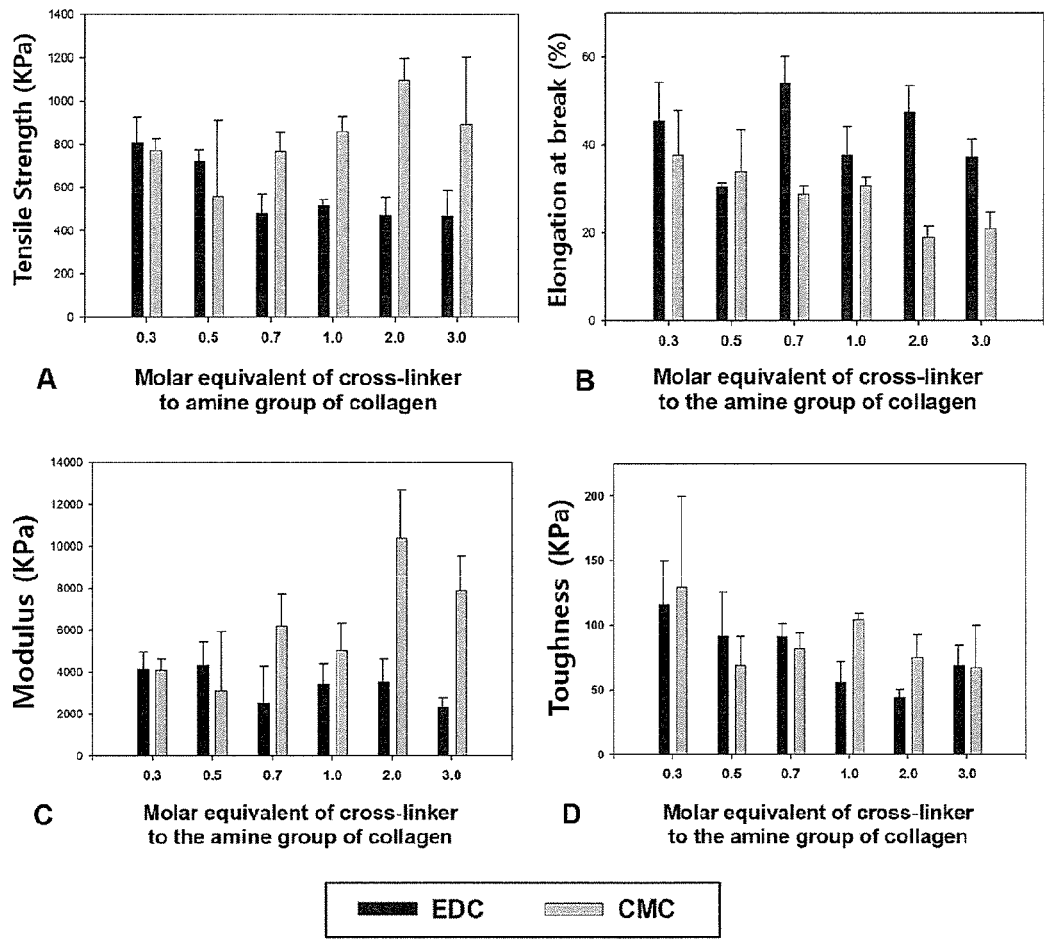
FIG. 15 graphically depicts a comparison of mechanical properties of collagen hydrogels cross-linked with either EDC or CMC.

The tensile strength, elongation at break, elastic moduli and toughness of type I porcine collagen hydrogels at different EDC/Coll-NR, and CMC/Coll-NH$_2$ ratios are shown in FIG. 15. The tensile strength of collagen hydrogel cross-linked with EDC was higher than those cross-linked with CMC when the molar equivalent of cross-linker was 0.3 or 0.5. However, the tensile strength of collagen hydrogel cross-linked with CMC was higher when the molar equivalent of cross-linker increased from 0.7 to 3.0. The highest tensile strength values for collagen hydrogels cross-linked with both CMC and EDC occurred at concentration ratios of 2.0 and 0.3 to available amine group content respectively. The value of elongation at break of all collagen hydrogels lied between 20% and 60% with similar molar equivalent values. The modulus and toughness of all collagen hydrogel materials followed a similar trend to that of tensile strength at various molar equivalents. The tensile strength and modulus of the CMC cross-linked hydrogels were approximately 1.5-2 times higher than that of cross-linked EDC hydrogels when the molar equivalent was higher than 0.5. However, no observable difference was made for the toughness of both types of hydrogels.

Water Content of Collagen Hydrogel

Figure 16:
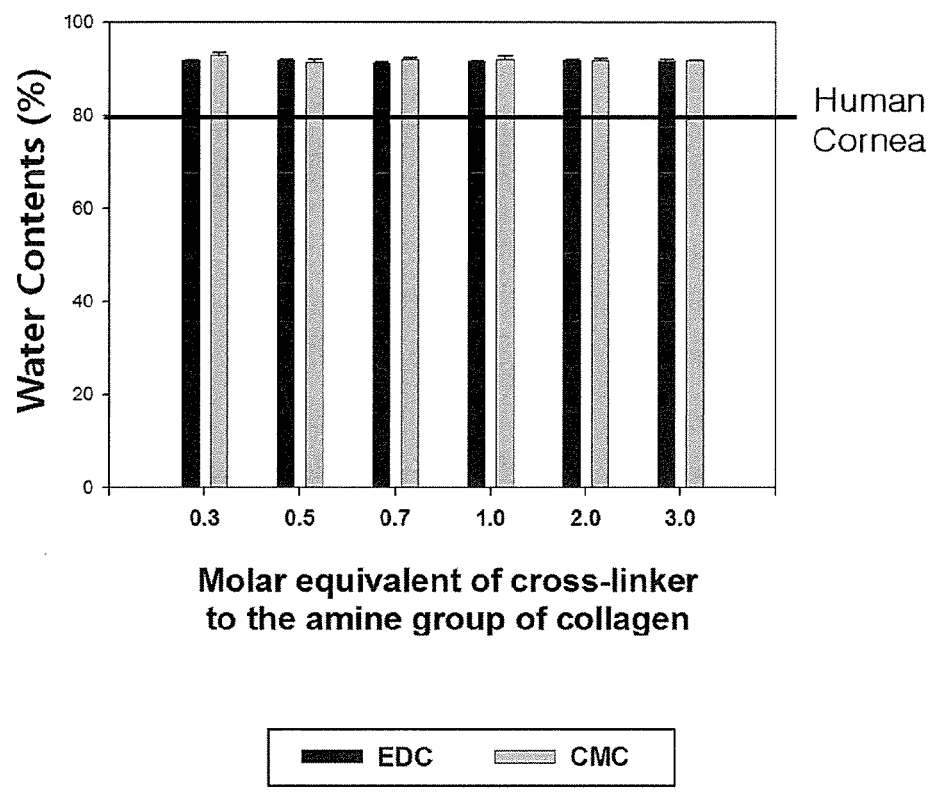
FIG. 16 illustrates water contents of collagen hydrogels tested.

As shown in FIG. 16, the water content of all collagen hydrogels crosslinked with both EDC and CMC were between 91% and 93%. These values are higher than the water contents of the human cornea (21).

Physical Properties of Collagen Hydrogel

Refractive Index

Figure 17:
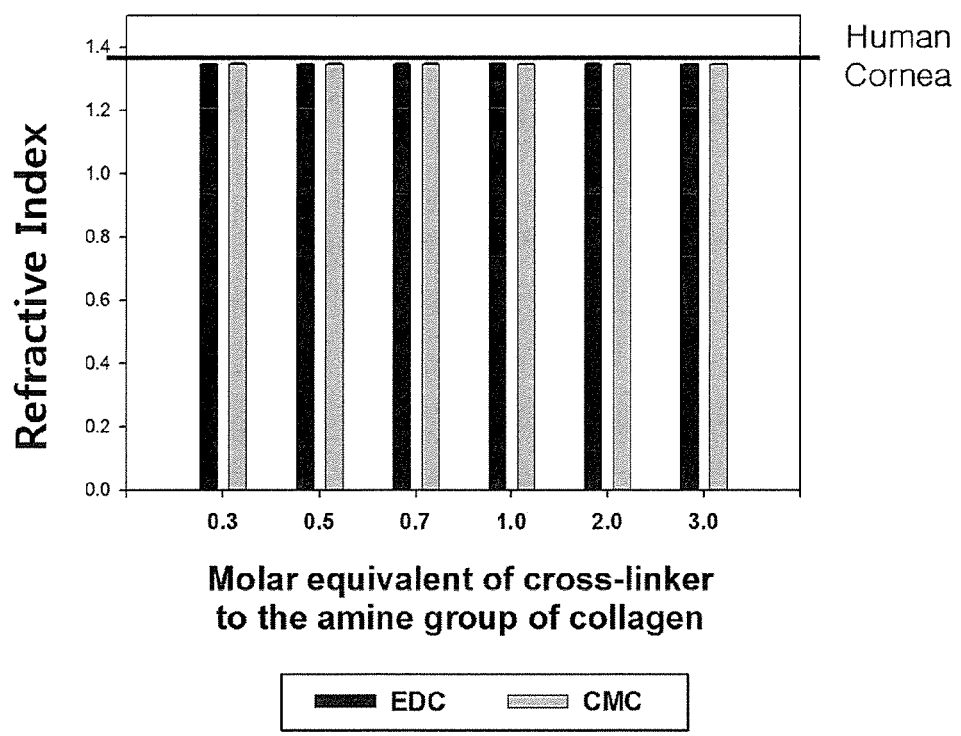
FIG. 17 illustrates refractive indexes of collagen hydrogels tested.

As shown in FIG. 17, the refractive index of collagen hydrogel cross-linked with EDC was similar to that cross-linked with CMC at each molar equivalent. Further, the refractive indexes of all collagen hydrogels were similar to that of human cornea (22).

Optical Properties

Figure 18:
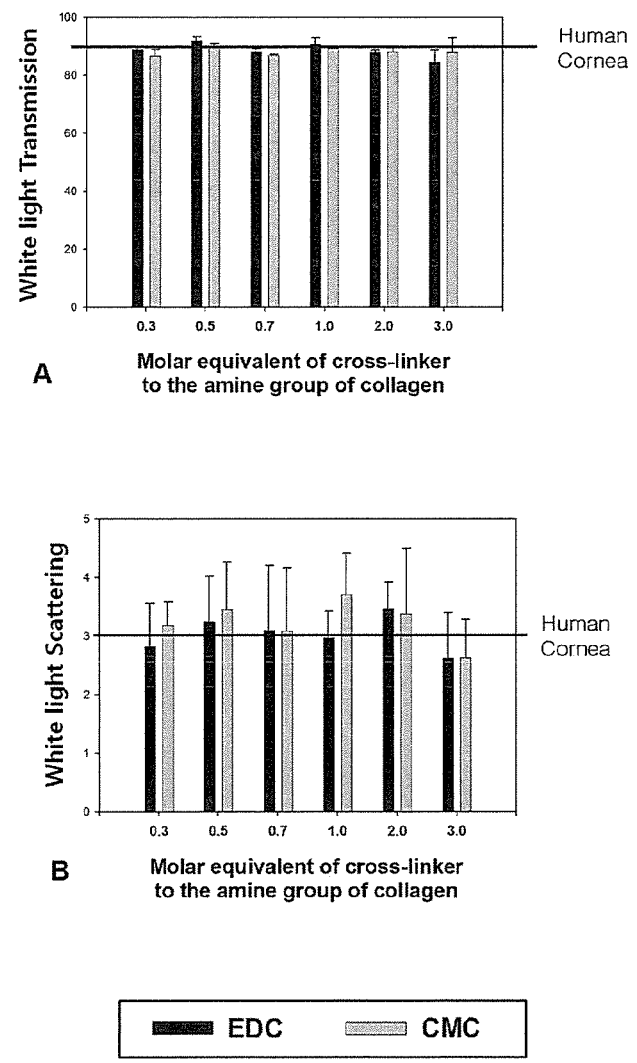
FIG. 18 illustrates white light transmission measurements in collagen hydrogels tested.

FIG. 18 illustrates white light transmission (A) and white light scattering (B). The white light transmission of collagen hydrogels cross-linked with EDC was similar to that cross-linked with CMC in all molar equivalents (FIG. 18A). Further, the white light transmission values of all collagen hydrogel were similar to that of human cornea (23). The values of backscatter had a similar tendency to the transmission in collagen hydrogels. All optical properties of collagen hydrogel were very similar to that of the human cornea in that they were all optically clear. Therefore the optical properties of all collagen hydrogels prepared herein were comparable to that of the human cornea.

Thermal Analysis (DSC)

Figure 19:
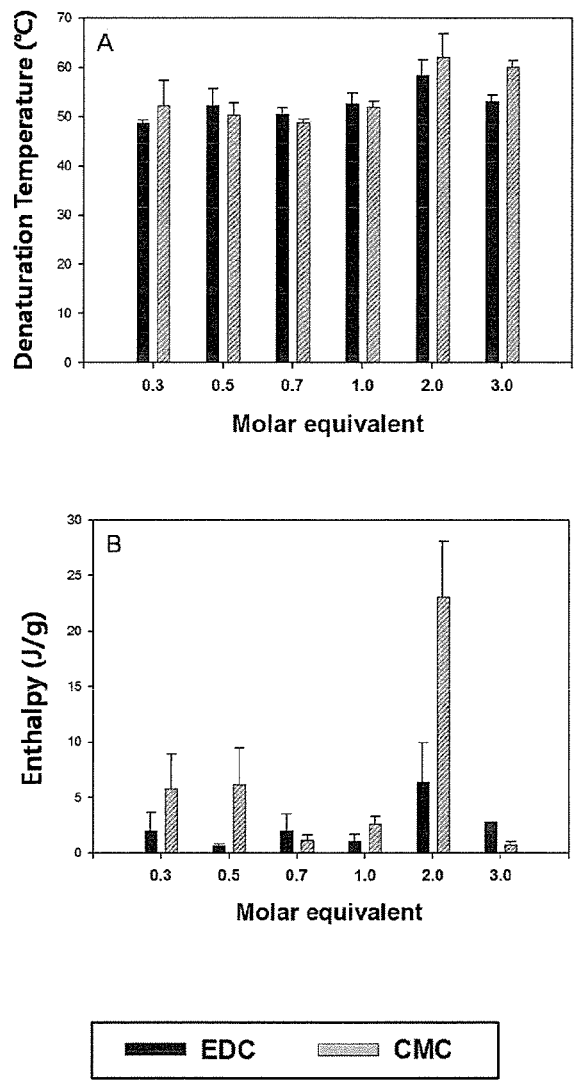
FIG. 19 illustrates denaturation temperature (A) and the enthalpy (B) in collagen hydrogels tested.

FIG. 19 illustrates (A) denaturing temperature and (B) enthalpy change. The denaturation temperature of collagen hydrogels cross-linked by EDC and CMC at molar equivalent 2.0 showed increased Td values of about 26.5° C. and 25° C. to 37° C., respectively. The highest values of $\Delta$Hd for collagen hydrogel was measured for molar equivalent 2.0 in all the collagen hydrogel cross-linked by both EDC and CMC.

In vitro Collagenase Degradation

Figure 20:
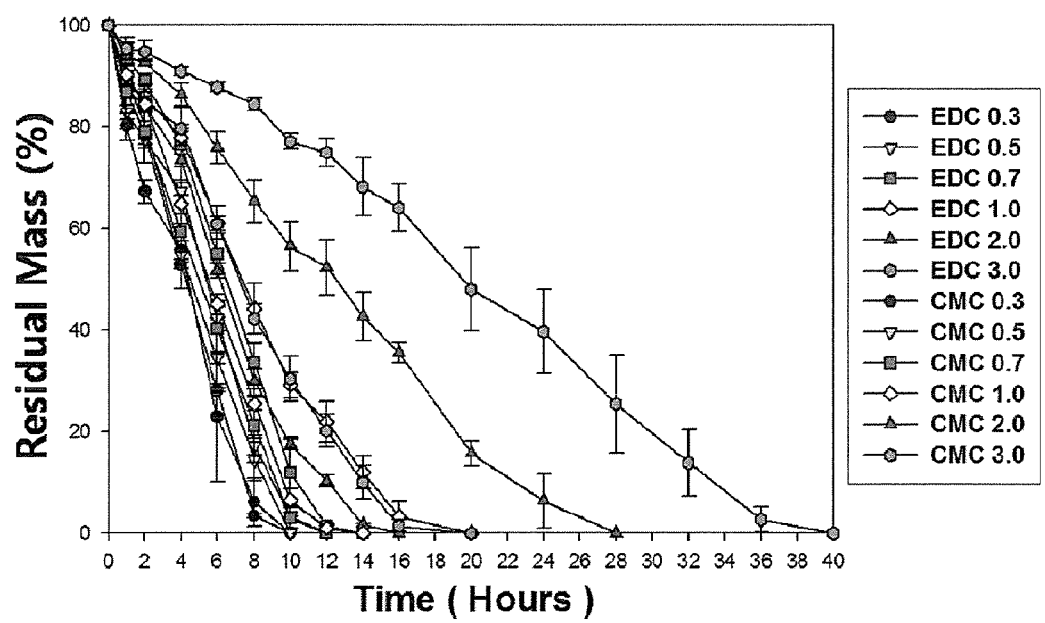
FIG. 20 illustrates in vitro biodegradation the hydrogels tested.

FIG. 20 illustrates in vitro collagenase degration in different hydrogels. No significant difference in enzymatic stability was observed when the molar equivalent of cross-linker was 0.3, 0.5 and 0.7. When the molar equivalent of CMC was higher than 1, the collagen hydrogel cross-linked by CMC was far superior to that of EDC cross-linked hydrogels.

Corneal Epithelial Cells Cultured on Collagen Hydrogel

Figure 21:
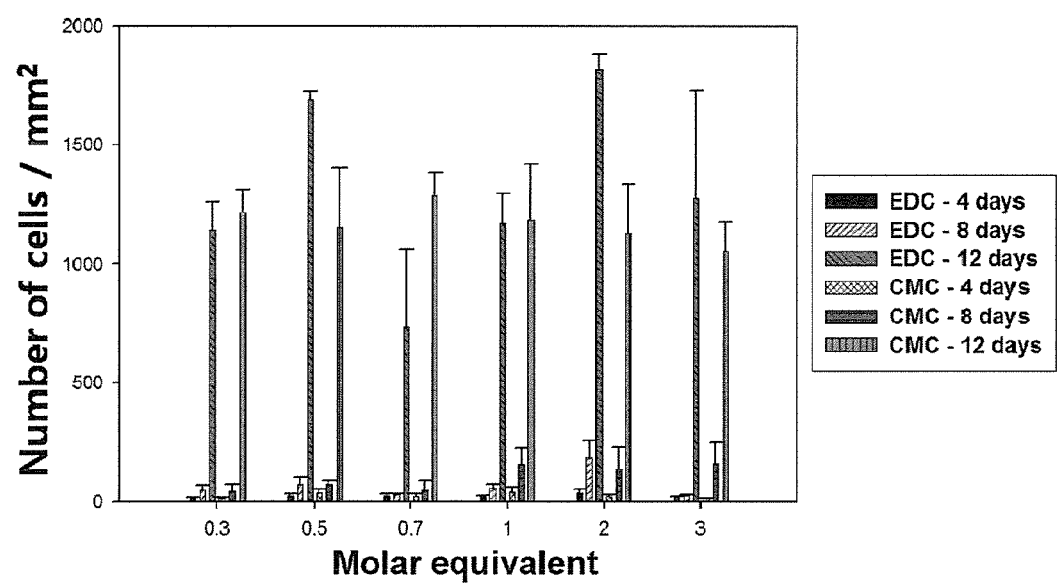
FIG. 21 depicts total cell number of corneal epithelial cells cultured on collagen hydrogels.
Figure 23:
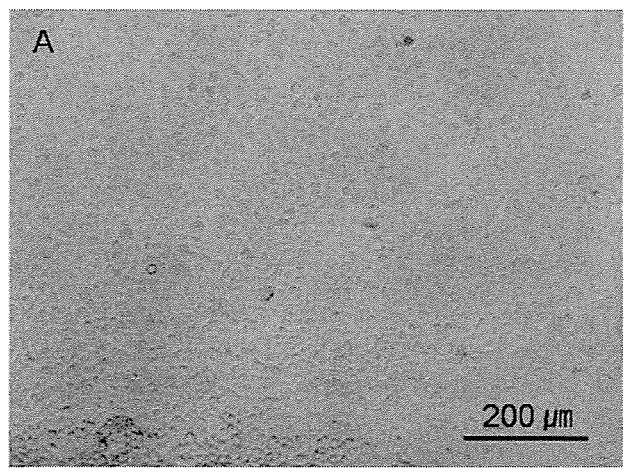
FIG. 23 shows collagen hydrogels confluent with corneal epithelial cells (A) and corneal endothelial cells (B).
Figure 23:
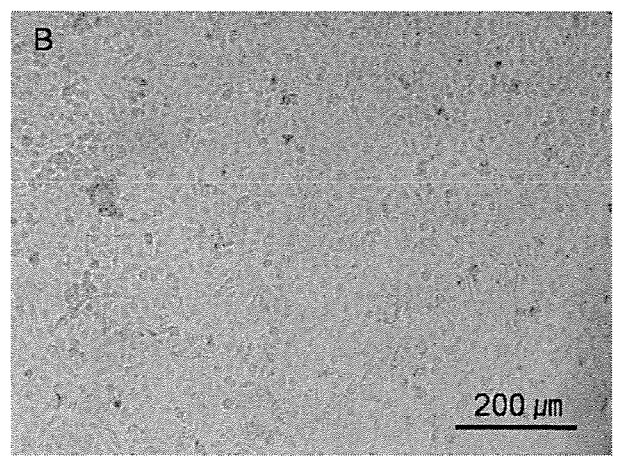

FIG. 21 illustrates graphically the total cell number of corneal epithelial cells cultured on collagen hydrogels. Total cell number of cells was similar to that of CMC cross-linked gels in all days observed. The corneal epithelial cells were confluent on every collagen hydrogels cross-linked with both EDC and CMC in 15 days after seeding. As illustrated in FIG. 23, all collagen hydrogels successfully supported epithelial stratification in culture and may be used as a substrate for corneal epithelial cells growth (A).

Corneal Endothelial Cells Cultured on Collagen Hydrogel

Figure 22:
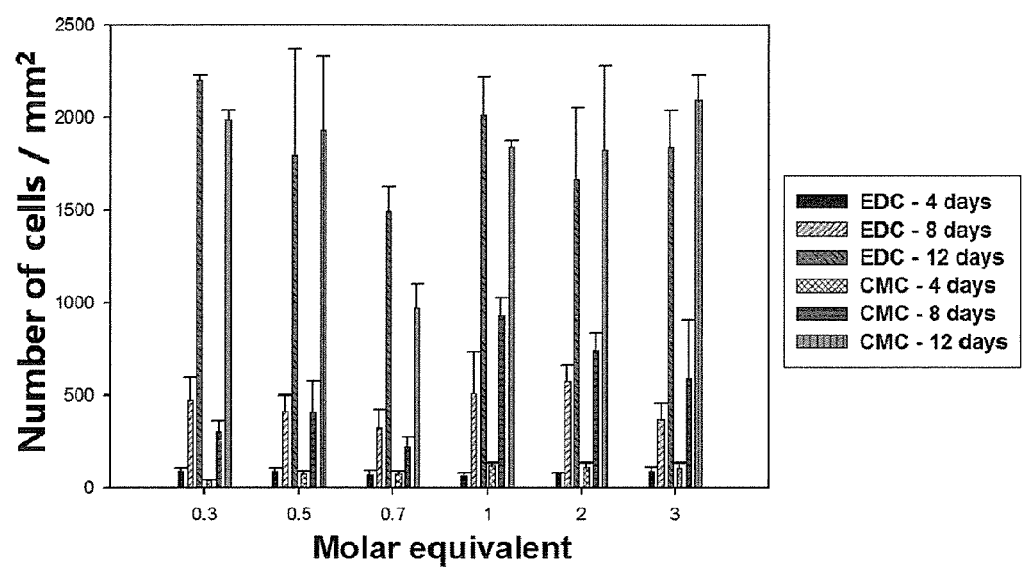
FIG. 22 depicts total cell number of corneal endothelial cells cultured on collagen hydrogels.

FIG. 22 illustrates graphically the total cell number of corneal endothelial cells cultured on collagen hydrogels. The corneal endothelial cells were generally well cultured on collagen hydrogels cross-linked with both EDC and CMC. When molar equivalents were 0.3, 0.7 and 1.0, the collagen hydrogel cross-linked EDC exhibited slightly more cultured corneal endothelial cells than that of CMC cross-linked gels. However, at molar equivalent of 0.5, 2.0 and 3.0, the collagen hydrogel cross-linked by CMC had slightly greater corneal endothelial cells counts than that by EDC. As illustrated in FIG. 23, all collagen hydrogels studied could culture corneal endothelial cells. The corneal endothelial cells were confluent on all collagen hydrogels postseeding 12 days (B).

Neurites Cultured on Collagen Hydrogel

Figure 24:
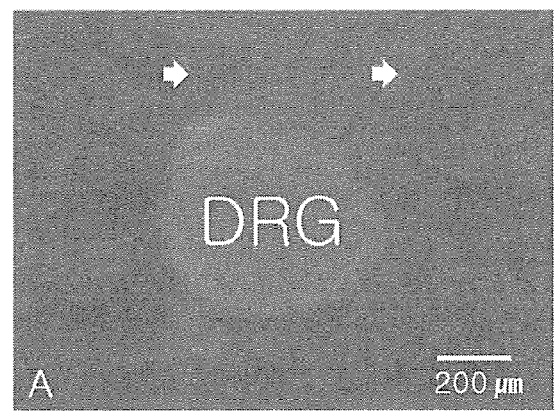
FIG. 24 shows neurites on collagen hydrogels.
Figure 24:

FIG. 24 shows neurites on collagen hydrogels. Neurites were cultured on all collagen hydrogels cross-linked by (A) CMC (0.3) and (B) EDC (0.3). Significant neurite growth was observed on all collagen hydrogels. The longest and highest density of neurites were observed on gels cross-linked by CMC (0.3) and EDC (1.0).

Figure 25:
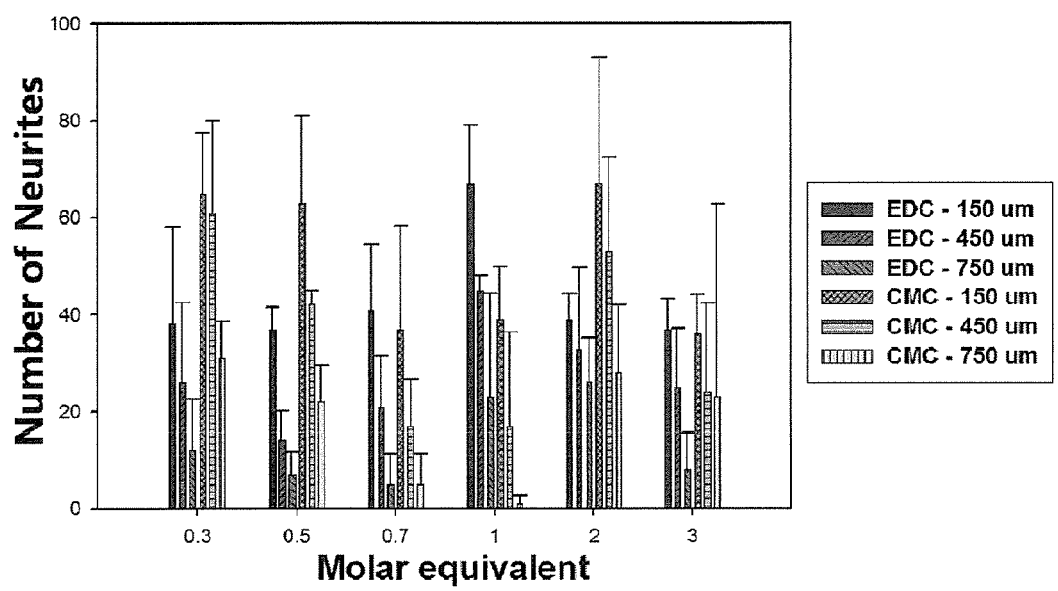
FIG. 25 illustrates total cell number of neurites from DRGs on collagen hydrogels.

FIG. 25 graphically illustrates the total cell number of neurites from DRGs on collagen hydrogels (diameter 5 mm) The shortest and smallest density of neurites were observed on gels cross-linked by CMC (0.7) and EDC (0.5). Overall, the collagen hydrogels cross-linked by CMC were thought to be equal or slightly greater than EDC cross-linked gels in the culturing of neurites. However, the neurites were cultured on all collagen hydrogels observed.

In sum, the comparative analysis of two cross-linking agents, EDC and CMC, in the fabrication of collagen hydrogels using 10% porcine collagen solution with a 1:1 ratio of NHS to cross-linker, indicated that CMC provides a longer gelation time over EDC when same molar equivalent of cross-linker was used, allowing for flexibility in manipulation time to construct a hydrogel containing cells. The optimal molar equivalent of EDC was between 0.3 and 1.0 in previous experiments (7, 8) while the optimal molar equivalent of CMC for collagen hydrogels was found to be 2.0. In the same room temperature conditions, CMC has 2.5 or 4 times longer gelation time than EDC. CMC exhibits higher tensile strength at crosslinking ratios equal or greater than 0.7 and lower elongation at break at higher ratios. CMC exhibits higher elastic modulus at crosslinking ratios greater than 0.7, indicating enhanced stiffness. Higher tensile strength, elastic modulus and lower % elongation may indicate higher crosslinking efficiency. The water contents of all collagen hydrogel cross-linked with both EDC and CMC was more than that of human cornea. The refractive index, white light transmission and scattering of all collagen hydrogels cross-linked with both EDC and CMC was comparable to that of human cornea. The denaturation temperature and the enthalpy of collagen hydrogel at molar equivalent 2.0 were the highest in all of the collagen hydrogels. This is consistent with the increased tensile strength of collagen hydrogel at molar equivalent 2.0 and comparable to that of the human cornea. EDC and CMC cross-linked hydrogels may be appropriate substrates for culturing corneal epithelial, endothelial cells and nerve cells from DRGs. The optimal molar equivalent of EDC and CMC was respectively 0.3 and 2.0 when the collagen hydrogels were made using 10% type I pig collagen solution with the ratio of NHS and cross-linker to 1:1 by both methods. The tensile strength of collagen hydrogel cross-linked with CMC 2.0 was 30% stronger than that with EDC 0.3. The denaturation temperature of collagen hydrogel cross-linked with CMC 2.0 was 14 degrees higher than that with EDC 0.3. The collagenase resistance time of collagen hydrogel cross-linked with CMC 2.0 was 18 hrs longer than that with EDC 0.3. Therefore, the properties of collagen hydrogel cross-linked with CMC are superior to those with EDC in various properties.

The CMC has longer gelation time than EDC to cross-link collagen when the same molar equivalent of cross-linker was used. However, the gelation time of EDC (0.3) was longer than that of CMC 2.0 in optimal condition. This was likely because the higher molar equivalent of cross-linker, the quicker of gelation time of collagen hydrogel. This is advantageous for manufacturing hydrogels. Gelation time was dependent, for example, on the collagen concentration, the gelation(reaction) speed, the crosslinker used, contents of crosslinker and the ratio of NHS and cross-linker. The CMC provides a longer gelation time over EDC when same molar equivalent of cross-linker was used, allowing for flexibility in manipulation time to construct a hydrogel containing cells. The CMC cross-linked hydrogels also have superior mechanical properties over those of EDC. At higher molar concentrations of this CMC cross-linker, the gels are more resistant to in vitro collagenase degradation. When the molar equivalent of CMC was 2.0 and 3.0, the resistance time of collagenase degradation was longer 12 and 20 hrs than those of EDC, respectively. The CMC-cross-linked hydrogels are comparable to EDC cross-linked hydrogels in optical and water retention properties, as well as biocompatibility and ability to support growth of corneal epithelial, endothelial cells and nerve cells from DRGs.

Optimal properties of collage hydrogels are shown in Table 6.

TABLE 6

Optimal properties of collagen hydrogel cross-linked with EDC and CMC.

| Property | EDC 0.3 | CMC 2.0 |
| --- | --- | --- |
| Tensile strength (KPa) | 808.7 ± 117.3 | 1099.0 ± 98.0 |
| Water content | 91.76 ± 0.02 | 91.81 ± 0.41 |
| Refractive Index | 1.3453 ± 0.00029 | 1.3456 ± 0.00036 |
| Transmission | 88.92 ± 0.52 | 88.06 ± 1.94 |
| Td (° C.) | 48.58 ± 0.72 | 62.09 ± 4.67 |
| Collagenase resistance | 10 hr | 28 hr |

Example 4

Optimization of Molar Ratio of CMC in Making Collagen Hydrogel Cross-linked with CMC Only Collagen:
1. 13.7% RHC (Recombinant Human Collagen) type III collagen
2. 18.0% RHC type III collagen In this example, the same batch of collagen solution was used and the molar equivalents of CMC tested were 0.4, 0.7, 1.0, and 1.5.

TABLE 7

Optimum molar equivalent of CMC

| Group | Collagen Concentration | Experimental molar equivalent of CMC | Optimum molar equivalent of CMC as tested |
| --- | --- | --- | --- |
| 1 | 13.7% RHC type III | (0.4, 0.7, 1.0, 1.5) | 1.0 |
| 2 | 18% RHC type III | (0.4, 0.7, 1.0, 1.5) | 0.7 |

Method & Results 1. 13.7% type III RHC hydrogel crosslinked CMC only

TABLE 8

Method

| Order | Component & method | Mixing time | Mixing Temp. (° C.) |
| --- | --- | --- | --- |
| 1 | Collagen + $H_2O$ | 30 | 0 |
| 2 | +NHS (10 µL) | 30 | 0 |
| 3 | Wait - 10 min. | | 25 |
| 4 | +CMC (10-40 µL) | 30 | 25 |
| 5 | | 10 | 0 |

TABLE 9

Experimental Conditions

| Molar equivalent of CMC | starting collagen % | Buffer used | NHS/CMC ratio | Final collagen % |
| --- | --- | --- | --- | --- |
| 0.4 | 13.7 | $H_2O$ | 1:1 | 12.2 |
| 0.7 | 13.7 | $H_2O$ | 1:1 | 12.0 |
| 1.0 | 13.7 | $H_2O$ | 1:1 | 11.8 |
| 1.5 | 13.7 | $H_2O$ | 1:1 | 11.8 |

Table 10 illustrates the tensile strength, elongation at break, modulus and toughness of type III RHC collagen hydrogel at different CMC/Coll-$NH_2$ ratios (0.4, 0.7, 1.0, 1.5) using 13.7% collagen solution. The largest value of tensile strength in all collagen hydrogels was the collagen hydrogel crosslinked by CMC with molar equivalent 1.0. The modulus and toughness of collagen hydrogel cross-linked by CMC had a largest value with 1.0. The value of elongation at break of all collagen hydrogel was in between 20% and 40%. In terms of mechanical properties, a molar equivalent of 1.0 was determined to be optimal.

TABLE 10

Results - mechanical properties

| Molar equivalent of CMC | Tensile Strength (KPa) | Elongation at Break % | Modulus (KPa) | Toughness (KPa) |
| --- | --- | --- | --- | --- |
| 0.4 | 1190 ± 155.4 | 18.83 ± 2.18 | 11200 ± 3296 | 77.81 ± 22.08 |
| 0.7 | 1263 ± 159.8 | 23.46 ± 6.84 | 9169 ± 3297 | 109.1 ± 39.64 |
| 1.0 | 2094 ± 344 | 22.58 ± 3.19 | 14350 ± 4613 | 197.30 ± 74.4 |
| 1.5 | 1260 ± 392 | 17.67 ± 3.18 | 10620 ± 1781 | 90.8 ± 58.7 |

Table 11 summarizes optical properties and thermal analysis. White light transmission of all collagen hydrogels made using RHC III was more than 90%. The denaturation temperature and the enthalpy of collagen hydrogel had tendency to increase according to increase molar ratio of CMC. The denaturation temperature of collagen hydrogels cross-linked by CMC at molar equivalent 1.5 showed increased Td values of about 19.3° C. to 42° C. The highest values of ΔHd for collagen hydrogel was measured for molar equivalent 1.5 in all the collagen hydrogel.

TABLE 11

Results - Optical properties & Thermal analysis

| Molar equivalent of CMC | Transmission (%) | Denaturation Temp. (° C.) | Enthalpy (J/g) | Tensile Strength (kPa) |
|---|---|---|---|---|
| 0.4 | 92.82 ± 0.24 | 51.26 ± 0.237 | 1.31 ± 0.12 | 1190 ± 155.4 |
| 0.7 | 93.34 ± 0.18 | 52.7 ± 0.391 | 2.28 ± 0.09 | 1263 ± 159.8 |
| 1.0 | 93.10 ± 0.06 | 59.51 ± 0.601 | 3.31 ± 1.33 | 2094 ± 344 |
| 1.5 | 93.14 ± 0.38 | 61.26 ± 0.226 | 5.07 ± 0.63 | 1260 ± 392 |

Results—Collagenase Degradation

Figure 26:
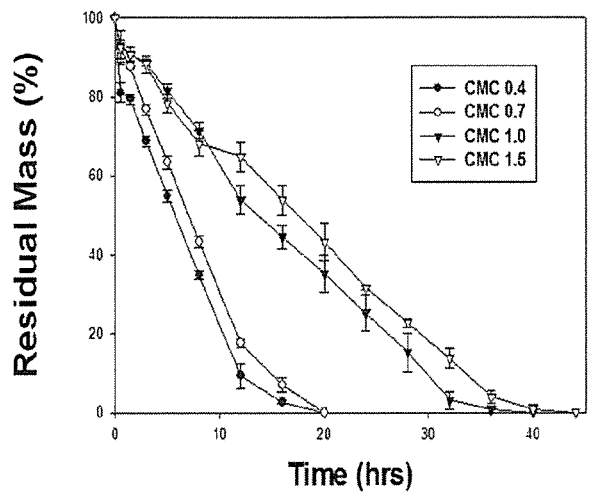
FIG. 26 graphically illustrates hydrogel biodegradation in collagenase, in vitro. A=13.7% Collagen Solution+CMC only and B=13.7% Collagen Solution+CMC+MPC.
Figure 26:
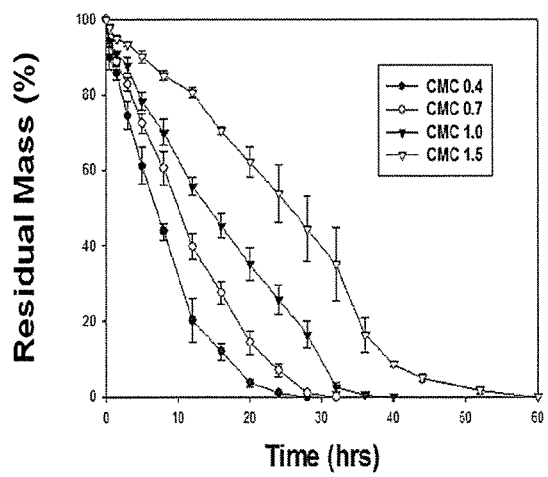

FIG. 26 graphically illustrates hydrogel biodegradation in collagenase, in vitro. A=13.7% Collagen Solution+CMC only and B=13.7% Collagen Solution+CMC+MPC. The residence mass of the collagen hydrogels crosslinked high molar equivalent CMC (1.0, 1.5) was superior to those crosslinked low molar equivalent CMC (0.4, 0.7) in a 13.7% collagen solution. The residence mass of the collagen hydrogels crosslinked with CMC was high when the molar equivalent of CMC was high. Further, MPC was shown to have an effect on the residual mass of collagen.

2. 18% type III RHC hydrogel crosslinked CMC

TABLE 12

Method

| Order | Component & method | Mixing time | Mixing Temp. (° C.) |
|---|---|---|---|
| 1 | Collagen + H$_2$O | 30 | 0 |
| 2 | +NHS (10 μL) | 30 | 0 |
| 3 | Wait - 10 min. | | 25 |
| 4 | +CMC (10-40 μL) | 30 | 25 |
| 5 | | 10 | 0 |

TABLE 13

Experimental Conditions

| Molar equivalent of CMC | starting collagen % | Buffer used | NHS/CMC ratio | Final collagen % |
|---|---|---|---|---|
| 0.4 | 18 | H$_2$O | 1:1 | 16.8 |
| 0.7 | 18 | H$_2$O | 1:1 | 16.3 |

TABLE 13-continued

Experimental Conditions

| Molar equivalent of CMC | starting collagen % | Buffer used | NHS/CMC ratio | Final collagen % |
|---|---|---|---|---|
| 1.0 | 18 | H$_2$O | 1:1 | 15.6 |
| 1.5 | 18 | H$_2$O | 1:1 | 15.2 |

Table 14 summarizes the mechanical properties tested. The tensile strength, elongation at break, modulus and toughness of 18% type III RHC collagen hydrogel at different CMC/Coll-NH$_2$ ratios (0.4, 0.7, 1.0, 1.5). The largest value of tensile strength in the all collagen hydrogel was the collagen hydrogel crosslinked by CMC with molar equivalent 0.7, which also showed the largest modulus and toughness values. The value of elongation at break of all collagen hydrogels was between 15% and 40%.

TABLE 14

Results - Mechanical properties

| Molar equivalent of CMC | Tensile Strength (KPa) | Elongation at Break % | Modulus (KPa) | Toughness (KPa) |
|---|---|---|---|---|
| 0.4 | 1635 ± 295 | 29.79 ± 3.02 | 10050 ± 2301 | 237.6 ± 69.5 |
| 0.7 | 2306 ± 318 | 25.78 ± 2.83 | 17120 ± 2759 | 277.5 ± 42.5 |
| 1.0 | 1725 ± 220 | 19.45 ± 0.78 | 15460 ± 2409 | 119.6 ± 10.3 |
| 1.5 | 2047 ± 268.5 | 25.22 ± 3.58 | 8783 ± 2782 | 214.9 ± 24.85 |

Table 15 summarizes the results of the thermal analysis of the hydrogels. The denaturation temperature (Td) of all collagen hydrogels crosslinked with CMC had a tendency to increase as the molar equivalent of collagen hydrogel was increased. The denaturation temperature and the enthalpy of collagen hydrogel using 18% RHC III were the highest in all collagen hydrogels at molar equivalent 1.5. Both Tds of collagen hydrogels crosslinked with CMC 1.5 was the most increased to about 23.5° C. from 42° C. The highest values of ΔHd for collagen hydrogels used 18% RHC and cross-linked at molar equivalent 0.7 in all the collagen hydrogels. Interestingly, the tensile strength of collagen hydrogels at a molar equivalent 0.7 was the highest values in all collagen hydrogels using an 18% collagen solution.

TABLE 15

Results - Thermal analysis

| Molar equivalent | Denaturation Temp. (° C.) | Enthalpy (J/g) | Tensile Strength (KPa) |
|---|---|---|---|
| 0.4 | 54.74 ± 0.843 | 2.21 ± 0.72 | 1635 ± 295 |
| 0.7 | 58.58 ± 0.463 | 3.383 ± 0.297 | 2306 ± 318 |
| 1.0 | 64.84 ± 0.359 | 3.267 ± 0.527 | 1725 ± 220 |
| 1.5 | 65.52 ± 0.542 | 3.028 ± 0.363 | 2047 ± 268.5 |

Collagenase Degradation

Figure 27:
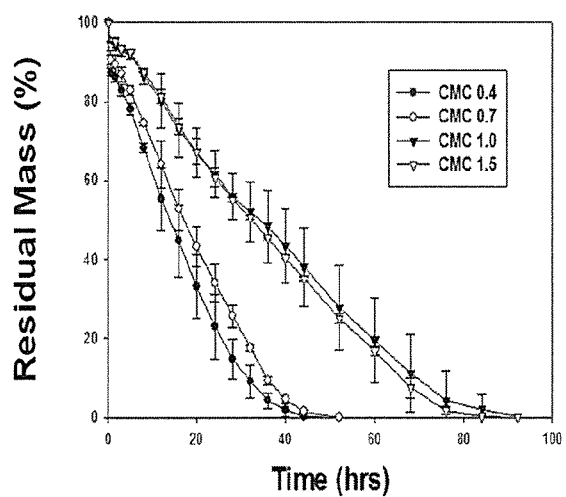
FIG. 27 graphically illustrates hydrogel biodegradation in collagenase, in vitro. A=18.0% Collagen Solution+CMC only and B=18.0% Collagen Solution+CMC+MPC.
Figure 27:
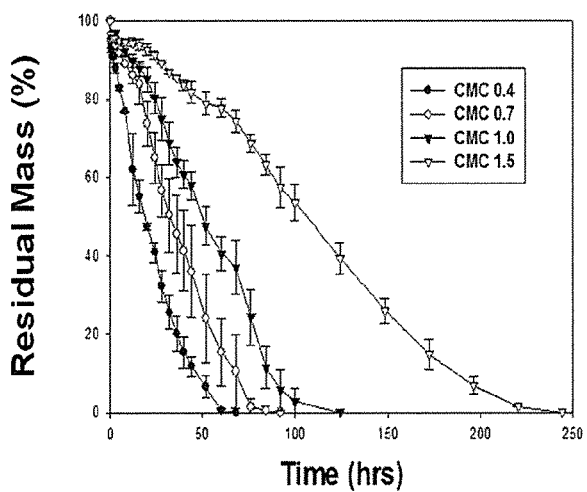

FIG. 27 graphically illustrates hydrogel biodegradation in collagenase, in vitro. A=18.0% Col. Sol.+CMC only and B=18.0% Col. Sol.+CMC+MPC. The residence mass of the collagen hydrogels crosslinked high molar equivalent CMC (1.0, 1.5) was superior to those crosslinked low molar equivalent CMC (0.4, 0.7) in hydrogels made using 18.0% collagen solution. The collagenase resistance results of 18% collagen hydrogel were similar to those of 13.7%. MPC was shown to have an effect on the residual mass of collagen hydrogels.

Overall, an optimal concentration of CMC typically depends on the concentration of collagen or any additives used in the hydrogel, for example. An appropriate molar equivalent of CMC should be selected based on the experimental requirements.

Example 5

Optimization of Molar Ratio of CMC in Making MPC Incorporated Collagen Hydrogel Cross-linked with CMC Collagen:
1. 13.7% RHC type III collagen—initiator (Irgacure/UVA)
2. 13.7% RHC type III collagen—initiator (TEMED/APS)

Tensile strength of collagen hydrogels crosslinked with CMC was initially tested to optimize type III added MPC crosslinked CMC. In this example, 13.7% and 18% type III RHC solutions were tested, with CMC molar equivalents of 0.4, 0.7, 1.0 and 1.5.

The collagen solution used in Group 1 as shown in Table 16 was a type III collagen used in the art. The observed tensile strength was different from previous measured values. The present example used the same batch collagen solution, with molar equivalents of 0.4, 0.7, 1.0, and 1.5.

TABLE 16

Tensile strength - optimal molar equivalents of CMC

| Group | Experimental condition | Experimental molar equivalent | Optimal molar equivalent as tested |
|---|---|---|---|
| 1 | 13.7% RHC III + MPC + CMC (Irgacure) | (0.4, 0.7, 1.0, 1.5) | 1.0, 1.5 |
| 2 | 13.7% RHC III + MPC + CMC (TEMED/APS) | (1.0, 1.5) | 1.0, 1.5 |

Methods and Results
1. 13.7% type III RHC hydrogel—initiator (Irgacure/UVA)

TABLE 17

Method

| Order | Component & method | Mixing time | Mixing Temp. (° C.) |
|---|---|---|---|
| 1 | Collagen + H$_2$O | 30 | 0 |
| 2 | +MPC (100 µL) | 30 | 0 |
| 3 | +PEG | 30 | 0 |
| 4 | +IRGAcure (100 µL) | 30 | 0 |
| 5 | +NHS (10 µL) | 30 | 0 |
| 6 | Wait - 10 min. | | 25 |
| 7 | +CMC | 30 | 25 |
| 8 | | 20 | 0 |
| 9 | UV crosslink | 15 minutes | Room Temp. |

TABLE 18

Experimental Conditions

| Molar equivalent of CMC | Starting collagen % | Buffer used | coll/MPC ratio | PEG/MPC ratio | IRGAcure w/v % | NHS/CMC ratio | Final collagen % |
|---|---|---|---|---|---|---|---|
| 0.4 | 13.7 | H$_2$O | 2:1 | 1:3 | 0.5 | 1:1 | 9.4 |
| 0.7 | 13.7 | H$_2$O | 2:1 | 1:3 | 0.5 | 1:1 | 9.4 |
| 1.0 | 13.7 | H2O | 2:1 | 1:3 | 0.5 | 1:1 | 9.2 |
| 1.5 | 13.7 | H2O | 2:1 | 1:3 | 0.5 | 1:1 | 9.3 |

Table 19 shows the mechanical properties of the tested hydrogels. The tensile strength, elongation at break, modulus and toughness of type III RHC collagen hydrogel at different CMC/Coll-NH$_2$ ratios (0.4, 0.7, 1.0, 1.5) using 13.7% collagen solution with MPC were measured. The largest value of tensile strength in all collagen hydrogels was the collagen hydrogel crosslinked by CMC with molar equivalent 1.5. The elongation and toughness of hydrogels crosslinked CMC with molar equivalent 1.0 were better than that with molar equivalent 1.5.

TABLE 19

Results - Mechanical properties

| Molar equivalent of CMC | Tensile Strength (kPa) | Elongation at Break % | Modulus (KPa) | Toughness (KPa) |
|---|---|---|---|---|
| 0.4 | 763 ± 133.8 | 20.45 ± 0.7 | 6599 ± 1851 | 62.07 ± 7.26 |
| 0.7 | 1139 ± 251.9 | 36.55 ± 28.23 | 10340 ± 1051 | 255.5 ± 26.91 |
| 1.0 | 1282 ± 175.8 | 30.66 ± 7.65 | 11270 ± 3428 | 205.1 ± 69.78 |
| 1.5 | 1297 ± 242 | 19.83 ± 2.33 | 11600 ± 3311 | 91.00 ± 27.39 |

Table 20 shows the optical properties and thermal analysis of the hydrogels tested. White light transmission of all collagen hydrogels made by using RHC III was more than 90%. The denaturation temperature (Td) of all collagen hydrogel crosslinked had a tendency to increase as the molar equivalent of collagen hydrogel was increased. The denaturation temperature and the enthalpy of collagen hydrogel incorporated MPC using 13.7% RHC III were the highest in all collagen hydrogels at molar equivalent 1.5. The denaturation temperature of collagen hydrogels crosslinked at molar equivalent 1.5 was the most increased to about 19.6° C. from 42° C.

TABLE 20

Results - Optical properties & Thermal analysis

| Molar equivalent | Transmission (%) | Denaturation Temp. (° C.) | Enthalpy (J/g) |
|---|---|---|---|
| 0.4 | 93.56 ± 0.55 | 50.65 ± 1.147 | 1.188 ± 0.199 |
| 0.7 | 94.14 ± 0.08 | 54.66 ± 0.977 | 1.847 ± 0.643 |
| 1.0 | 93.82 ± 0.16 | 57.64 ± 0.764 | 1.943 ± 0.18 |
| 1.5 | 93.91 ± 0.34 | 61.56 ± 0.312 | 2.287 ± 0.381 |

Results—Collagenase Degradation

Figure 28:
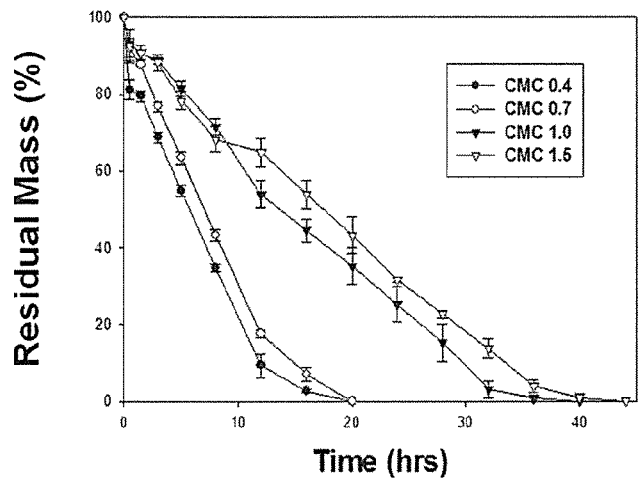
FIG. 28 graphically illustrates hydrogel biodegradation in collagenase, in vitro. A=13.7% collagen solution+CMC only, and B=13.7% collagen solution+CMC+MPC.
Figure 28:
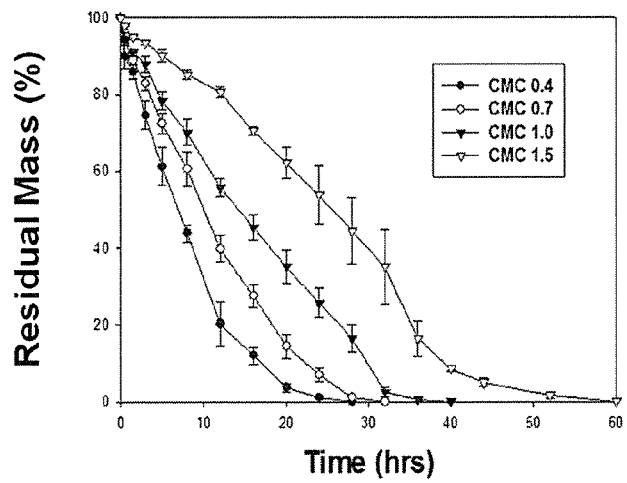

FIG. 28 graphically illustrates hydrogel biodegradation in collagenase, in vitro. A=13.7% collagen solution+CMC only, and B=13.7% collagen solution+CMC+MPC. The residence mass of the collagen hydrogels crosslinked with CMC was high when the molar equivalent of CMC was high. An apparent difference of residence mass was observed when the molar equivalent of CMC was increased in collagen hydrogels made by collagen and MPC. It was observed that MPC has an effect on the residual mass of collagen though the final concentration of collagen solution in a collagen hydrogel added with MPC was low. The highest values of collagen residual mass for collagen hydrogels incorporated MPC used 13.7% RHC III crosslinked CMC at molar equivalent 1.5 in all the collagen hydrogels tested.

2. 13.7% type III RHC hydrogel—initiator (TEMED/APS)

TABLE 21

| | Method | | |
|---|---|---|---|
| Order | Component & method | Mixing time | Mixing Temp. (° C.) |
| 1 | Collagen + MES | 30 | 0 |
| 2 | +MPC (200 µL) | 30 | 0 |
| 3 | +PEGDA | 30 | 0 |
| 4 | +APS (18-26 µL) | 30 | 0 |
| 5 | +TEMED (37-53 µL) | 30 | 0 |
| 6 | +NHS (10 µL) | 30 | 0 |
| 7 | Wait - 10 min. | | 25 |
| 8 | +CMC | 20 | 25 |
| 9 | | 20 | 0 |
| 10 | LN2 | 5 minutes | Room Temp. |

TABLE 22

Experimental Conditions

| CMC | starting collagen % | Buffer used | coll/MPC ratio | PEG/MPC ratio | APS/MPC w/v % | TEMED/MPC v/v % | NHS/CMC ratio | Final collagen % |
|---|---|---|---|---|---|---|---|---|
| 1.0 | 13.7 | MES | 2:1 | 1:3 | 2 | 2 | 1:1 | 8.0 |
| 1.5 | 13.7 | MES | 2:1 | 1:3 | 2 | 2 | 1:1 | 8.2 |

Table 23 summarizes the mechanical properties and transmission of the hydrogels tested. The tensile strength, elongation at break, modulus and toughness of type III RHC collagen hydrogel at CMC/Coll-NH$_2$ ratios (1.0, 1.5) were measured. The tensile strength of collagen hydrogel initiated TEMED/APS was similar to that initiated with irgacure.

TABLE 23

Results -Mechanical properties and Transmission

| CMC | Tensile Strength (KPa) | Elongation at Break % | Modulus (KPa) | Toughness (KPa) | Transmission (%) |
|---|---|---|---|---|---|
| 1.0 | 1163 ± 320 | 27.16 ± 9.30 | 10190 ± 828.0 | 168.7 ± 122.3 | 93.53 ± 0.37 |
| 1.5 | 1198 ± 166 | 22.22 ± 1.63 | 10770 ± 2386 | 85.88 ± 17.22 | 92.80 ± 0.17 |

Example 6

Optimization of Molar Ratio of CMC in Making MPC Incorporated Collagen Hydrogels Cross-linked with CMC Collagen:
1. 18.0% RHC type III collagen—initiator (Irgacure/UVA)
2. 18.0% RHC type III collagen—initiator (TEMED/APS)

In this example, tensile strength, water contents, refractive index, denaturation temperature and collagenase degradation of collagen hydrogel crosslinked with CMC were measured to find the optimum molar equivalent of CMC when the collagen hydrogel was made with 18.0% RHC type III collagen and MPC. The number of cultured corneal epithelial cells on the collagen hydrogels was counted to check biocompatibility. An 18% RHC Type III solution was used for making the collagen hydrogels. The molar equivalents of CMC tested were 0.4, 0.7, 1.0 and 1.5. MPC was crosslinked with PEGDA.

Two initiator systems were compared: Irgacure 2959 and TEMED/APS.

TABLE 24

Optimum molar equivalent of CMC

| Group | Experimental group | Experimental molar equivalent | Optimum Equivalent |
|---|---|---|---|
| 1 | 18% RHC III + MPC + CMC (Igracure) | (0.4, 0.7, 1.0, 1.5) | 1.0 |
| 2 | 18% RHC III + MPC + CMC (APS + TEMED) | (0.4, 0.7, 1.0, 1.5) | 1.0 |

TABLE 25

Optimum mix ratio of collagen and MPC

| Group | Experimental group | Experimental mix ratio | Optimum ratio |
|---|---|---|---|
| 1 | 18% RHC III + MPC + CMC (Igracure) | (1:1, 4:1, 2:1) | 2:1 |
| 2 | 18% RHC III + MPC + CMC (APS + TEMED) | (1:1, 4:1, 2:1) | 2:1 |

Materials and Methods
Method

1. Preparation of Collagen-MPC Hydrogel Crosslinked CMC and with Chemical Initiator—Irgacure:

600 mg of 18.0 wt % RHC III solution buffered with 150 µL distilled deionized water was thoroughly mixed with PEGDA, 100 µl of 50% (w/v) MPC and 100 µL 10.5% (w/v) Irgacure aqueous solution in the mixing system (PEGDA:MPC=1:3 (w/w)). Calculated volumes of NHS and CMC (both at 10% wt/vol, EDC:NHS:collagen $NH_2$=0.4:0.4:1) were injected into the above mixture sequentially and mixed thoroughly. Ratios of CMC:NHS:collagen $NH_2$ of 0.4:0.4:1, 0.7:0.7:1, 1:1:1 and 1.5:1.5:1 were prepared for comparison with chemically crosslinked samples. The homogenous mixture was dispensed into molds, UV irradiated in a crosslinking oven at a wavelength of 313-416 nm and intensity of 5.27 mW/$cm^2$ for 15 minutes. They were then post-cured as described above for chemically crosslinked hydrogels. Hydrogels with different RHC III to MPC ratios, 4:1 or 1:1, were similarly prepared for comparison.

2. Preparation of Collagen-MPC Hydrogel Crosslinked CMC and with Chemical Initiator—TEMED/APS:

600 mg of 18.0 wt % RHC III solution buffered with 150 µL of 0.625 M MES buffer was thoroughly mixed in a syringe mixing system. 200 µL MPC solution in 0.625 M MES was added into the mixing system (collagen:MPC (w/w)=2:1) and thoroughly mixed with the collagen solution. PEGDA was then added by a microsyringe (PEGDA:MPC (w/w)=1:3), followed by thoroughly mixing. Calculated volumes of 4% (w/v) APS in MES and 2% (v/v) TEMED in MES were added sequentially and thoroughly mixed (APS/MPC (w/w)=0.02:1, APS:TEMED (w/w) 1:0.77). Then, calculated volumes of NHS and CMC (both at 10% wt/vol, EDC:NHS:collagen $NH_2$=0.4:0.4:1) were injected into the above mixture sequentially and mixed thoroughly. Ratios of CMC:NHS:collagen $NH_2$ of 0.4:0.4:1, 0.7:0.7:1, 1:1:1 and 1.5:1.5:1 were prepared for comparison with chemically crosslinked samples. The homogenous mixture was dispensed into molds. The hydrogels were cured at 100% humidity under nitrogen at room temperature for 16 h and then at 37° C. for 5 h. Hydrogels with different RHCIII to MPC ratios, 4:1 or 1:1, were similarly prepared for comparison.

Results

1. Collagen Hydrogel Initiated with Irgacure
   Initiator: Irgacure
   UVA irradiation time: 15 minutes
   Final pH: 5.5
   Crosslinker of collagen: CMC/NHS
   Ratio of CMC and NHS: 1:1

Table 26 summarizes the mechanical properties of the hydrogels tested. The tensile strength, elongation at break, modulus and toughness of RHC type III collagen hydrogel initiated Irgacure using 18.0% collagen solution and MPC at different CMC/Coll-$NH_2$ ratios (0.4, 0.7, 1.0, 1.5) were measured.

TABLE 26

Mechanical properties of collagen hydrogel

| Sample No. | Starting Col. % | Final Col. % | Coll/MPC (w/w) | Crosslinker/coll-$NH_2$ ratio | Tensile Strength (MPa) | Elongation at break (%) | Modulus (MPa) | Toughness (kpa) |
|---|---|---|---|---|---|---|---|---|
| 67, 87 | 18% | 10.0% | 2:1 | 0.4 | 1.96 ± 0.46 | 25.78 ± 2.88 | 14.3 ± 1.93 | 208.5 ± 73.1 |
| 75, 88 | 18% | 9.7% | 2:1 | 0.7 | 1.80 ± 0.17 | 23.44 ± 4.84 | 14.34 ± 2.45 | 186.0 ± 74.6 |
| 89, 107 | 18% | 9.8% | 2:1 | 1.0 | 1.82 ± 0.32 | 24.00 ± 2.77 | 14.38 ± 2.74 | 175.7 ± 65.7 |
| 90 | 18% | 9.4% | 2:1 | 1.5 | 1.50 ± 0.08 | 19.99 ± 1.53 | 15.37 ± 1.81 | 112.9 ± 19.91 |
| 108 | 18% | 8.7% | 1:1 | 1.0 | 1.67 ± 0.20 | 24.44 ± 1.53 | 14.54 ± 1.54 | 147.0 ± 18.0 |
| 109 | 18% | 10.8% | 4:1 | 1.0 | 1.52 ± 0.22 | 22.13 ± 1.25 | 14.34 ± 2.31 | 111.6 ± 11.8 |
| 12, 121 | 18% | 13.4% | w/o | 1.0 | 1.73 ± 0.22 | 19.45 ± 0.78 | 15.46 ± 2.41 | 119.6 ± 10.3 |

Figure 29:
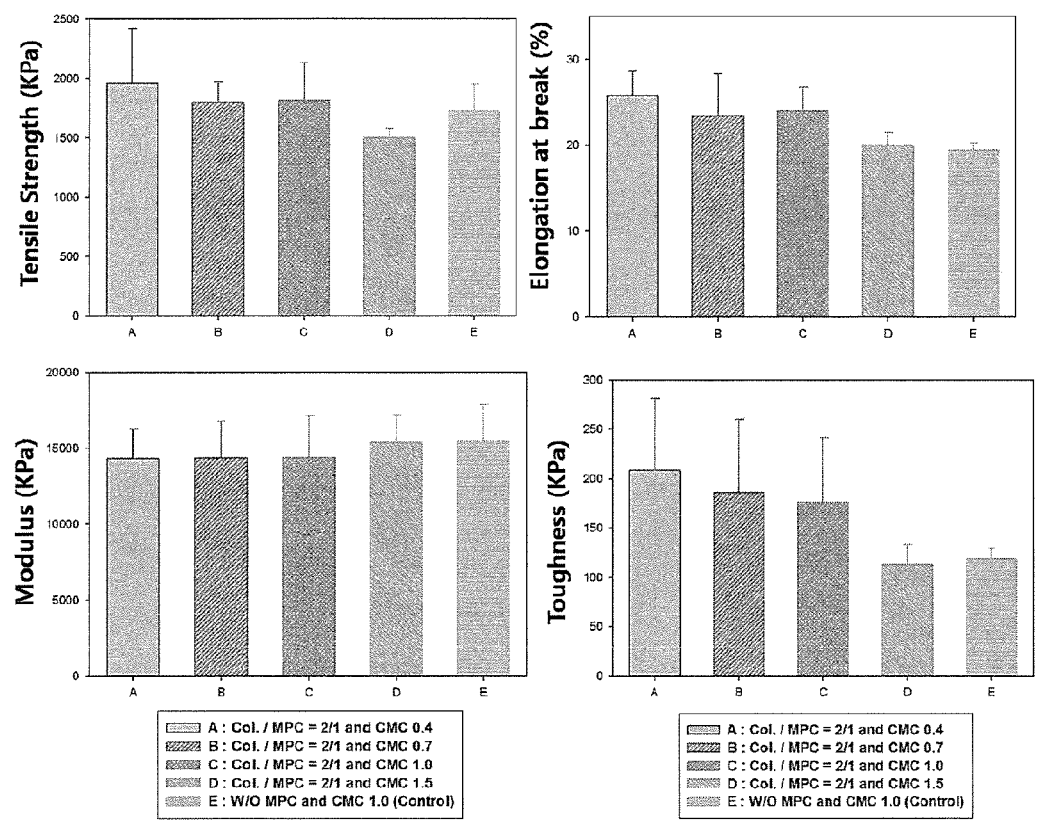
FIG. 29 graphically illustrates the mechanical properties of hydrogels.

FIG. 29 graphically illustrates the mechanical properties of the hydrogels tested. The largest value of tensile strength in the all collagen hydrogel was the collagen hydrogel crosslinked by CMC with molar equivalent 0.4, which also showed the largest value of elongation at break and toughness of collagen hydrogel crosslinked by CMC. The value of elongation at break of all collagen hydrogels was between 20% and 30%. However, the modulus of collagen hydrogel crosslinked by CMC had a largest value at 1.5. When CMC and PEGDA were used to crosslink collagen and MPC (Col.:MPC=2:1), the best molar equivalent of CMC was 0.4 with regard to tensile strength.

Figure 30:
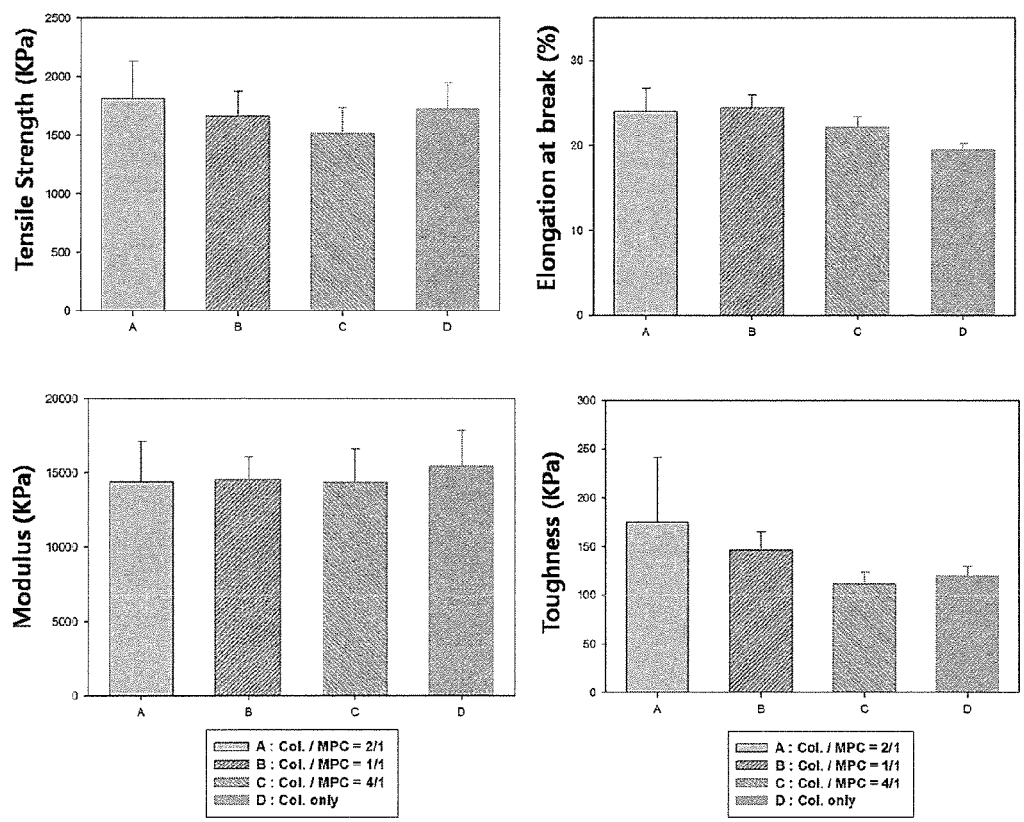
FIG. 30 graphically illustrates the mechanical properties at difference collagen:MPC ratios.

FIG. 30 graphically illustrates the mechanical properties at difference collagen:MPC ratios. The tensile strength, elongation at break, modulus and toughness of 18% RHC type III collagen hydrogel at different collagen:MPC ratios (2:1, 1:1, 4:1) were measured. The largest value of tensile strength and toughness in the all collagen hydrogels was the collagen:MPC ratio of 2:1. However, the modulus and toughness of all collagen hydrogels were similar value in all collagen hydrogels.

Water Contents, Refractive Index and DSC Data

Figure 31:
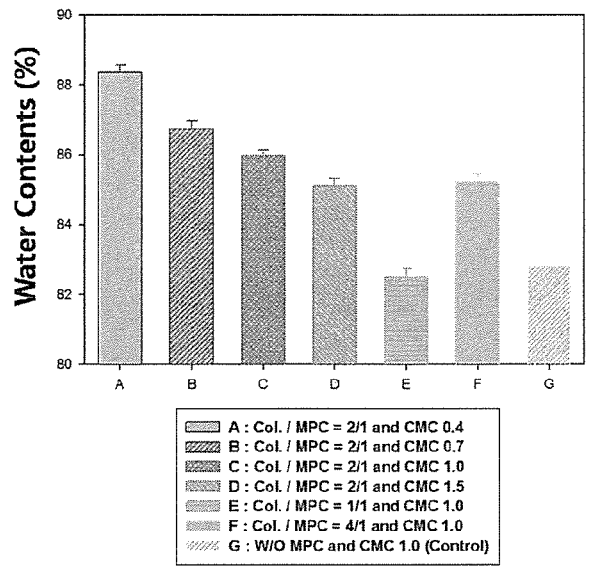
FIG. 31 illustrates the water content and refractive index results of hydrogels.
Figure 31:
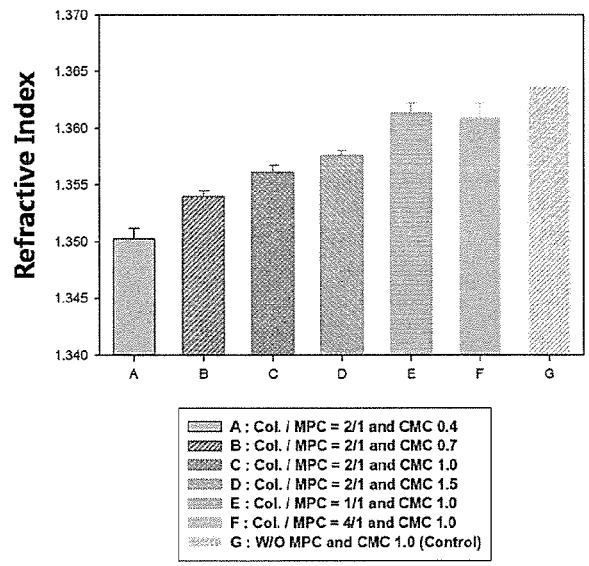

Table 27 summarizes and FIG. 31 illustrates the water content and refractive index results of the hydrogels tested. When the collagen:MPC ratio was 2:1, as the molar equivalent was increased, the water contents of RHC hydrogel had a tendency to decrease. The water contents of RHC hydrogel were between 85% and 89%. When the molar equivalent of CMC was 1.0, the water content of collagen:MPC ratio 2:1 was slightly higher than 1:1 and 4:1.

However, the refractive index showed a tendency opposite to that of water content. When the collagen:MPC ratio was 2:1, as the molar equivalent was increased, the refractive index of RHC hydrogel had a tendency to increase. The refractive indexes of RHC hydrogels were between 1.35 and 1.36. When the molar equivalent of CMC was 1.0, the refractive index of collagen: MPC ratio 2:1 was slightly lower than 1:1 and 4:1. It is likely that high water contents give negative effects on the refractive index.

Figure 32:
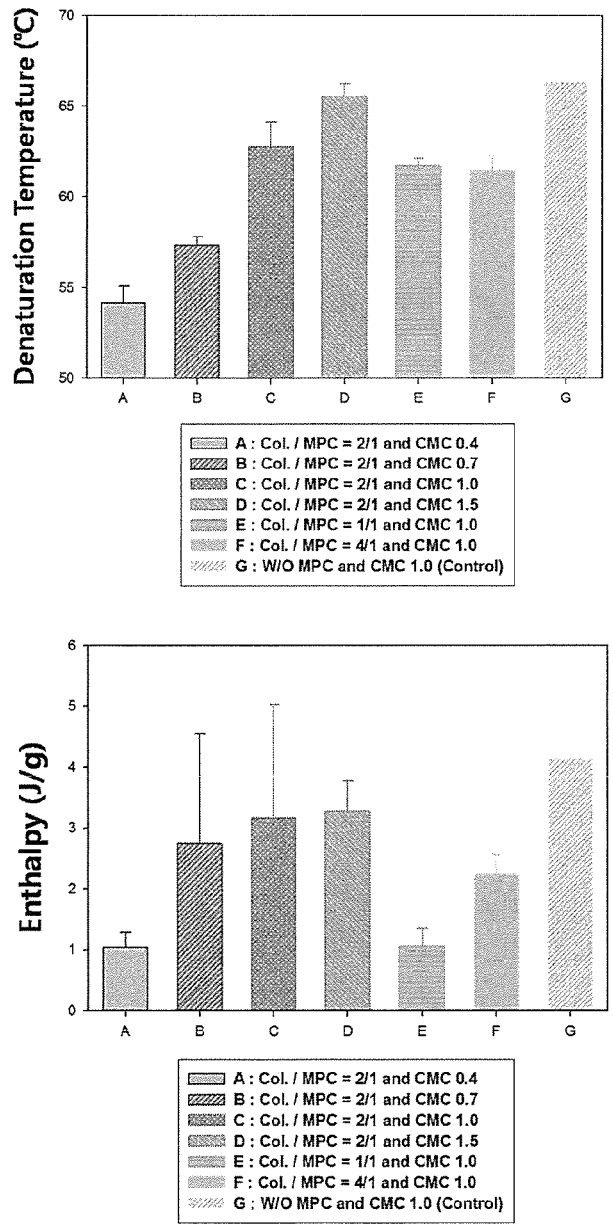
FIG. 32 illustrates the denaturation temperature and enthalpy of hydrogels.

FIG. 32 illustrates the denaturation temperature and enthalpy of the hydrogels tested. As the molar equivalent was increased, the denaturation temperature of RHC hydrogel had a tendency to increase when the collagen:MPC ratio was 2:1. The denaturation temperature and the enthalpy of collagen hydrogels using 18% RHC III were the highest in all collagen hydrogels at molar equivalent 1.5. When the molar equivalent of CMC was 1.5, the denaturation temperature was very similar to that of normal cornea (65° C.). While, when the molar equivalent of CMC was 1.0, the denaturation temperature of collagn:MPC ratio 2:1 was slightly higher than those of 1:1 and 4:1. The enthalpy of collagen hydrogel had a similar tendency to that of denaturation temperature. The highest values of LHd for collagen hydrogels with CMC at molar equivalent 1.5 in all the collagen hydrogels tested.

Collagenase Degradation

Figure 33:
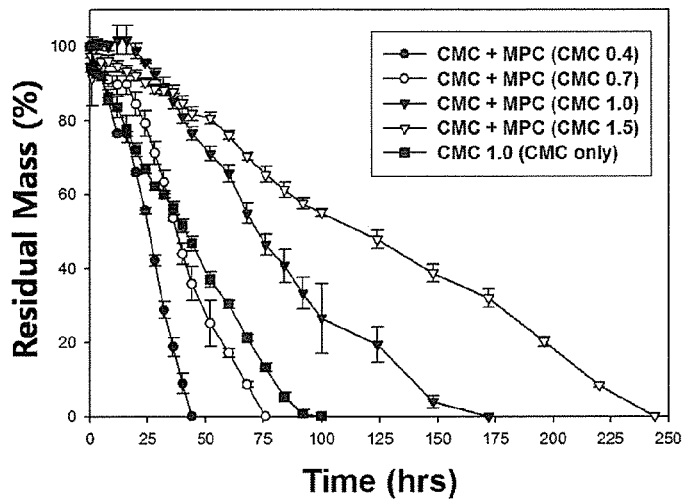
FIG. 33 graphically illustrates biodegradaion of hydrogels, in collagenase.
Figure 33:
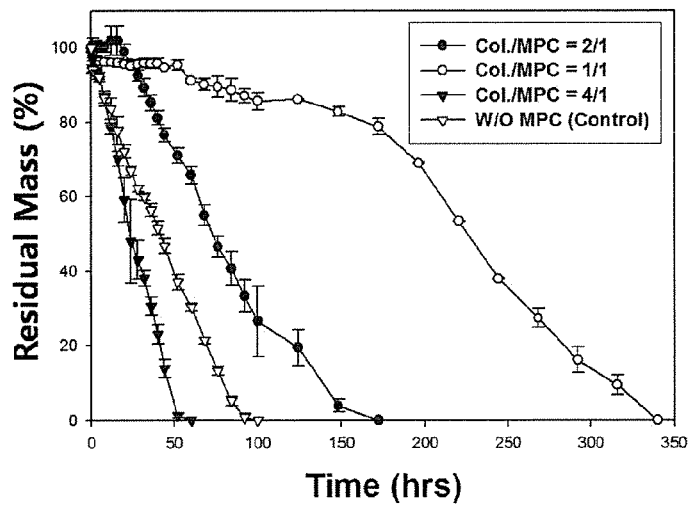

FIG. 33 graphically illustrates biodegradation of the hydrogels tested, in collagenase. When the collagen:MPC ratio was 2:1, as the molar equivalent was increased, the collagen residual mass of RHC hydrogel had a tendency to increase. The highest values of collagen residual mass for collagen hydrogels used at molar equivalent CMC 1.5 in all the collagen hydrogels. When the molar equivalent of CMC was 1.0, the collagen residual mass of collagen:MPC ratio 1:1 was superior to 2:1 and 4:1. It was observed that MPC has an effect on the resistance of collagen hydrogel to collagenase.

Cell Biocompatibility

Figure 34:
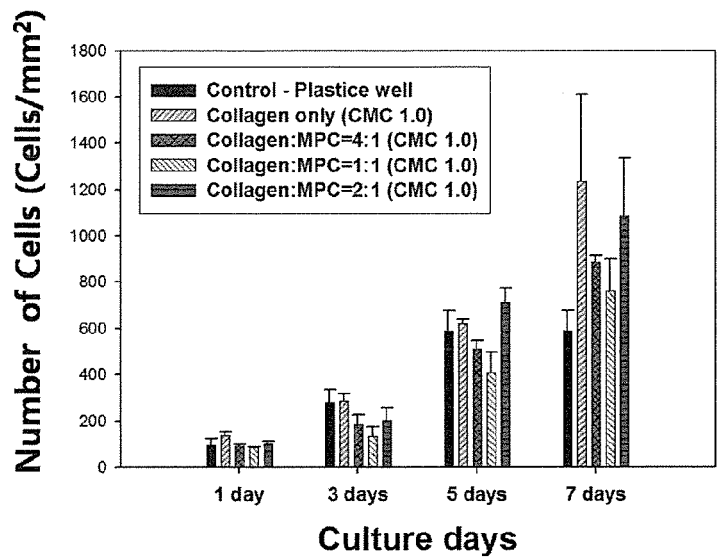
FIG. 34 graphically illustrates the numbers of cells in different hydrogels tested.
Figure 34:
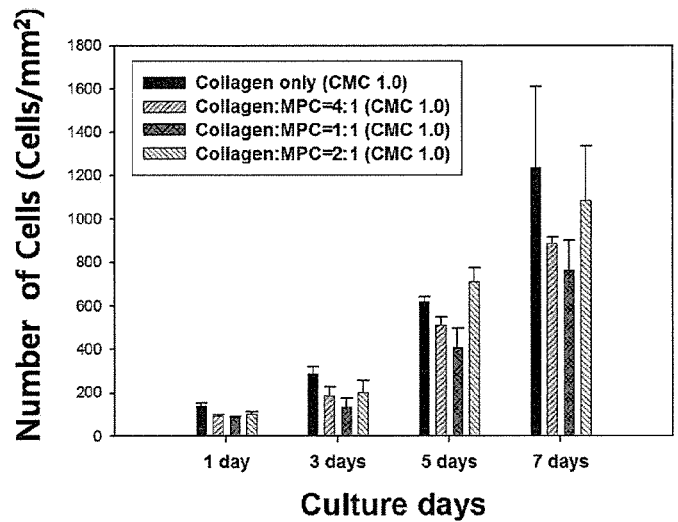

Tables 28 and 29 summarize the results of corneal epithelial cell number and confluence rate. FIG. 34 graphically illustrates the numbers of cells in different hydrogels tested. Though MPC has known anti-adhesive properties in cells, all types of hydrogels successfully demonstrated culturing of corneal epithelial cells. The corneal epithelial cells were confluent on all collagen hydrogels tested. At day 7, the number of cells cultured on the hydrogels was higher than in a plastic well. All collagen/MPC hydrogels tested could be used as a substrate for corneal epithelial cells. Collagen-MPC hydrogels supported attachment and proliferation of immortalized human corneal epithelial cells and the cells reached confluence at about day 5.

TABLE 27

Water contents and refractive index

| Sample No. | Coll/MPC (w/w) | Crosslinker/coll-NH$_2$ ratio | Refractive index | Water content (%) | $T_d$ (° C.) | Enthalpy (J/g) |
| --- | --- | --- | --- | --- | --- | --- |
| 67, 87 | 2:1 | 0.4 | 1.3503 ± 0.00090 | 88.35 ± 0.217 | 54.15 ± 0.96 | 1.05 ± 0.23 |
| 75, 88 | 2:1 | 0.7 | 1.3540 ± 0.00052 | 86.74 ± 0.219 | 57.35 ± 0.46 | 2.74 ± 1.80 |
| 89, 107 | 2:1 | 1.0 | 1.3561 ± 0.00062 | 85.97 ± 0.152 | 62.74 ± 1.40 | 3.17 ± 1.86 |
| 65, 90 | 2:1 | 1.5 | 1.3576 ± 0.00043 | 85.12 ± 0.205 | 65.53 ± 0.71 | 3.26 ± 0.51 |
| 108 | 1:1 | 1.0 | 1.3613 ± 0.00090 | 82.51 ± 0.231 | 61.74 ± 0.36 | 1.05 ± 0.30 |
| 109 | 4:1 | 1.0 | 1.3609 ± 0.00134 | 85.20 ± 0.257 | 61.43 ± 0.79 | 2.23 ± 0.33 |
| 12, 121 | w/o | 1.0 | 1.3637 ± 0.00101 | 82.81 ± 0.311 | 66.34 ± 1.12 | 4.14 ± 0.25 |

TABLE 28

Corneal epithelial Cell number cultivated on the collagen gels (cells/mm$^2$)

| | Col.; MPC | Sample | Initial seeding | 1 day Ave. | 1 day Stdev. | 3 days Ave. | 3 days Stdev. | 5 days Ave. | 5 days Stdev. | 7 days Ave. | 7 days Stdev. |
|---|---|---|---|---|---|---|---|---|---|---|---|
| Plastic well | — | Control | 105 | 95.8 | 25.5 | 280 | 56 | 587.1 | 91.52 | 0 | 0 |
| Collagen only | 1:0 | 121-1 | 105 | 135.6 | 17.67 | 285 | 34.3 | 617.9 | 22.82 | 1237 | 373.6 |
| Irgacure/UVA | 4:1 | 109-1 | 105 | 92.16 | 7.047 | 183 | 41.5 | 510.9 | 35.57 | 887.4 | 26.89 |
| | 1:1 | 108-1 | 105 | 84.03 | 3.851 | 132 | 40.7 | 407.8 | 86.44 | 761.9 | 138 |
| | 2:1 | 107-1 | 105 | 100.8 | 13.21 | 203 | 55 | 712.6 | 61.61 | 1085 | 249.9 |

TABLE 29

Confluent rate of corneal epithelial cells (%)

| | Col.; MPC | Sample | 3 days | 5 days | 7 days |
|---|---|---|---|---|---|
| CMC only | — | 121-1 | 90 | 100 | 100 |
| Irgacure/UVA | 4:1 | 109-1 | 90 | 100 | 100 |
| | 1:1 | 108-1 | 70 | 90 | 100 |
| | 2:1 | 107-1 | 80 | 95 | 100 |
| Control | — | Plastic well (12 well) | 100 | 150 | — |

Table 30 summarizes transmission and scattering results. White light transmission and backscatter of collagen hydrogels made by RHC III crosslinked with CMC 1.0 was 88.1 and 2.06, respectively.

TABLE 30

Transmission and Scattering

| | Col.; MPC | Sample | Transmittance (%) | Backscatter (%) |
|---|---|---|---|---|
| UVA/Irgacure | 2:1 | 107-1 | 88.1 ± 1.5 | 2.06 ± 0.35 |

NMR Data

Figure 35:
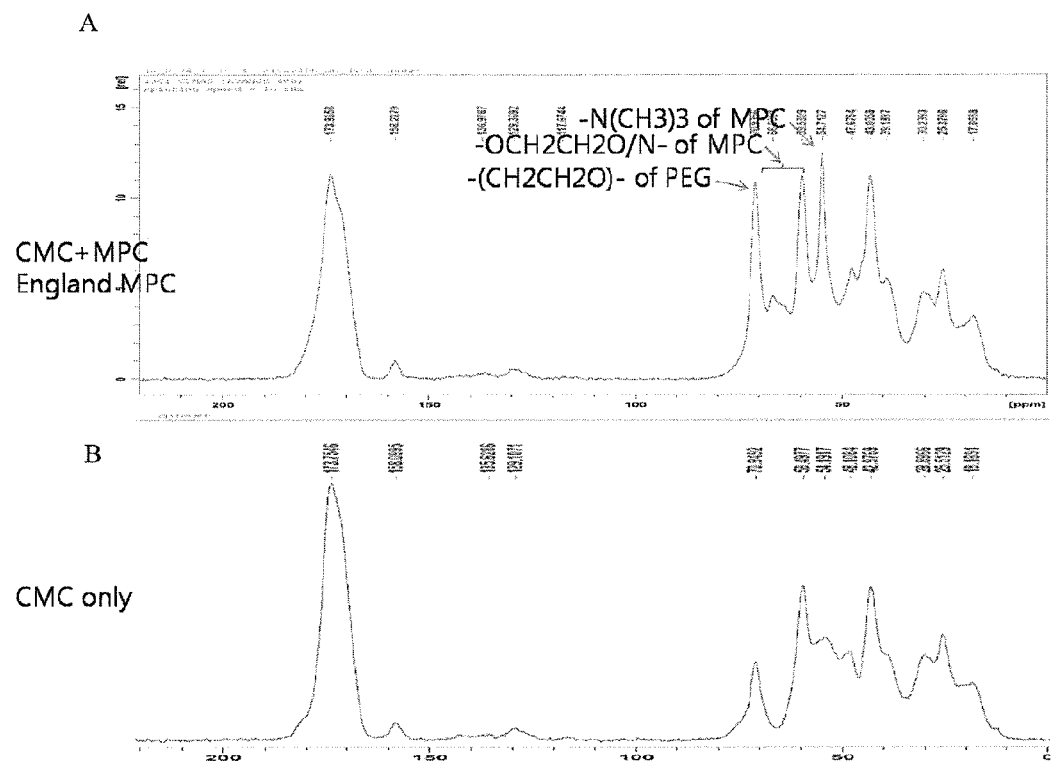
FIG. 35 illustrates solid state 13C NMR spectra.

FIG. 35 illustrates solid state $^{13}$C NMR spectra of freeze-dried RHC type III hydrogel and APS-initiated RHC type III-MPC hydrogel (collagen:MPC=2:1, w/w). NMR data was compared to confirm incorporation of MPC in the collagen hydrogels tested. The 13C and 31P NMR results indicate that the MPC was successfully incorporated into type III collagen hydrogels. Solid state 13C NMR spectra of freeze-dried APS-initiated RHC type III hydrogel incorporated MPC+CMC (A) and CMC only (B).

Figure 36:
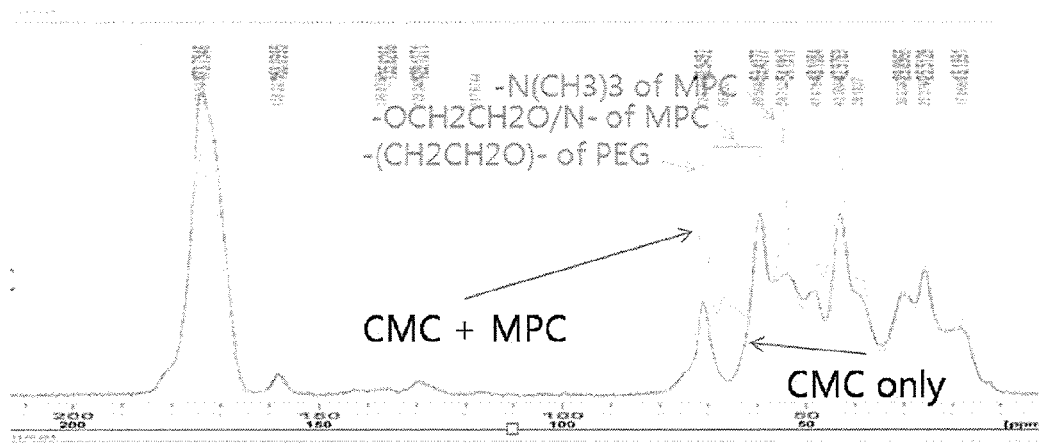
FIG. 36 is an overlapped image with 13C NMR spectra.

FIG. 36 is an overlapped image with $^{13}$C NMR spectra of type III RHC hydrogel incorporated England MPC+CMC and that crosslinked CMC only. 13C NMP spectra confirmed the incorporation of MPC into the IPNs. Peaks at 54.6 ppm and 59.6-66.5 ppm, attributed to —N(CH$_3$)$_3$ and methylene (—OCH$_2$—CH$_2$O—, —OCH$_2$CH$_2$N—) of MPC, respectively, were seen. A peak at 71 ppm indicated that PEG was also incorporated into the IPNs.

2. Collagen Hydrogel Initiated with TEMED/APS
    Initiator—TEMED/APS
    Final pH: 5.5
    Buffer used: MES
    Crosslinker of collagen: CMC/NHS
    Ratio of CMC and NHS: 1:1

Table 31 summarizes the mechanical properties of the hydrogels tested. The tensile strength, elongation at break, modulus and toughness of type III RHC collagen hydrogel initiated TEMED/APS using 18.0% collagen solution and MPC at different CMC/Coll-NH$_2$ ratios (0.4, 0.7, 1.0, 1.5) were measured. The largest value of tensile strength in all of the collagen hydrogels tested was the collagen hydrogel crosslinked by CMC with molar equivalent 0.4. Elongation at break and modulus of collagen hydrogels crosslinked by CMC had largest values at 1.0 and 1.5, respectively. No significant difference in the toughness of collagen hydrogel crosslinked by CMC was noted in any of the collagen hydrogels tested. The value of elongation at break of all collagen hydrogels was between 20% and 35%. With regard to tensile strength only, an opimal molar equivalent of CMC was 0.4 when CMC and PEGDA were used to crosslink collagen and MPC (Col.:MPC=2:1).

TABLE 31

Mechanical properties of collagen hydrogel

| Sample No. | Starting Col. % | Final Col. % | Coll/MPC (w/w) | Crosslinker/coll-NH$_2$ ratio | Tensile Strength (MPa) | Elongation at break (%) | Modulus (MPa) | Toughness (Kpa) |
|---|---|---|---|---|---|---|---|---|
| 91 | 18% | 9.4% | 2:1 | 0.4 | 2.02 ± 0.39 | 26.45 ± 5.56 | 11.00 ± 1.93 | 181.6 ± 33.5 |
| 92 | 18% | 9.2% | 2:1 | 0.7 | 1.82 ± 0.27 | 24.41 ± 7.45 | 12.89 ± 4.15 | 184.1 ± 80.2 |
| 93 | 18% | 8.8% | 2:1 | 1.0 | 1.97 ± 0.14 | 27.33 ± 3.67 | 12.63 ± 4.51 | 186.2 ± 27.7 |
| 94 | 18% | 9.1% | 2:1 | 1.5 | 1.68 ± 0.19 | 24.01 ± 7.54 | 14.45 ± 1.56 | 174.0 ± 154.8 |
| 110 | 18% | 8.5% | 1:1 | 1.0 | 1.19 ± 0.51 | 21.52 ± 6.48 | 10.51 ± 1.82 | 102.3 ± 73.8 |
| 120 | 18% | 10.2% | 4:1 | 1.0 | 1.76 ± 0.40 | 23.42 ± 7.32 | 13.59 ± 2.18 | 168.1 ± 39.7 |
| 12, 121 | 18% | 13.4% | w/o | 1.0 | 1.73 ± 0.22 | 19.45 ± 0.78 | 15.46 ± 2.41 | 119.6 ± 10.3 |

Figure 37:
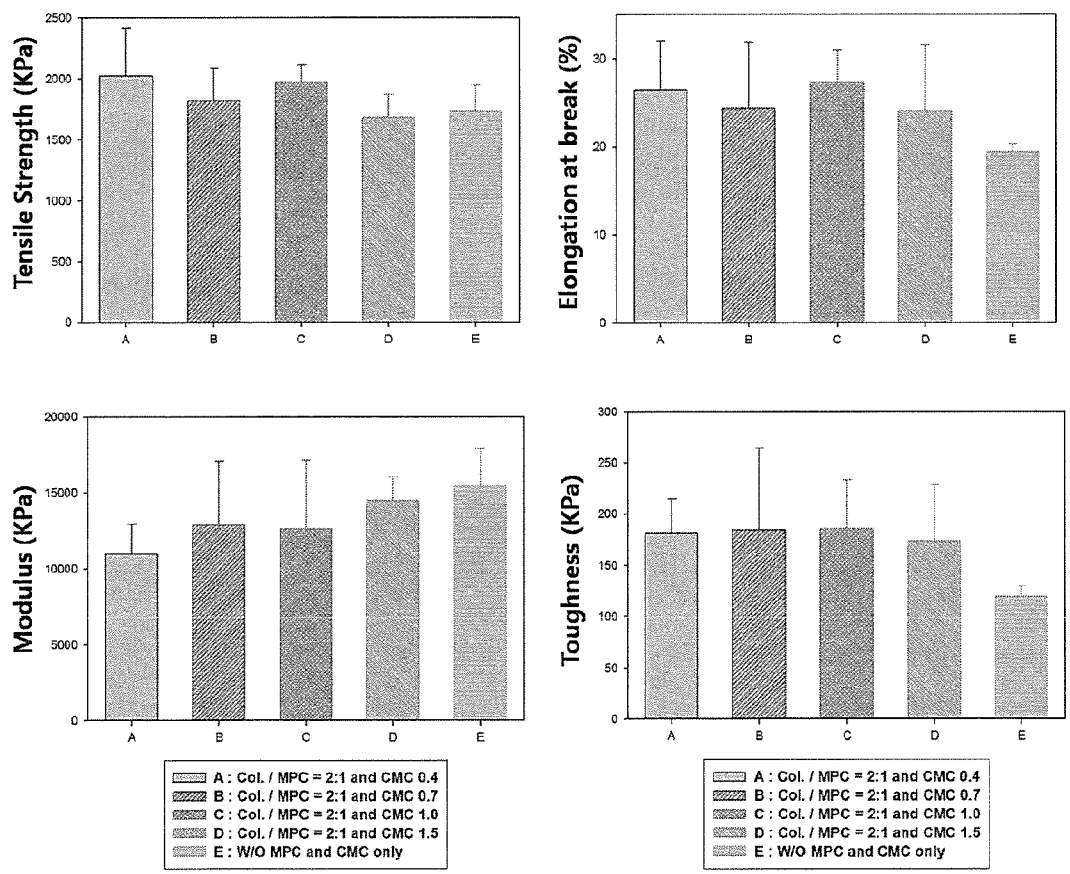
FIGS. 37 and 38 graphically illustrate mechanical properties of hydrogels.
Figure 38:
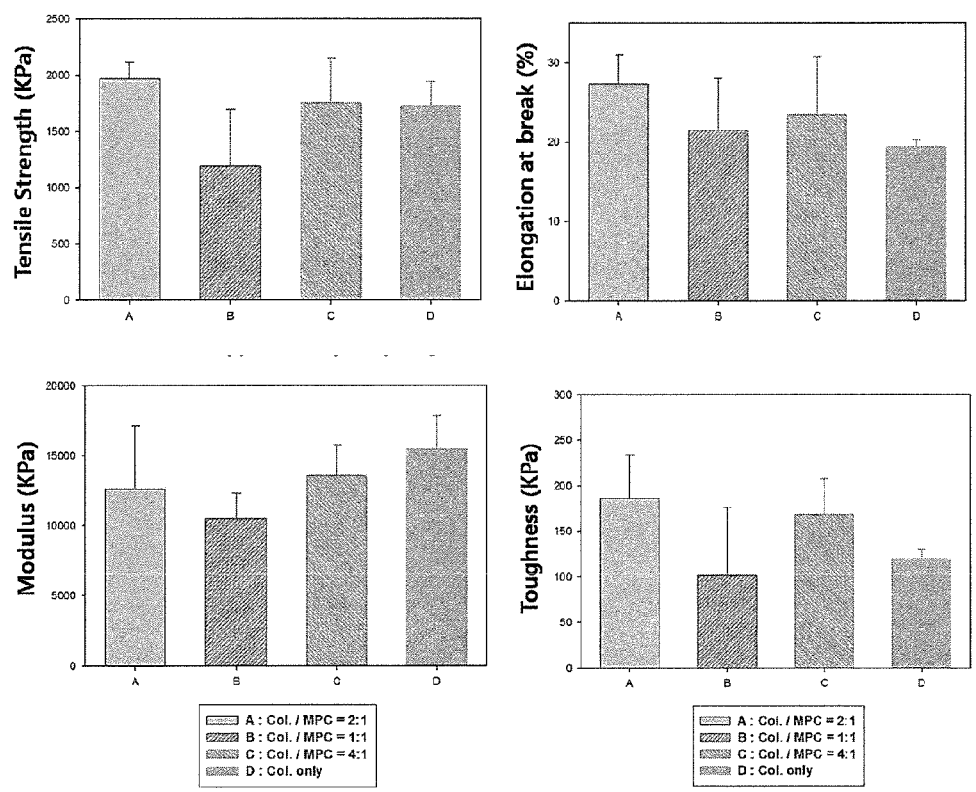

FIGS. 37 and 38 graphically illustrate mechanical properties of the hydrogels tested. The tensile strength, elongation at break, modulus and toughness of 18% RHC type III collagen hydrogel at different collagen:MPC ratios (2:1, 1:1, 4:1) were measured. The largest value of tensile strength, elongation at break and toughness in the all collagen hydrogel was the collagen:MPC ratio of 2:1. However, the modulus of collagen hydrogels were similar in value to the collagen:MPC ratios of 2:1 and 4:1 collagen hydrogels. With a collagen hydrogel crosslinked at CMC 1.0, the optimal collagen:MPC ratio was 2:1.

Water Contents & Refractive Index & DSC Data

Table 32 summarizes the water content and refractive index of the hydrogels tested. When the collagen:MPC ratio was 2:1, no significant difference in the water content of RHC hydrogels was observed. The water contents of RHC hydrogel were between 84% and 86%. When the molar equivalent of CMC was 1.0, the water content of collagen:MPC ratio 2:1 was similar to ratio 4:1, but higher than 1:1. However, the refractive index of collagen hydrogel crosslinked CMC 1.0 showed the highest value when collagen:MPC ratio was 2:1. The refractive index of RHC hydrogel were between 1.350 and 1.365. When the molar equivalent of CMC was 1.0, the refractive index of collagen: MPC ratio 2:1 was slightly higher than 1:1 and 4:1.

Figure 39:
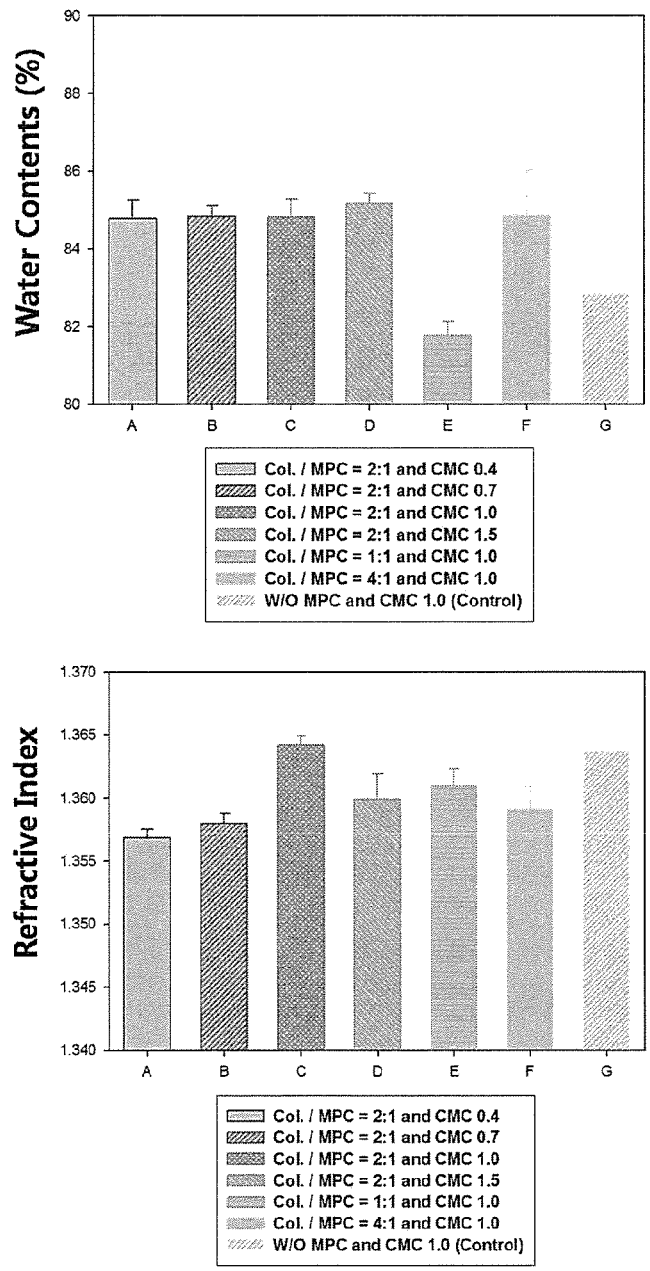
FIG. 39 graphically illustrates water content and refractive index of various hydrogels.

FIG. 39 graphically illustrates water content and refractive index of various hydrogels tested.

Figure 40:
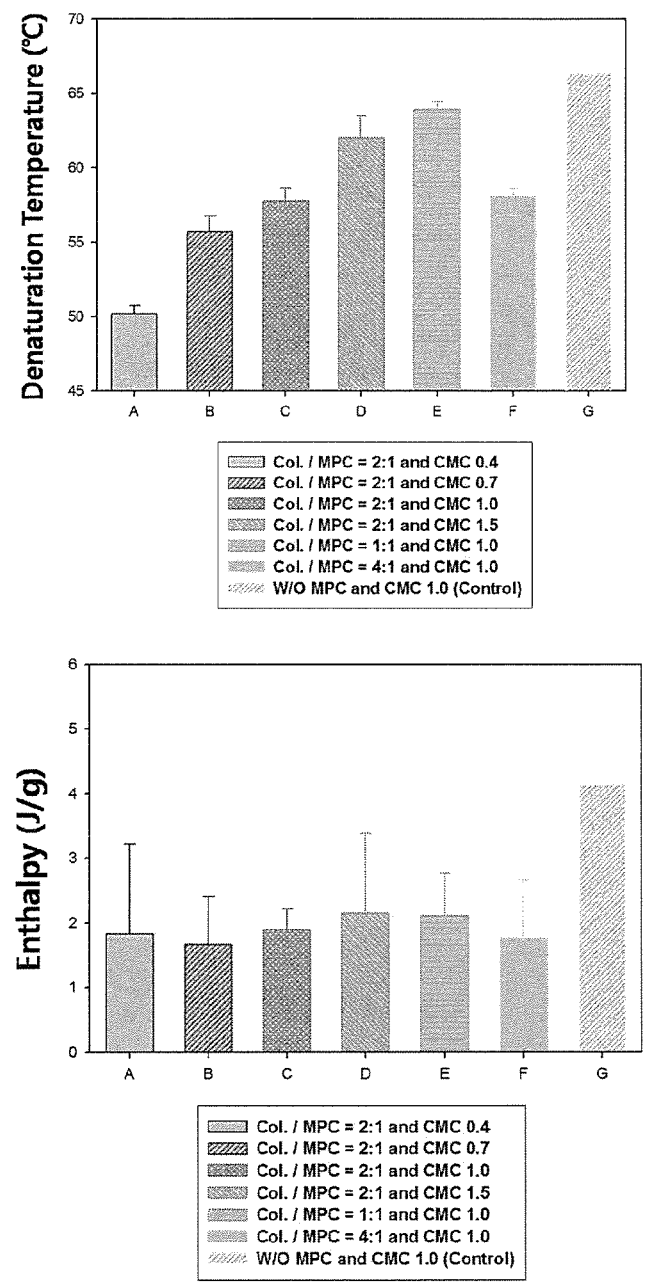
FIG. 40 graphically illustrates denaturation temperature and enthalpy of hydrogels.

FIG. 40 graphically illustrates denaturation temperature and enthalpy of various hydrogels tested. As the molar equivalent was increased, the denaturation temperature of RHC hydrogel had a tendency to increase when the collagen:MPC ratio was 2:1. The denaturation temperature and the enthalpy of collagen hydrogel using 18% RHC III were the highest in all collagen hydrogels at molar equivalent 1.5. When the molar equivalent of CMC was 1.0, the denaturation temperature of collagn:MPC ratio 1:1 was slightly higher than those of 2:1 and 4:1. The enthalpy of collagen hydrogel had a similar tendency to that of denaturation temperature. The highest values of ΔHd for collagen hydrogels used CMC at molar equivalent 1.5 in all the collagen hydrogels tested.

Collagenase Degradation

Figure 41:
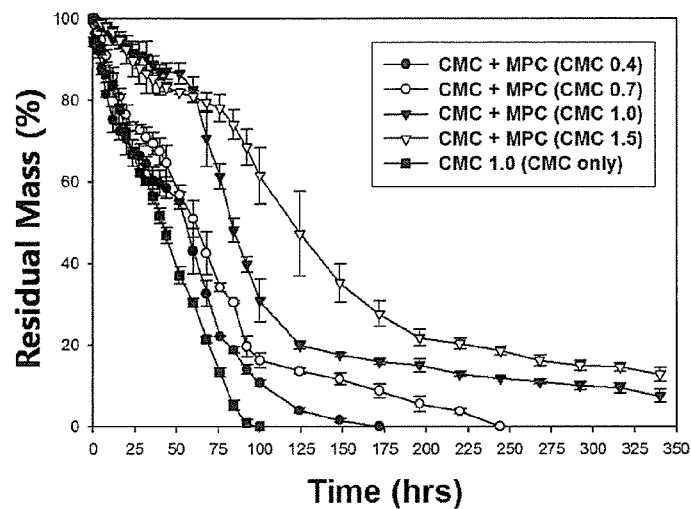
FIG. 41 graphically illustrates biodegration of various hydrogels in collagenase, in vitro.
Figure 41:
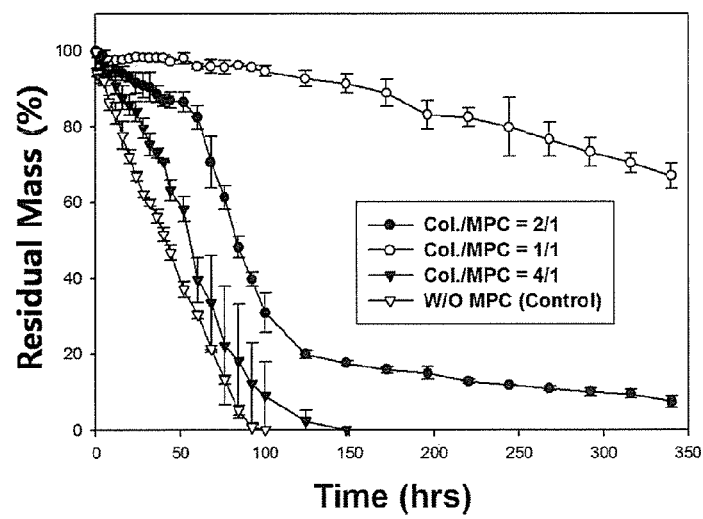

FIG. 41 graphically illustrates biodegration of various hydrogels in collagenase, in vitro. When the collagen:MPC ratio was 2:1, as the molar equivalent was increased, the collagen residual mass of RHC hydrogel had a tendency to increase. The highest values of collagen residual mass for collagen hydrogels used was at molar equivalent CMC 1.5 in all the collagen hydrogels tested. When the molar equivalent of CMC was 1.0, the collagen residual mass of collagen: MPC ratio 1:1 was much superior to 2:1 and 4:1. It was observed that MPC has an effect on the resistance of collagen hydrogel to collagenase.

Cell Biocompatibility

Figure 42:
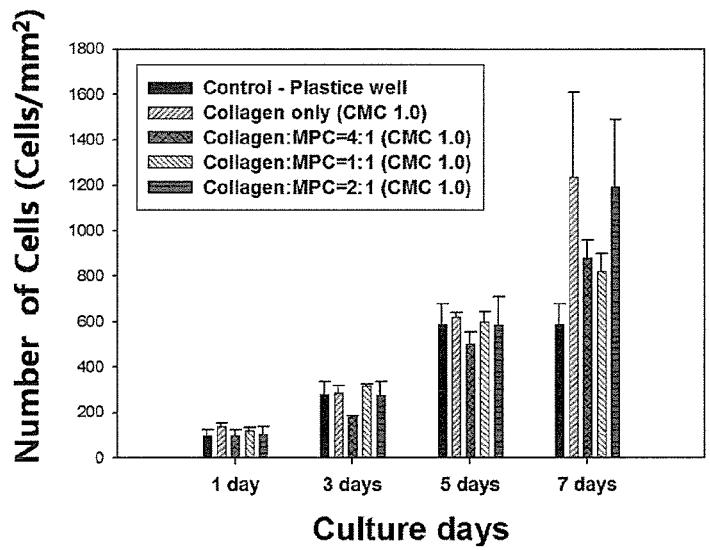
FIG. 42 graphically illustrates the number of cultivated cells in various hydrogels.
Figure 42:
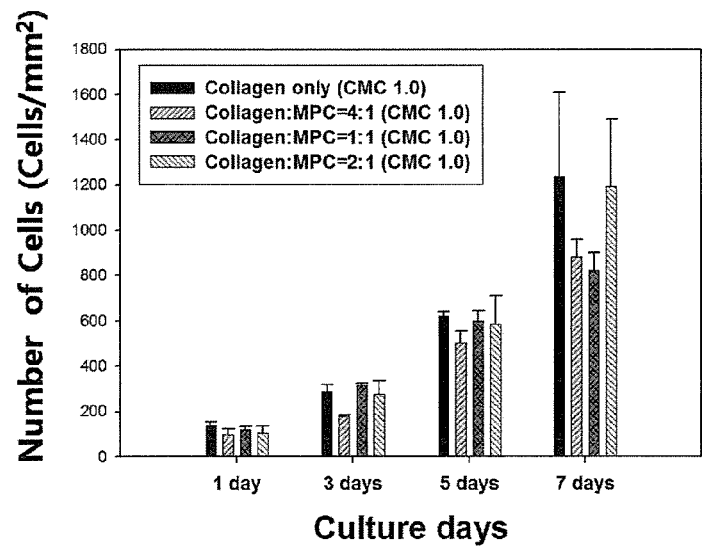

Table 33 summarizes corneal epithelial cell number cultivated on various hydrogels tested. Table 34 summarizes the confluent rate of corneal epithelial cells in various hydrogels tested. FIG. 42 graphically illustrates the number of cultivated cells in various hydrogels tested. Though MPC has known anti-adhesive properties in cells, all types of hydrogels tested successfully could be used for culturing corneal epithelial cells. Further, the corneal epithelial cells were confluent on every collagen hydrogels tested. At day 7, the number of cells cultured on hydrogel was higher than in a plastic well. Thus, all collagen/MPC hydrogels tested could be used as a substrate of corneal epithelial cells. Collagen-MPC hydrogels supported attachment and proliferation of immortalized human corneal epithelial cells and the cells reached confluence at about day 7.

TABLE 32

Water content and refractive index

| Sample No. | Coll/MPC (w/w) | Crosslinker/coll-NH$_2$ ratio | Refractive index | Water content (%) | $T_d$ (° C.) | Enthalpy (J/g) |
|---|---|---|---|---|---|---|
| 91 | 2:1 | 0.4 | 1.3568 ± 0.00070 | 84.78 ± 0.46 | 50.21 ± 0.55 | 1.83 ± 1.39 |
| 92 | 2:1 | 0.7 | 1.3580 ± 0.00083 | 84.83 ± 0.27 | 55.68 ± 1.07 | 1.67 ± 0.75 |
| 93 | 2:1 | 1.0 | 1.3642 ± 0.00064 | 84.82 ± 0.45 | 57.73 ± 0.89 | 1.89 ± 0.33 |
| 94 | 2:1 | 1.5 | 1.3599 ± 0.00206 | 85.16 ± 0.26 | 62.00 ± 1.48 | 2.15 ± 1.23 |
| 110 | 1:1 | 1.0 | 1.3609 ± 0.00133 | 81.76 ± 0.36 | 63.89 ± 0.55 | 2.11 ± 0.65 |
| 120 | 4:1 | 1.0 | 1.3591 ± 0.00183 | 84.86 ± 1.14 | 58.05 ± 0.56 | 1.76 ± 0.89 |
| 12, 121 | w/o | 1.0 | 1.3637 ± 0.00101 | 82.81 ± 0.31 | 66.34 ± 1.12 | 4.14 ± 0.25 |

TABLE 33

Corneal epithelial Cell number cultivated on the collagen gels (cells/mm$^2$)

| | Col.; MPC | Sample | Initial seeding | 1 day Ave. | 1 day Stdev. | 3 days Ave. | 3 days Stdev. | 5 days Ave. | 5 days Stdev. | 7 days Ave. | 7 days Stdev. |
|---|---|---|---|---|---|---|---|---|---|---|---|
| Plastic well | — | Control | 105 | 95.8 | 25.5 | 280 | 56 | 587.1 | 91.52 | 0 | 0 |
| Collagen only | 1:0 | 121-1 | 105 | 135.6 | 17.67 | 285 | 34.3 | 617.9 | 22.82 | 1237 | 373.6 |
| TEMED/APS | 4:1 | 120-1 | 105 | 97.2 | 24.68 | 178 | 6.84 | 504.2 | 50.2 | 878.4 | 82.15 |
| | 1:1 | 110-1 | 105 | 117.9 | 16.15 | 314 | 10.3 | 599.4 | 43.35 | 822.4 | 79.64 |
| | 2:1 | 93-1 | 105 | 106.4 | 28.45 | 276 | 58.8 | 584.9 | 124.5 | 1192 | 296.2 |

TABLE 34

Confluent rate of corneal epithelial cells (%)

| Col;MPC | Sample | 3 days | 5 days | 7 days |
|---|---|---|---|---|
| CMC only | 121-1 | 90 | 100 | 100 |
| Irgacure/UVA 4:1 | 120-1 | 70 | 90 | 100 |
| 1:1 | 110-1 | 75 | 90 | 100 |
| 2:1 | 93-1 | 75 | 95 | 100 |
| Control — | Plastic well (12 well) | 100 | 150 | — |

A summary of the optimization of CMC is shown in Table 35 and Table 36. If considering all properties tested (tensile strength, denaturation temp. collagenase degradation and biocompatibility of collagen hydrogel), the optimum molar equivalent of CMC was 1.0. and the optimum collagen:MPC ratio was 2:1. However, if resistance to collagenase degradation is the most important consideration, the optimum molar equivalent of CMC was shown to be 1.5. and the optimum collagen:MPC ratio was 1:1.

TABLE 35

Optimization of CMC molar equivalent for RHC 18% collagen hydrogel

| Collagen:MPC | Initiator System | Properties | First two good molar equivalent | Final optimum molar equivalent |
|---|---|---|---|---|
| 2:1 | Irgacure/UVA | Tensile strength | 0.4, 1.0 | 1.0 |
| | | Denaturation Temp. | 1.5, 1.0 | |
| | | Collagenase degradation | 1.5, 1.0 | |
| | | Cell biocompatibility | Good | |
| | TEMED/APS | Tensile strength | 0.4, 1.0 | 1.0 |
| | | Denaturation Temp. | 1.5, 1.0 | |
| | | Collagenase degradation | 1.5, 1.0 | |
| | | Cell biocompatibility | Good | |

TABLE 36

Optimization of Collagen: MPC ration for RHC 18% collagen hydrogel

| Molar equivalent of CMC | Initiator System | Properties | First two good ratio | Final optimum ratio |
|---|---|---|---|---|
| 1.0 | Irgacure/UVA | Tensile strength | 2:1, 1:1 | 2:1 |
| | | Denaturation Temp. | 2:1, 1:1 | |
| | | Collagenase degradation | 1:1, 2:1 | |
| | | Cell biocompatibility | 2:1, 4:1 | |
| | TEMED/APS | Tensile strength | 2:1, 4:1 | 2:1 |
| | | Denaturation Temp. | 1:1, 4:1 | |
| | | Collagenase degradation | 1:1, 2:1 | |
| | | Cell biocompatibility | 2:1, 1:1 | |

Table 37 summarizes the comparison of Irgacure and TEMED in the various hydrogels tested. Comparing the properties of collagen hydrogel when molar equivalent was 1.0 in each initiator system, the properties of collagen hydrogel initiated TEMED and APS was shown to be slightly better than those initiated with Irgacure.

TABLE 37

Comparison of collagen hydrogel properties initiated Irgacure and TEMED/APS

| Initiator system for MPC | Irgacure/UVA | TEMED/APS |
|---|---|---|
| Sample No. | 107 | 93 |
| Starting collagen % | 18 | 18 |
| Final collagen % | 9.8 | 8.8 |
| Crosslinker/coll-NH2 ratio | 1.0 | 1.0 |
| Tensile Strength (MPa) | 1.82 ± 0.32 | 1.97 ± 0.14 |
| Elongation at break (%) | 24 ± 2.77 | 27.33 ± 3.67 |
| Modulus (MPa) | 14.38 ± 2.74 | 12.63 ± 4.51 |
| Toughness (Kpa) | 175.7 ± 65.7 | 186.2 ± 27.7 |
| Refractive index | 1.3561 ± 0.00062 | 1.3642 ± 0.00064 |
| Td (° C.) | 62.74 ± 1.40 | 57.73 ± 0.89 |
| Water content (%) | 85.97 ± 0.15 | 84.82 ± 0.45 |
| Collagenase (hrs) (Time when residual mass was 20%) | 100 | 112 |

Example 7

RHC Type III Collagen Hydrogel Containing ACV(Acyclovir) Encapsulated Silica

Collagen:

1. 13.7% RHC Type III collagen (0.25% vs. 0.50% Si+ACV/collagen)

2. 13.7% RHC Type III collagen (0.50% Si+ACV/collagen)

1. $1^{st}$ Silica-ACV

A collagen hydrogel containing two times ACV content was made to release more ACV than gels produced previously [24]. The tensile strength of collagen hydrogel with 0.9 mg ACV added was slightly stronger than that of collagen hydrogel with 1.8 mg ACV added. The white light transmission of the 0.9 mg ACV/g hydrogel was about 87%, compared to about 76% for 1.8 mg ACV/g hydrogel. The ACV release of the 1.8 mg ACV was about two times of that of 0.9 mg ACV hydrogel. However, ACV released very quickly. Therefore, there is a need to develop slower releasing silica-ACV hydrogels.

2. $2^{nd}$ Silica-ACV

Collagen hydrogels containing freshly-prepared ("new") and previously-prepared ("old") silica-ACV were made. In addition, collagen hydrogels containing water only and silica only were prepared to compare to the silica-ACV hydrogels. Tensile strength, transmission and ACV release were measured. The tensile strength of the collagen hydrogel containing new silica-ACV had the highest values amongst all collagen hydrogels tested. The white light transmission of the collagen hydrogel containing old silica-ACV was about 75%. However, the collagen hydrogel containing new silica-ACV was about 70%.

The new silica-ACV appeared to raise the pH of collagen solution. Therefore, the tensile strength of collagen hydrogel containing the new silica-ACV was slightly higher than that of the old silica-ACV. The transmission of the new silica- ACV was slightly lower than that of the old silica-ACV. The accumulated ACV release of the old silica-ACV was higher than that of the new silica-ACV.

Though the collagen hydrogel had a problem of fast ACV release early on, the collagen hydrogel containing ACV in silica and cross-linked with CMC shows promise as an alternative to patients with herpes simplex virus (HSV)-infected corneas.

Method and Results 1. 1$^{st}$ Silica-ACV hydrogel

TABLE 38

| | Method | | |
|---|---|---|---|
| Order | Component & method | Mixing time | Mixing Temp. (° C.) |
| 1 | Collagen + H$_2$O | 30 | 0 |
| 2 | +MPC (100 μL) | 30 | 0 |
| 3 | +PEG (13.4 μL) | 30 | 0 |
| 4 | +IRGAcure (100 μL) | 30 | 0 |
| 5 | +NHS (10 μL) | 30 | 0 |
| 6 | +Silica-ACV (300 μL) | 40 | 0 |
| 7 | Wait - 10 min. | | 25 |
| 8 | +CMC (10 μL) | 30 | 25 |
| 9 | | 20 | 0 |
| 10 | UV crosslink | 15 minutes | Room Temp. |

TABLE 39

| | | | Experimental Conditions | | | | | |
|---|---|---|---|---|---|---|---|---|
| CMC | starting collagen % | Buffer used | coll/MPC ratio | PEG/MPC ratio | IRGAcure w/v % | NHS/CMC ratio | Final collagen % | Si + ACV/ collagen % |
| 0.4 | 13.7 | H$_2$O | 2:1 | 1:3 | 0.5 | 1:1 | 7.2% | 0.25 |
| 0.4 | 13.7 | H$_2$O | 2:1 | 1:3 | 0.5 | 1:1 | 7.2% | 0.50 |

Figure 43:
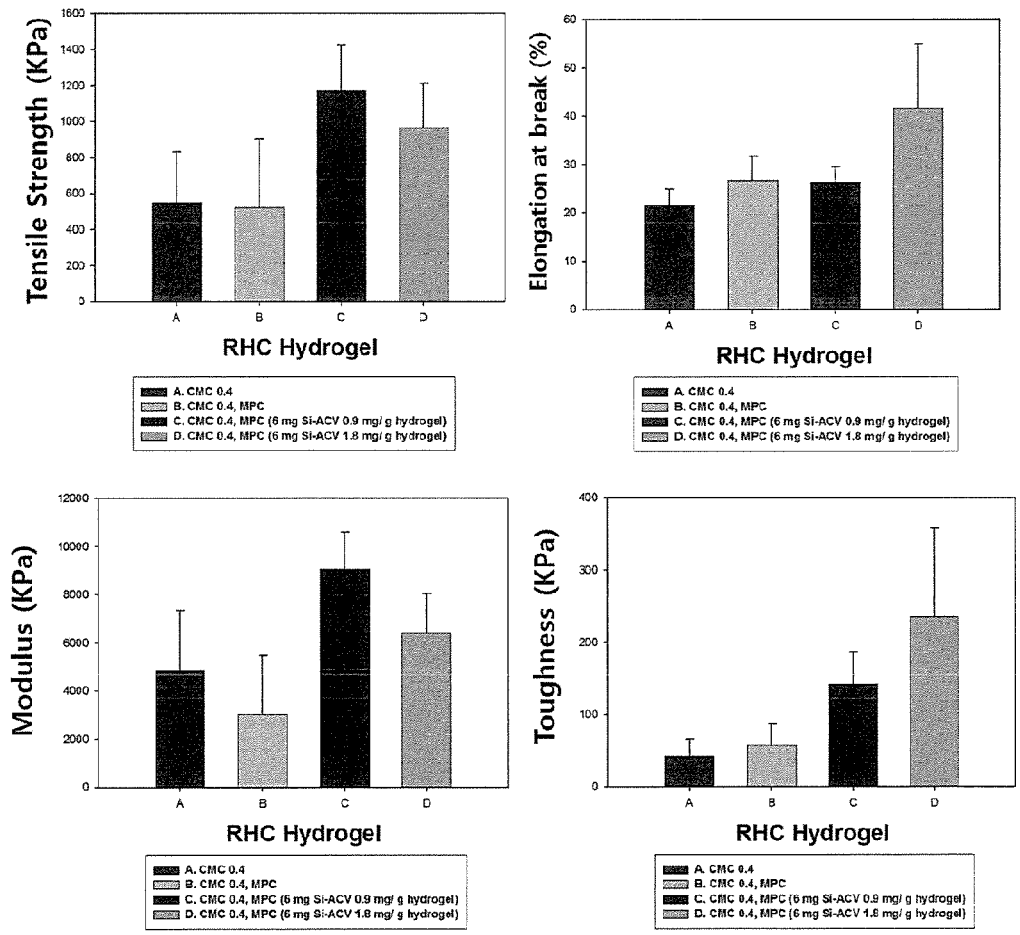
FIG. 43 illustrates mechanical properties of hydrogels.

The mechanical properties of the collagen hydrogels were measured as summarized in Table 40. The tensile strength, elongation at break, modulus and toughness of type III recombinant human collagen hydrogels at 13.7% solution concentration, CMC/MPC and ACV contents are illustrated in FIG. 43.

The tensile strength of collagen hydrogels tested (C, D) was stronger than those in control groups (A, B), though 0.3 ml water was added to the collagen hydrogels with ACV encapsulated silica (C, D). The modulus of collagen hydrogel had a tendency similar to the tensile strength. The value of elongation at break of all collagen hydrogels was between 20% and 50%. The collagen hydrogels made by MPC, PEG and CMC in 13.7% and the collagen hydrogels made by ACV 0.9 mg/g hydrogel CMC(C) and by ACV 1.8 mg/g hydrogrogel CMC (D) had the best value of toughness.

Figure 44:
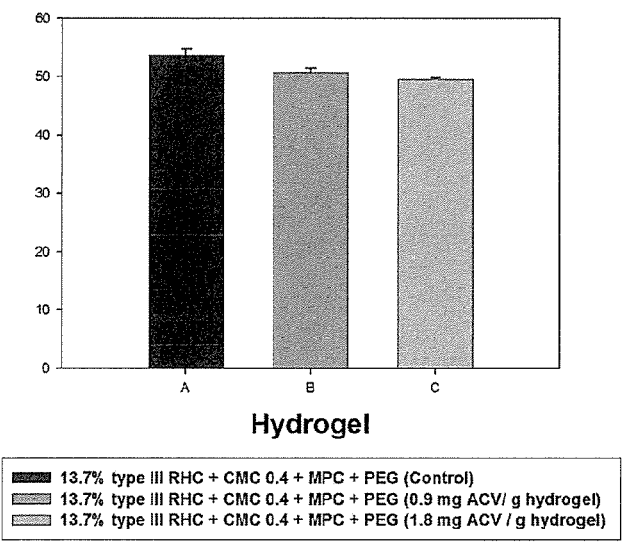
FIG. 44 illustrates denaturation temperature and the enthalpy of collagen hydrogels.
Figure 44:
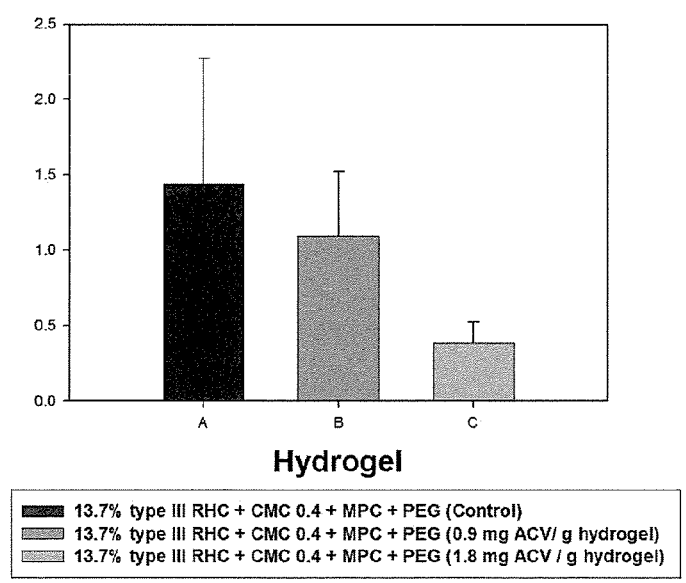

Table 40 also summarizes the denaturation temperature and the enthalpy of collagen hydrogels tested, and illustrated graphically in FIG. 44. At CMC molar equivalent 0.4 (A, control), the denaturation temperature was highest amongst all three of the collagen hydrogels.

Figure 45:
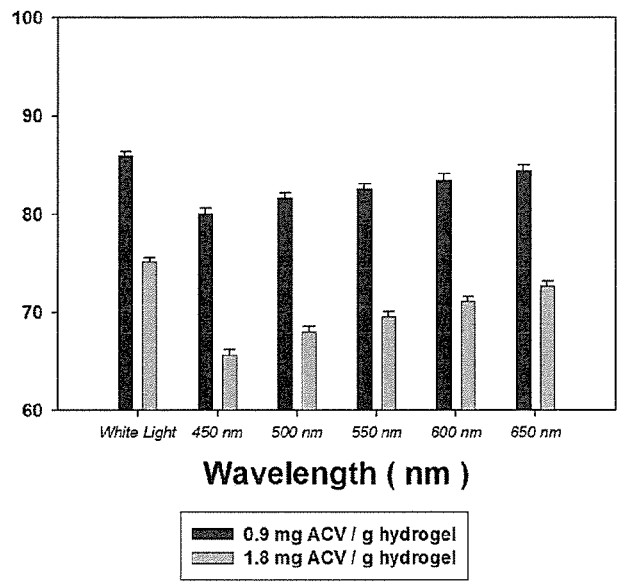
FIG. 45 illustrates transmission and ACV release in the collagen hydrogels.
Figure 45:
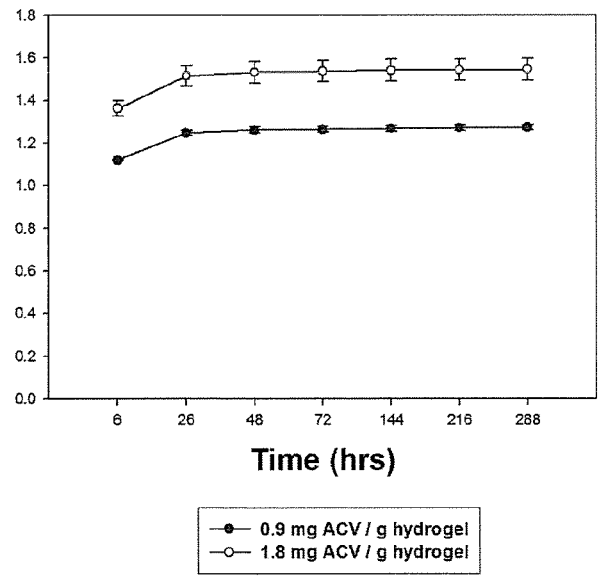

FIG. 45 illustrates transmission and ACV release in the collagen hydrogels tested. The collagen hydrogel cross-linked CMC with ACV 0.9 mg/g hydrogel was not particularly cloudy. However, the collagen hydrogel with ACV 1.8 mg/g hydrogel was slightly cloudy. White light transmission of collagen hydrogels with 0.9 mg ACV/g hydrogel was higher than that of the 1.8 mg ACV/g hydrogel at all wavelengths. The white light transmission of the collagen hydrogel with ACV 0.9 mg/g hydrogel was about 87%. However, the collagen hydrogel with ACV 1.8 mg/g hydrogel was about 76%. The ACV release was measured in about 100 mg hydrogel sample was submerged in 1 ml PBS at 37° C.

2. 2$^{nd}$ Silica-ACV Hydrogel

TABLE 41

| | Method | | |
|---|---|---|---|
| Order | Component & method | Mixing time | Mixing Temp. (° C.) |
| 1 | Collagen + H$_2$O | 30 | 0 |
| 2 | +MPC(100 μL) | 30 | 0 |

TABLE 41-continued

| | Method | | |
|---|---|---|---|
| Order | Component & method | Mixing time | Mixing Temp. (° C.) |
| 3 | +PEG (13.4 μL) | 30 | 0 |
| 4 | +IRGAcure (100 μL) | 30 | 0 |
| 5 | +NHS (10 μL) | 30 | 0 |
| 6 | +Silica-ACV (300 μL) | 40 | 0 |
| 7 | Wait - 10 min. | | 25 |
| 8 | +CMC (10 μL) | 30 | 25 |
| 9 | | 20 | 0 |
| 10 | UV crosslink | 15 minutes | Room Temp. |

TABLE 40

| | | | Results | | | | |
|---|---|---|---|---|---|---|---|
| Si + ACV/ collagen % | Tensile Strength (KPa) | Elongation at Break % | Modulus (MPa) | Toughness (MPa) | Transmission | Denature Temp. | Enthalpy |
| 0.25 | 1173 ± 251 | 26.3 ± 3.2 | 9064 ± 1527 | 141.8 ± 44.4 | 85.9 ± 0.475 | 50.8 ± 0.63 | 1.10 ± 0.43 |
| 0.50 | 966 ± 246 | 41.7 ± 13.2 | 6420 ± 1627 | 235 ± 121.9 | 75.2 ± 0.395 | 49.6 ± 0.23 | 0.39 ± 0.14 |

TABLE 42

| | | | | Experimental Conditions | | | | |
|---|---|---|---|---|---|---|---|---|
| Si + ACV/ collagen % | CMC | starting collagen % | Buffer used | coll/MPC ratio | PEG/MPC ratio | IRGAcure w/v % | NHS/CMC ratio | Final collagen % |
| 0.50-H$_2$O only | 0.4 | 13.7 | H$_2$O | 2:1 | 1:3 | 0.5 | 1:1 | 7.2% |
| 0.50-Si only | 0.4 | 13.7 | H2O | 2:1 | 1:3 | 0.5 | 1:1 | 7.1% |
| 0.50-New Si-ACV | 0.4 | 13.7 | H2O | 2:1 | 1:3 | 0.5 | 1:1 | 7.0% |
| 0.50-Old Si-ACV | 0.4 | 13.7 | H2O | 2:1 | 1:3 | 0.5 | 1:1 | 7.1% |

Figure 46:
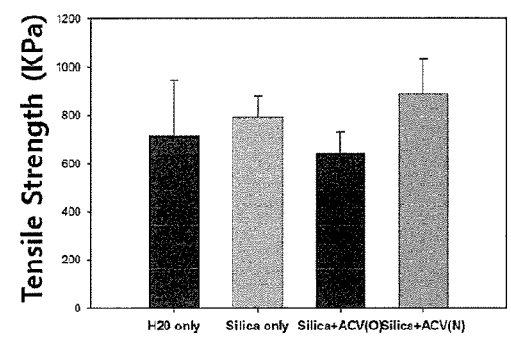
FIG. 46 illustrates mechanical properties of hydrogels.
Figure 46:
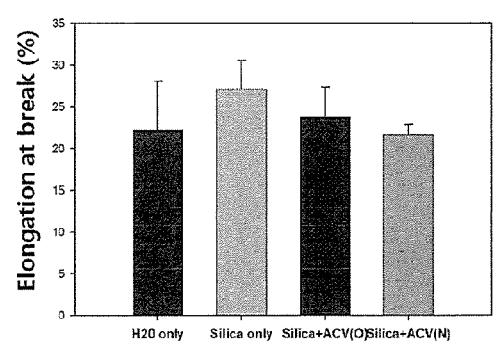
Figure 46:
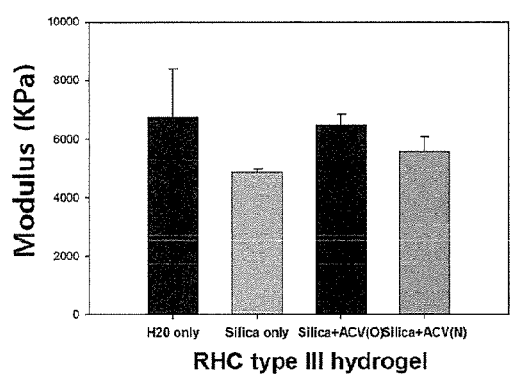
Figure 46:
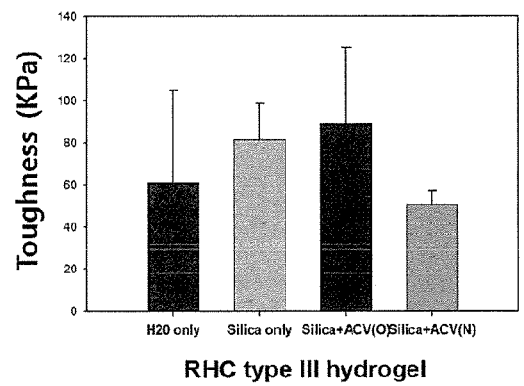

The mechanical properties of the collagen hydrogels were measured as summarized in Table 43. The tensile strength, elongation at break, modulus and toughness of the hydrogels testes are illustrated in FIG. 46.

TABLE 43

| | | Results | | |
|---|---|---|---|---|
| Si + ACV/ collagen % | Tensile Strength (KPa) | Elongation at Break % | Modulus (KPa) | Toughness (KPa) |
| 0.50-H$_2$O only | 717.2 ± 228.1 | 22.22 ± 5.83 | 6749 ± 1639 | 61 ± 43.67 |
| 0.50-Si only | 793.3 ± 85 | 27.11 ± 3.42 | 4862 ± 100 | 81.42 ± 17.07 |
| 0.50-New Si-ACV | 889.6 ± 144.5 | 23.78 ± 3.58 | 6491 ± 330 | 89 ± 35.9 |
| 0.50-Old Si-ACV | 641.8 ± 86.9 | 21.67 ± 1.16 | 5578 ± 494 | 50.73 ± 6.39 |

Collagen hydrogels containing freshly-prepared ("new") and previously-prepared ("old") silica-ACV were made. In addition, collagen hydrogels containing water only and silica only were prepared to compare to the silica-ACV hydrogels. Tensile strength, transmission and ACV release were measured. The tensile strength of the new silica-ACV was the highest amongst all collagen hydrogels tested. The value of elongation at break of all collagen hydrogels (orthogonal direction to cast) was between 20% and 30%. The collagen hydrogels containing silica-ACV were cloudier than those in the control group. In particular, the new silica-ACV was somewhat cloudier than the old silica-ACV.

Figure 47:
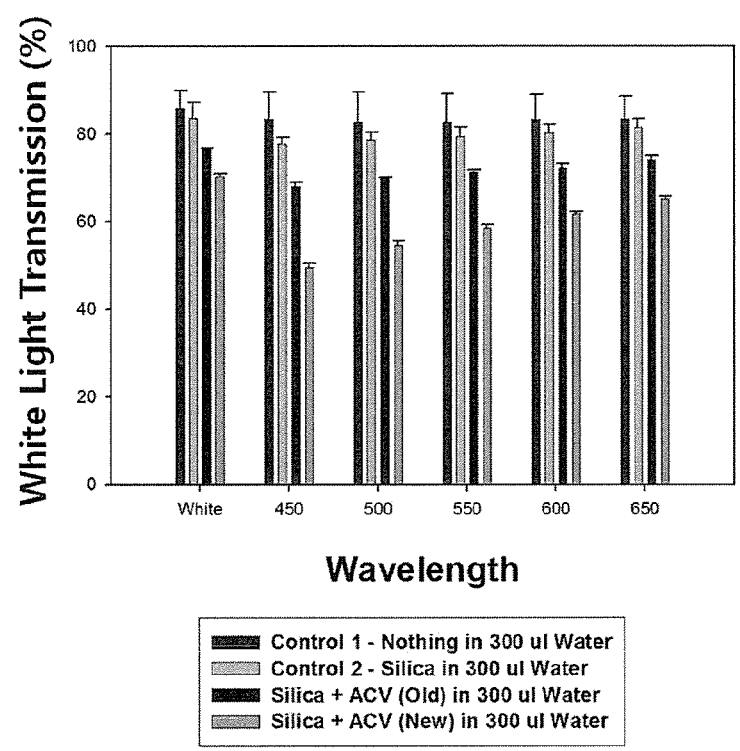
FIG. 47 illustrates the white light transmission of hydrogels.
Figure 48:
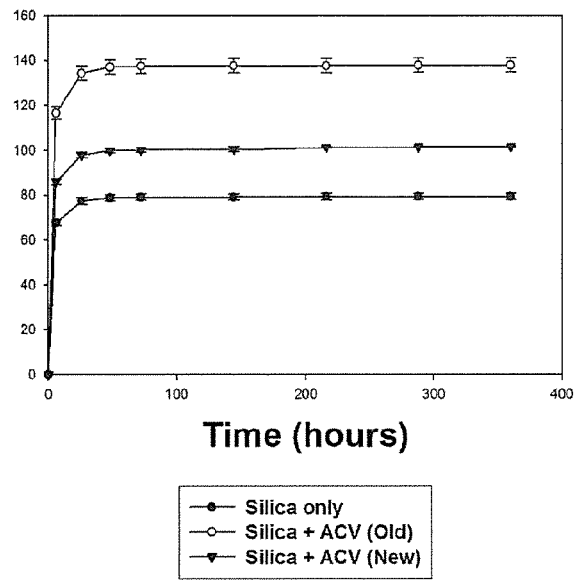
FIG. 48 illustrates ACV release in hydrogels.
Figure 48:
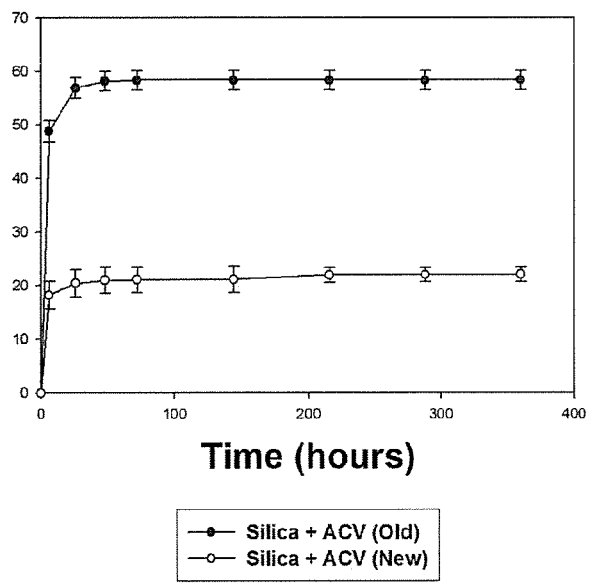

FIG. 47 illustrates the white light transmission of the hydrogels tested. White light transmission of the old silica-ACV was higher than that of the new silica-ACV. The white light transmission of the old silica-ACV was about 75%. However, the new silica-ACV was about 70%. The new silica-ACV appeared to raise the pH of the collagen solution. Therefore the tensile strength of the new silica-ACV was slightly higher than the old silica-ACV. The transmission of the new silica-ACV was slightly lower than the old silica-ACV.
ACV Release FIG. 48 illustrates ACV release in the hydrogels tested. The accumulated ACV release of the old silica-ACV was higher than that of the new silica-ACV. After subtracting the silica only value, the old silica-ACV was three times higher than that of the new silica-ACV in the contents of accumulated ACV release. Of note, the addition of new silica-ACV in collagen solution was particularly difficult, as well as obtaining a collagen hydrogel with uniformly dispersed silica-ACV.

The content of ACV releasing was measured by HPLC. The concentration of ACV was 0.040±0.008 mM (0.034, 0.047, 0.038 mM). This calculated the contents of ACV to be 8.93 µg/1 ml PBS or 14.5 µg ACV/mg silica. There was little difference (3.5 ACV/mg silica) between $3^{rd}$ ACV result value (18 ACV/mg silica) and $4^{th}$ ACV result (14.5 ACV/mg silica).

Example 8

Pre-CMC Crosslinked RHC Type III Collagen Hydrogel Crosslinked by UVA-Riboflavin Collagen:
18.0% RHC Type collagen Keratoconus forms an important proportion of patients with corneal diseases. However, the pathogenesis is not well understood; thus, there is currently no treatment apart from transplantation. In recent work, corneal collagen cross-linking consists of a photopolymerization of stromal collagen fibers induced by the combined action of a photosensitizing substance and UVA light that induces corneal stiffening by increasing the number of intrafibrillar and interfibrillar covalent bonds and corneal collagen resistance against enzymatic degradation [25,26]. This riboflavin treatment is to create additional chemical bonds inside cornea by means of photopolymerization. Riboflavin acts as a photomediator, creating free radicals to induce new chemical bonds in cornea. This collagen cross-linking of riboflavin and UVA has been successful minimizing the progression of keratoconus.

In the present example, the photopolymerization technique was applied in making collagen hydrogels. When the molar equivalent of CMC was low (0.4), the tensile strength, denaturation temperature and collagenase degradation of collagen hydrogel treated by the photo crosslinker was much superior to those not treated with the photo crosslinker. However, when the molar equivalent of CMC was high (0.7), there was not a big difference between the properties of collagen hydrogel treated with photo crosslinker and those not treated therewith. Without wishing to be bound by theory, this difference may be explained due to the fact there were still free radicals to cross-link in collagen hydrogel with a cross-linked 0.4 molar ratio of CMC. On the other hand, there were not many free radicals to cross-link in collagen hydrogel with cross-linked 0.7 molar ratio of CMC.

Therefore, a low molar ratio CMC cross-linked collagen hydrogel should be used the UVA-riboflavin crosslinker to improve the properties of collagen hydrogel.

Method and Results

TABLE 44

| | Method | | |
|---|---|---|---|
| | Contents | Quantity | Mixing time |
| 1 | RHC III | 550 mg | |
| 2 | $H_2O$ | 150 μL | 30 |
| 3 | +NHS | 10 μL | 10 |
| 4 | CMC | 15 μL | 30 |
| 5 | Plating and curing | 1 day | |
| 6 | Washing | 7 days | |
| 7 | 0.1% Riboflavin in 20% dextran & 3 mW/cm²UVA | 30 minutes | |

The pre-CMC crosslinked hydrogel was post-treated with riboflavin and UVA. 0.1% riboflavin solution in 20% dextran was instilled onto the hydrogel every 3 minutes for 30 minutes. Irradiance of UVA was 3 mW/cm². Tensile strength, denaturation temp., and in vitro collagenase biodegradation data were measured and summarized in Table 45.

TABLE 45

| | | Results | | |
|---|---|---|---|---|
| | | | Properties | |
| Cross-link | | Tensile strength | Collagenase degradation (When residual mass was 20% of original mass) | Denaturation Temp. |
| CMC | Riboflavin | (Kpa) | (hrs) | (° C.) |
| 0.4 | UVA o | 3052 ± 144 | 50 | 65.17 ± 0.40 |
| | UVA x | 2420 ± 859 | 33 | 58.04 ± 1.23 |
| 0.7 | UVA o | 2990 ± 489 | 43 | 61.35 ± 0.83 |
| | UVA x | 3218 ± 562 | 49 | 64.32 ± 2.34 |

When the molar equivalent of CMC was low (0.4), the tensile strength, denaturation temperature and collagenase degradation of collagen hydrogel treated with the photo crosslinker were superior to those not treated with photo crosslinker. However, when the molar equivalent of CMC was high (0.7), the tensile strength, denaturation temperature and collagenase degradation of collagen hydrogel not treated with photo crosslinker was slightly better than those treated therewith.

In sum, the present example illustrates that second photo polymerization can improve the properties of pre-CMC cross-linked collagen hydrogels. In particular, the properties of collagen hydrogel cross-linked with the low molar ratio of CMC were superior to those with the higher molar ratio. The lower molar equivalent of crosslinker tended to exhibit a slower gelation time of the collagen hydrogels. The collagen hydrogel cross-linked with CMC had a longer gelation time than that cross-linked with EDC. The slower gelation time is one advantage which may prove beneficial for using CMC-treated hydrogels to treat keratoconus patients.

Treatment of the collagen hydrogel with photo polymerization prior to CMC cross-linking appears to improve the properties of the collagen hydrogel.

REFERENCES

[1] Griffith, M., R. Osborne, R. Munger, X. Xiong, C. J. Doillon, N. L. C. Laycock, M. Hakim, Y. Song, and M. A. Watsky (1999) Functional human corneal equivalents constructed from cell lines. Science 286: 2169-2172.

[2] Tsai, R. J., L. Li, B. S. Chen, and J. Chen (2000) Reconstruction of damaged corneas by transplantation of autologous limbal epithelial cells. New England J. Medicine 343:86-93.

[3] Whitcher J P, Scrinivasan M, Upadhyay M P. Prevention of corneal ulceration in the developing world. Int Ophthalmol Clin 2002; 42:71e7.

[4] Carlsson D J, Li F, Shimmura S, Griffith M. Bioengineered corneas: how close are we? Curr Opin Ophthalmol 2003; 14:192e7.

[5] Merrett et al. Tissue engineered recombinant human collagen-based corneal sunstitutes for implantation: performance of type I versus type III collagen. Inves Opthalmol V is Sci. 2008; 49:3887-3894.

[6] Li et al. Cellular and nerve regeneration within a biosynthetic extracellular matrix for corneal transplantation. PNAS USA 2003; 1001:15346-15351.

[7] Rafat et. al. PEG-stabilized carbodiimide crosslinked collagen-chitosan hydrogels for corneal tissue engineering. Biomaterials. 2008 October; 29(29):3960-72.

[8] Liu W et al., Collagen—phosphorylcholine interpenetrating network hydrogels as corneal substitutes, Biomaterials (2009), doi:10.1016/j.biomaterials.2008.11.022.

[9] Liu Y, Gan L, Carlsson D J, Fagerholm P, Lagali N, Watsky M A, et al. A simple, cross-linked collagen tissue substitute for corneal implantation. Invest Ophthalmol V is Sci 2006; 47(5):1869e75.

[10] Priest D, Munger R. A new instrument for monitoring the optical properties of corneas. Invest Ophthalmol V is Sci 1998; 39(Suppl):s352.

[11] Zeng Y, Yang J, Huang K, Lee Z, Lee X. A comparison of biomechanical properties between human and porcine cornea. J Biomech 2001; 34:533e7.

[12] Huang-Lee L L H, Cheung D T, Nimni M E. Biochemical changes and cytotoxicity associated with the degradation of polymeric glutaraldehyde derived crosslinks. J Biomed Mater Res 1990; 24:1185-201

[13] Doillon C J, Cote M F, Pietrucha K, Laroche G, Gaudreault R C. Porosity and biological properties of polyethylene glycol-conjugated collagen materials. J iomater Sci Polym Ed 1994; 6(8):715-28

[14] Chvapil M, Speer D, Mora W, Eskelson C. Effect of tanning agent on tissue reaction to tissue implanted collagen sponge. J Surg Res 1983; 35:402-9

[15] Zeeman R, Dijkstra J, Van Wachem P B, Van Luyn M J, Hendriks M, Cahalan P T, et al. Successive epoxy and carbodiimide cross-linking of dermal sheep collagen. Biomaterials 1999; 20:921-31

[16] Damink L H H O et al. Cross-linking of dermal sheep collagen using a water-soluble carbodiimide. Biomaterials 1996; 17:765-63.

[17] Nimni M E, Cheung d, Strates B, Kodama M, Skeikh K. Chemically modified collagen: a natural biomaterial for tissue replacement. J Biomed Mater Res 1987; 21:741-71.

[18] Chvapil M, Speer D, Mora W, Eskelson C. Effect of tanning agent on tissue reaction to tissue implanted collagen sponge. J Surg Res 1983; 35:402-9.

[19] Hardy P M, Nicholls A C, Rydon H N, The nature of the crosslinking of proteins by glutaraldehyde. Part 1. Interaction of glutaraldehyde with the amino groups of 6-amino hexanoic acid and of —N-acetyl-lysine. J Chem Soc, Perkin Trans 11976; 958-62.

[20] Hardy P M, Hughes G J, Ryson H N, The nature of the crosslinking of proteins by glutaraldehyde. Part 2. The formation of quaternary pyridinium compounds by the action of glutaraldehyde on proteins and the identification of a 3-(2-piperidyl)-pyridinium derivative, anabilysine, as a crosslinkg entity. J Chem Soc, Perkin Trans 11978; 2282-2288.

[21] Traubel H. Gerbung mit Isocyanaten, 1. Teil. Das leder 1977; 11:150-4.

[22] Eybel E, Griesmacher A, Grimm M, Wolner E. Toxic effects of aldehydes released rom fixed periocardium on bovine aortic endothelial cells. J Biomed Mater Res 1989; 23:1355-65.

[23] Hey Kb, Lachs C M, Raxworthy M J Wood Ej. Crosslinked fibrous collagen for the use as a dermal implant:control of the cytotoxic effects of glutaraldehyde and dimethylsuberimidate. Biotechnol Appl Biochem 1990; 12:85-93.

[24] Zeeman R, Dijkstra P J, Van Wachem P B, Van Luym M J, Hendriks M, Cahalan P T, et al Successie epoxy and carbodiimide cross-linking of dermal sheep collagen. Biomaterials 1999:20:921-31

[25] Weadock K, Olson R M, Silver F H. Evaluation of collagen crosslinking techniques. Biomater Med Dev Artif Organs 1983-84; 11:293-318

[26] Van Wachem P B, Planting a JA, Wissink M J. Beernink R, Poot A A, Engbers G H, et al. In vivo biocompatibility of carbodiimide-crosslinkg collagen scaffolds: effects of crosslink density, heparin immobilization and bFGF lading. J Biomed Mater Res 2001; 55:368-78.

[5a] Li F, Carlsson D, Lohmann C, Suuronen E, Vascotto S, Kobuch K, et al. Cellular and nerve regeneration within a biosynthetic extracellular matrix for corneal transplantation. Proc. Natl. Acad. Sci. (PNAS) USA 2003; 100(26): 15346-51.

[6a] Li F, Griffith M, Li Z, Tanodekaew S, Sheardown H, Hakim M. Carlsson D J. Recruitment of multiple cell lines by collagen-synthetic copolymer matrices in corneal regeneration. Biomaterials 2005; 26(16):3093-104.

[7a] Liu W, Deng C, McLaughlin C R, Fagerholm P, Lagali N S, Heyne B et al., Collagen-phosphorylcholine interpenetrating network hydrogels as corneal substitutes, Biomaterials 2009; 30(8): 1551-9.

[13a] Olde Damink L H, Dijkstra P J, van Luyn M J, van Wachem P B, Nieuwenhuis P, Feijen J. Cross-linking of dermal sheep collagen using a water-soluble carbodiimide. Biomaterials 1996; 17(8):765-73.

[19a] Petite H, Rault I, Hue A, Menasche P, Herbage D. Use of the acyl azide method for cross-linking collagen-rich tissue such as pericardium. J Biomed Mater Res. 1990; 24(2):179-87

[20] Liu Y, Gan L, Carlsson D J, Fagerholm P, Lagali N, Watsky M A, et al. A simple, cross-linked collagen tissue substitute for corneal implantation. Invest Ophthalmol V is Sci 2006; 47(5):1869-75.

[21] Maurice D M. The eye. In: Dayson H, editor. New York: Academic Press Inc; 1962. p. 296.

[22] Patel S, Marshall J, Fitzke III F W. Refractive index of human corneal epithelium and stroma. J Refract Surg 1995; 11:100e5.

[23] Beems E M, Best W. Light transmission of the cornea in whole human eyes. Exp Eye Res 1990; 50:393e5.

[24] Bareiss B, Ghorbani M, Li F, Blake J A, Scaiano J C, Zhang J, Deng C, Merrett K, Harden J L, Francisco Diaz-Mitoma F, Griffith M. Controlled Release of Acyclovir Through Bioengineered Corneal Implants with Silica Nanoparticle Carriers. The Open Tissue Engineering and Regenerative Medicine Journal 2010; 3(8):10-7.

[25] Granzco G R S. Collagen cross-linking: a new treatment paradigm in corneal disease—a review. Clinical and Experimental Ophthalmolory 2010; 38:141-53.

[26] Caporossi A, Mazzotta C, Baiocchi S, Caporossi T. Long-term results of riboflavin ultraviolet a corneal collagen cross-linking for keratoconus in Italy: the Siena eye cross study. Am J Ophthalmol. 2010; 149(4):585-93.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A method of manufacturing a hydrogel having a white light transmission of at least 70%, the method comprising:
   a) mixing at room temperature a collagen and a carbodiimide crosslinker, wherein the carbodiimide crosslinker is (N-Cyclohexyl-N'-(2-morpholinoethyl)carbodiimide) (CMC) or a metho-p-toluenesulfonate salt thereof, and the molar equivalent ratio of carbodiimide crosslinker to collagen amine groups is from about 0.3 to about 0.7; and
   b) casting the mixture into a mold prior to gelation, wherein the time to gelation at room temperature is increased relative to use of the crosslinker 1-Ethyl-3-[3-dimethylaminopropyl]carbodiimide (EDC).

2. The method of claim 1, wherein the carbodiimide crosslinker is water soluble.

3. The method of claim 1, wherein the collagen is recombinant human type III collagen.

4. The method of claim 1, wherein the hydrogel is a composite additionally comprising a water-soluble acrylic, methacrylic, or acrylamide.

5. The method of claim 4, wherein the water-soluble acrylic, methacrylic, or acrylamide is one or more of MPC (2-methacryloyloxyethyl phophorylcholine) and PEG-DA (polyethylene glycol-diacrylate).

6. The method of claim 1, wherein prior to mixing, the collagen is treated to photo polymerization.

7. The method of claim 1, wherein the molar equivalent ratio of carbodiimide crosslinker to collagen amine groups is about 0.5.

8. The method of claim 1, wherein gelation time is 2.5- to 4-fold longer compared to crosslinking using EDC.

* * * * *

UNITED STATES PATENT AND TRADEMARK OFFICE
CERTIFICATE OF CORRECTION

PATENT NO. : 9,987,225 B2  
APPLICATION NO. : 13/499088  
DATED : June 5, 2018  
INVENTOR(S) : May Griffith et al.

Page 1 of 1

It is certified that error appears in the above-identified patent and that said Letters Patent is hereby corrected as shown below:

On the Title Page

(73) Assignees: Ottawa Hospital Research Institute, Ottawa, (CA)  
Please add second Assignee --"University of Ottawa, Ottawa (CA)"--

Signed and Sealed this  
Thirtieth Day of April, 2019

Andrei Iancu  
*Director of the United States Patent and Trademark Office*